US012742203B2

(12) United States Patent
Peytavi et al.

(10) Patent No.: US 12,742,203 B2
(45) Date of Patent: Sep. 22, 2026

(54) ROTATABLE DISCS AND SYSTEMS AND METHODS FOR SAMPLE ANALYSIS

(71) Applicant: Autonomous Medical Devices Incorporated, Santa Ana, CA (US)

(72) Inventors: Regis Peytavi, Laguna Niguel, CA (US); Horacio Kido, Lake Forest, CA (US)

(73) Assignee: AUTONOMOUS MEDICAL DEVICES INCORPORATED, Santa Ana, CA (US)

( * ) Notice: Subject to any disclaimer, the term of this patent is extended or adjusted under 35 U.S.C. 154(b) by 0 days.

(21) Appl. No.: 19/334,361

(22) Filed: Sep. 19, 2025

(65) Prior Publication Data

US 2026/0092319 A1 Apr. 2, 2026

Related U.S. Application Data

(63) Continuation of application No. PCT/US2024/020816, filed on Mar. 20, 2024.

(60) Provisional application No. 63/598,903, filed on Nov. 14, 2023, provisional application No. 63/528,557, (Continued)

(51) Int. Cl.

| | |
|---|---|
| ***C12Q 1/686*** | (2018.01) |
| ***B01L 3/00*** | (2006.01) |
| ***B01L 7/00*** | (2006.01) |

(52) U.S. Cl.

CPC ........ *C12Q 1/686* (2013.01); *B01L 3/502715* (2013.01); *B01L 7/52* (2013.01); *B01L 2200/04* (2013.01); *B01L 2200/16* (2013.01); *B01L 2300/0803* (2013.01); *B01L 2300/1816* (2013.01)

(58) Field of Classification Search

CPC ............ C12Q 2565/629; C12Q 1/6844; C12Q 1/6806; B01L 2400/0409; B01L 2300/0803

See application file for complete search history.

(56) References Cited

U.S. PATENT DOCUMENTS

| | | | |
|---|---|---|---|
| 6,821,771 | B2 | 11/2004 | Festoc et al. |
| 7,998,708 | B2 | 8/2011 | Handique et al. |
| 8,105,783 | B2 | 1/2012 | Handique |

(Continued)

FOREIGN PATENT DOCUMENTS

| | | | |
|---|---|---|---|
| EP | 0953635 | A1 | 11/1999 |
| EP | 2316569 | A1 | 5/2011 |

(Continued)

OTHER PUBLICATIONS

Gaertig, Cornelia. et al. Development of a point-of-care-device for fast detection of periodontal pathogens. BMC Oral Health 15:165, 1-8 (2015).

(Continued)

*Primary Examiner* — Young J Kim

(74) *Attorney, Agent, or Firm* — WILSON SONSINI GOODRICH & ROSATI

(57) ABSTRACT

The present invention describes a method and device enabling sample processing, fast polymerase chain reaction amplification, and real-time reading of a large number of targets simultaneously while using a volume of reaction compatible with molecular assays. The present invention can be part of a cartridge allowing sample to answer nucleic acid analytic system (NAAT) or can be used as a stand-alone device.

30 Claims, 41 Drawing Sheets

Specification includes a Sequence Listing.

Related U.S. Application Data filed on Jul. 24, 2023, provisional application No. 63/453,724, filed on Mar. 21, 2023.

(56) References Cited

U.S. PATENT DOCUMENTS

| | | | | |
|---|---|---|---|---|
| 8,415,103 | B2 | 4/2013 | Handique | |
| 8,697,362 | B2 | 4/2014 | Knapp et al. | |
| 9,040,288 | B2 | 5/2015 | Handique et al. | |
| 9,102,911 | B2 | 8/2015 | Ririe et al. | |
| 9,132,427 | B2 | 9/2015 | Joseph et al. | |
| 9,522,397 | B2 | 12/2016 | Khattak et al. | |
| 10,076,757 | B2 | 9/2018 | De Vos | |
| 10,272,434 | B2 | 4/2019 | Khattak et al. | |
| 10,603,664 | B2 | 3/2020 | Khattak et al. | |
| 10,821,436 | B2 | 11/2020 | Handique et al. | |
| 10,889,856 | B2 | 1/2021 | Ririe et al. | |
| 10,907,202 | B2 | 2/2021 | Smith et al. | |
| 11,162,130 | B2 | 11/2021 | Andreyev et al. | |
| 11,371,075 | B2 | 6/2022 | Mahony et al. | |
| 11,732,315 | B2 | 8/2023 | Tanner et al. | |
| 11,866,774 | B2 | 1/2024 | Ririe et al. | |
| 11,969,731 | B2 | 4/2024 | Ririe et al. | |
| 12,103,003 | B2 | 10/2024 | Henley et al. | |
| 12,123,052 | B2 | 10/2024 | Smith et al. | |
| 12,275,013 | B2 | 4/2025 | Ririe et al. | |
| 2003/0008308 | A1 | 1/2003 | Enzelberger et al. | |
| 2008/0176290 | A1 | 7/2008 | Joseph et al. | |
| 2009/0258415 | A1 | 10/2009 | Bryning et al. | |
| 2010/0086990 | A1 | 4/2010 | Stanley et al. | |
| 2013/0171697 | A1 * | 7/2013 | Park | C12N 1/08 536/25.41 |
| 2014/0004501 | A1 | 1/2014 | Talebpour et al. | |
| 2014/0011266 | A1 | 1/2014 | Webster et al. | |
| 2016/0375441 | A1 | 12/2016 | Stanley et al. | |
| 2021/0322980 | A1 | 10/2021 | Wang et al. | |
| 2021/0395839 | A1 | 12/2021 | Ranoa et al. | |
| 2022/0080403 | A1 | 3/2022 | McNall et al. | |
| 2023/0158491 | A1 | 5/2023 | Pierson et al. | |
| 2024/0002957 | A1 | 1/2024 | Geva-Zatorsky et al. | |
| 2024/0009671 | A1 | 1/2024 | Yoo | |
| 2024/0058818 | A1 | 2/2024 | Miller et al. | |
| 2024/0226877 | A9 | 7/2024 | Ramel et al. | |
| 2024/0269680 | A1 | 8/2024 | Ririe et al. | |
| 2025/0011851 | A1 | 1/2025 | Hama et al. | |
| 2025/0177977 | A1 | 6/2025 | Andreyev et al. | |

FOREIGN PATENT DOCUMENTS

| | | | |
|---|---|---|---|
| EP | 2001990 | B1 | 6/2016 |
| EP | 3088083 | B1 | 8/2018 |
| EP | 3707276 | A4 | 2/2022 |
| EP | 3992300 | A1 | 5/2022 |
| EP | 3898230 | A4 | 9/2022 |
| EP | 3663408 | B1 | 5/2024 |
| EP | 4633810 | A2 | 10/2025 |
| WO | WO-2008106719 | A1 | 9/2008 |
| WO | WO-2009105499 | A1 | 8/2009 |
| WO | WO-2012161566 | A1 | 11/2012 |
| WO | WO-2013167716 | A2 | 11/2013 |
| WO | WO-2019094784 | A1 | 5/2019 |
| WO | WO-2020131779 | A1 | 6/2020 |
| WO | WO-2022150385 | A1 | 7/2022 |
| WO | WO-2023131534 | A1 | 7/2023 |
| WO | WO-2023235875 | A1 | 12/2023 |
| WO | WO-2024022143 | A1 | 2/2024 |
| WO | WO-2024197099 | A1 | 9/2024 |
| WO | WO-2024206756 | A1 | 10/2024 |
| WO | WO-2025024604 | A1 | 1/2025 |
| WO | WO-2025064904 | A1 | 3/2025 |

OTHER PUBLICATIONS

Garneret, Pierre. et al. Performing point-of-care molecular testing for SARS-CoV-2 with RNA extraction and isothermal amplification. PLoS One 16(1):e0243712, 1-9 (2021).

PCT/US2024/020816 International Search Report and Written Opinion dated Aug. 30, 2024.

Chen, Dafeng. et al. An integrated, self-contained microfluidic cassette for isolation, amplification, and detection of nucleic acids. Biomedical microdevices 12(4):705-719 (2010).

Madadelahi, Masoud. et al. A roadmap to high-speed polymerase chain reaction (PCR): COVID-19 as a technology accelerator. Biosensors and bioelectronics 246:115830, 1-25 (2024).

Martensson, Gustaf. et al. Rapid PCR amplification of DNA utilizing Coriolis effects. European biophysics journal : EBJ 35(6):453-458 (2006).

PCT/US2023/067879 International Search Report and Writte Opinion dated Sep. 27, 2023.

Smyrlaki, Ioanna. et al. Massive and rapid COVID-19 testing is feasible by extraction-free SARS-CoV-2 RT-PCR. Nature Communications 11(1):1-12 (2020).

* cited by examiner

1102
Sample release from hyperbaric chamber

SEQUENCE LISTING

```
Sequence total quantity: 4
SEQ ID NO: 1              moltype = DNA  length = 23
FEATURE                   Location/Qualifiers
source                    1..23
                          mol_type = other DNA
                          organism = synthetic construct
SEQUENCE: 1
cgcacaaagc acagagcgtt cct                                          23

SEQ ID NO: 2              moltype = DNA  length = 23
FEATURE                   Location/Qualifiers
source                    1..23
                          mol_type = other DNA
                          organism = synthetic construct
SEQUENCE: 2
cgcayaaagc acagagygtt cct                                          23

SEQ ID NO: 3              moltype = DNA  length = 23
FEATURE                   Location/Qualifiers
source                    1..23
                          mol_type = other DNA
                          organism = synthetic construct
SEQUENCE: 3
cgcacaaagc acagagygtt cct                                          23

SEQ ID NO: 4              moltype = DNA  length = 23
FEATURE                   Location/Qualifiers
source                    1..23
                          mol_type = other DNA
                          organism = synthetic construct
SEQUENCE: 4
cgcayaaagc acagagcgtt cct                                          23
```

ROTATABLE DISCS AND SYSTEMS AND METHODS FOR SAMPLE ANALYSIS

CROSS-REFERENCE

This application is a continuation application of International Patent Application No. PCT/US2024/020816, filed Mar. 20, 2024, which application claims priority to U.S. Provisional Application No. 63/453,724, filed Mar. 21, 2023, U.S. Provisional Application No. 63/528,557, filed Jul. 24, 2023, and U.S. Provisional Application No. 63/598,903, filed Nov. 14, 2023, which applications are incorporated herein by reference.

SEQUENCE LISTING

The instant application contains a Sequence Listing which has been submitted electronically in XML format and is hereby incorporated by reference in its entirety. Said XML copy, created on Dec. 12, 2025, is named 61070-706_301_SL.xml and is 4,594 bytes in size.

BACKGROUND

Detection of pathogens and tumor analysis by nucleic acid amplification is replacing other technologies, e.g., culturing, as the new gold standard. With advances in microfluidics, some of these systems have moved from clinical laboratory improvement amendments (CLIA)-regulated laboratories toward CLIA-waived facilities closer to patients. Reducing the total analytical time (TAT) of these devices is paramount to provide results in less than 15 minutes, e.g., the average waiting time in a doctor's office.

In parallel, another trend of nucleic acid amplification test (NAAT) systems is to provide an overall picture of the cause of a specific syndrome, helping physicians to provide a more accurate diagnosis. These syndromic panel assays usually look for 20 or more nucleic acid targets at the same time. Current fast NAAT systems available in CLIA-waived facilities can only perform simplex or low plex nucleic acid analyses and thus cannot be used for syndromic panels.

Several challenges need to be addressed to bring a system to market with a method allowing 20 plex or more in less than 15 minutes. First, the nucleic acid amplification is preferably 10 minutes or below using a volume compatible with the sensitivity required for diagnostics. Second, the fluorescent reader is preferably able to read 20 targets or more simultaneously without delaying the amplification time. Finally, the fast amplification process is preferably compatible with a fluidic cartridge designed to automate the sample preparation.

Isothermal nucleic acid amplification such as EXPAR or RPA can provide NAAT in less than 10 minutes. However, those technologies cannot be easily multiplexed and lack polymerase chain reaction (PCR) sensitivity and robustness.

PCR is a robust NAAT amplification method that requires thermal cycling to achieve amplification. The overall time of the reaction is linked to the time needed for the PCR reagent to change temperature. Historically, poor thermal transfer and unoptimized chemistry made PCR a slow process. However, with the advancement of faster polymerases, mass production of DNA primers, and faster thermal cycling, PCR amplification under 10 minutes has been achieved. Yet integration of such fast PCR in a sample-to-answer system allowing to read 20 plex or more is still lacking.

SUMMARY

In certain embodiments, the disclosure provides point-of-care methods and systems for performing fast-PCR on biological samples, e.g., patient fluids. In certain embodiments, the systems and methods of the disclosure simultaneously and rapidly detect multiple target nucleic acid sequences in a biological sample.

In one aspect, the present disclosure provides a method of ultra-fast real-time polymerase chain reaction (PCR) for detecting the presence or absence of a target nucleic acid in a biological sample. In some embodiments, the method comprises: (a) loading a sample into a loading chamber on a rotatable disc, the rotatable disc further comprising a plurality of reaction chambers and a channel fluidly connecting the loading chamber to the plurality of reaction chambers; wherein the reaction chambers are loaded with a PCR reagent mixture comprising a primer and a fluorescent probe; wherein the sample flows to the plurality of reaction chambers via the channel thereby filling the reaction chambers following loading of the sample; (b) contacting the channel within the rotatable disc with a sealer, thereby sealing the channel and preventing fluid communication between the plurality of reaction chambers after filling; (c) rotating the rotatable disc to bring the plurality of reaction chambers adjacent to a first heating element maintained at a first temperature, thereby denaturing the target nucleic acid in the sample if present, thereby producing a denatured target nucleic acid; (d) rotating the rotatable disc to bring the plurality of reaction chambers adjacent to a second heating element maintained at a second temperature, thereby annealing the primer to the denatured target nucleic acid and replicating the denatured target nucleic acid; (e) exposing the plurality of reaction chambers to an excitation light of a first wavelength, thereby exciting the fluorescent probe; and (f) repeating steps (c) through (e) for multiple cycles and measuring an emission light of a second wavelength from the plurality of reaction chambers, wherein if emission light of a second wavelength is detected, the sample comprises the target nucleic acid. In some embodiments, the primer comprises an oligonucleotide sequence that is complementary to at least a portion of the target nucleic acid. In some embodiments, the fluorescent probe comprises a fluorophore selected from the group consisting of: fluorescein amidite (FAM), SUN™, TEX 615, and Cyanine-5 (Cy5). In some embodiments, the sealer is housed within an analytical device for real-time PCR. In some embodiments, the sealer is a heat sealer. In some embodiments, the channel defines a lumen with a diameter ranging from about 1 μm to about 1 mm. In some embodiments, the channel comprises a thermoplastic material that seals the channel when heated to a target temperature and compressed by the sealer. In some embodiments, the target temperature is from about 1100° C. to about 300° C. In some embodiments, the sealer comprises a first element configured to provide a thermal energy and a pressure on the rotatable disc and a second element configured to provide a counter force to the pressure. In some embodiments, contacting the rotatable disc with the sealer comprises applying the pressure on the rotatable disc opposite to the counter force at one or more positions along the channel such that the channel deforms and creates the plurality of reaction chambers. In some embodiments, the excitation light or the emission light comprises two or more wavelengths. In some embodiments, the first wavelength and second wavelength are independently selected from about 400 nm to about 750 nm. In some embodiments, the sample is mixed with a primer complementary to at least a portion of the target nucleic acid pre-loaded within the plurality of reaction chambers. In some embodiments, the plurality of reaction chambers further comprises a probe, and wherein the sample is further mixed with the probe.

In one aspect, the present disclosure provides a method for multiplexed real-time amplification and detection of a plurality of different target nucleic acids in a biological sample, the method comprising: (a) loading a sample into a loading chamber on a rotatable disc, the rotatable disc further comprising a plurality of reaction chambers and a channel fluidly connecting the loading chamber to the plurality of reaction chambers, wherein the reaction chambers are loaded with a PCR reagent mixture comprising a plurality of primers and a plurality of fluorescent probes, wherein the sample is mixed with the plurality of primers, wherein each of the plurality of primers is complementary to a portion of a corresponding target nucleic acid of the plurality of different target nucleic acids, wherein the sample flows to the plurality of reaction chambers via the channel thereby filling the reaction chambers following loading of the sample; (b) contacting the channel within the rotatable disc with a sealer, thereby sealing the channel and preventing fluid communication between the plurality of reaction chambers after filling; (c) rotating the rotatable disc to bring the plurality of reaction chambers adjacent to a first heating element maintained at a first temperature, thereby denaturing each of the plurality of target nucleic acids in the sample if present, thereby producing a plurality of denatured target nucleic acids; (d) rotating the rotatable disc to bring the plurality of chambers adjacent to a second heating element maintained at a second temperature, thereby annealing the plurality of primers to the corresponding plurality of denatured target nucleic acids and replicating the plurality of different target nucleic acids; (e) exposing the plurality of reaction chambers to an excitation light comprising a plurality of excitation wavelengths, thereby exciting the plurality of fluorescent probes; (f) repeating steps (c) through (e) for multiple cycles and measuring a plurality of emitted lights of a plurality of emission wavelengths from the plurality of reaction chambers, wherein each of the plurality of emission wavelengths corresponds to the presence of each of the plurality of different target nucleic acids, wherein if emitted light of an emission wavelength is detected, the sample comprises the corresponding target nucleic acid. In some embodiments, the sealer is a heat sealer. In some embodiments, the sealer is housed within an analytical device for multiplexed real-time amplification. In some embodiments, the channel defines a lumen with a diameter ranging from about 1 μm to about 1 mm. In some embodiments, each of the plurality of excitation wavelengths and the plurality of emission wavelengths are each independently selected from about 400 nm to about 750 nm. In some embodiments, the plurality of primers is stored in the plurality of reaction chambers. In some embodiments, the plurality of primers is provided as a lyophilized powder. In some embodiments, the sample comprises a bodily sample selected from the group consisting of: a blood sample, a lacrimal fluid sample, a saliva sample, a mucus sample, a sputum sample, a feces sample, a cerebrospinal fluid sample, and a urine sample. In some embodiments, a fluorescent probe in the plurality of fluorescent probes comprises a fluorophore selected from the group consisting of: fluorescein amidite (FAM), SUN™, TEX 615, and Cyanine-5 (Cy5). In some embodiments, the first heating element, the second heating element, or the third heating element comprises a heating block. In some embodiments, the probe is provided as a lyophilized powder. In some embodiments, the rotatable disc comprises hard plastic. In some embodiments, components of the PCR reagent mixture are pre-mixed before contacting the sample or loading to the plurality of reaction chambers. In some embodiments, the PCR reagent mixture is provided in a reagent mixing chamber and the sample is mixed with second PCR reagent mixture in the reagent mixing chamber. In some embodiments, the PCR reagent mixture is provided as a lyophilized powder. In some embodiments, the sample is mixed with the PCR reagent mixture prior to transferring into the plurality of reaction chambers in (a). In some embodiments, the plurality of reaction chambers are each aligned at the same radial distance from a center of the rotatable disc and are equally spaced from each other. In some embodiments, the plurality of reaction chambers occupies 360 degrees of arc on the rotatable disc. In some embodiments, the plurality of reaction chambers occupies a section from about 10 degrees to 100 degrees of arc on the rotatable disc. In some embodiments, each of the plurality of reaction chambers comprises a volume of from about 5 μL to about 100 μL and further comprises a depth from about 0.1 mm to about 1.0 mm. In some embodiments, the plurality of reaction chambers comprises a depth from about 0.1 mm to about 0.7 mm. In some embodiments, the plurality of reaction chambers comprises a depth of at most about 0.25 mm. In some embodiments, the first temperature is maintained for a first period of time and the second temperature is maintained for a second period of time. In some embodiments, the first period of time is selected from about 500 ms to about 2 s and the second period of time is selected from about 3 s to about 18 s. In some embodiments, the first temperature is selected from about 900° C. to about 990° C. and the second temperature is selected from about 500° C. to about 740° C. In some embodiments, the first heating element comprises a first radial length, and the second heating element comprises a second radial length. In some embodiments, the second radial length is about 6 to about 9 times the first radial length. In some embodiments, the third temperature is selected from about 650° C. to about 750° C. In some embodiments, the third temperature is maintained for a third period of time. In some embodiments, the third period of time is selected from about 1 s to about 6 s. In some embodiments, the third heating element comprises a third radial length. In some embodiments, the third radial length is about 2 to about 3 times the radial length of the first radial length. In some embodiments, the emission light is measured on a first fluorescence detector or a plurality of fluorescence detectors. In some embodiments, the first detector or plurality of fluorescence detectors comprises one or more wavelength channels to measure an emission intensity of the second wavelength or the plurality of emission wavelengths.

In one aspect, the present disclosure provides a rotatable disc, comprising: a loading chamber; a plurality of reaction chambers; and a channel connecting the loading chamber to the plurality of reaction chambers; wherein the channel comprises a thermoplastic material that seals the channel when heated to a temperature of 110 to 3000° C. In some embodiments, each of the plurality of reaction chambers is aligned at the same radial distance from the center of the rotatable disc. In some embodiments, each of the plurality of reaction chambers contains a first PCR reaction mixture comprising: a primer and a fluorescent probe. In some embodiments, the loading chamber comprises a second PCR reaction mixture comprising a polymerase and a plurality of nucleotides.

In one aspect, the present disclosure provides a rotatable disc, comprising: a loading chamber; a plurality of reaction chambers, each aligned at substantially the same radial distance from the center of the rotatable disc, wherein each of the plurality of reaction chambers comprises a first PCR reaction mixture comprising a primer; and a channel connecting the loading chamber to the plurality of reaction chambers. In some embodiments, the loading chamber comprises a second PCR reaction mixture comprising a polymerase and a plurality of nucleotides. In some embodiments, the channel comprises a thermoplastic material that seals the channel when heated to a temperature of 110 to 3000° C. In some embodiments, each of the plurality of reaction chambers comprises a volume of from about 5 μL to about 100 μL. In some embodiments, each of the plurality of reaction chambers comprises a depth of from about 0.1 mm to about 1.0 mm. In some embodiments, the plurality of reaction chambers comprises a depth from about 0.2 to about 0.7 mm. In some embodiments, each of the plurality of reaction chambers comprises a depth of at most 0.25 mm. In some embodiments, each of the plurality of reaction chambers are equally spaced from each other. In some embodiments, the plurality of reaction chambers occupies 360 degrees of arc on the rotatable disc. In some embodiments, the plurality of reaction chambers occupies a section from about 10 degrees to 100 degrees of arc on the rotatable disc. In some embodiments, the plurality of reaction chambers comprises from one to 100 reaction chambers. In some embodiments, the thermoplastic material is selected from polycarbonate, polypropylene, polyethylene terephthalate, and cyclic olefin copolymer. In some embodiments, the thermoplastic material has a thickness from about 10 μm to about 400 μm. In some embodiments, the channel comprises a z dimension from about 1 μm to about 1 mm, a width from about 1 mm to about 5 mm, and a depth of at most about 200 μm. In some embodiments, the channel comprises a width from about 2 mm to about 4 mm and a depth of at most about 100 μm. In some embodiments, the aspect ratio is at least 10 to 1. In some embodiments, the aspect ratio is at least 20 to 1. In some embodiments, each of the plurality of reaction chambers has an interior and an exterior. In some embodiments, each of the plurality of reaction chambers is compatible with transmitting an excitation light of a plurality of wavelengths from the exterior of the plurality of reaction chambers and the plurality of reaction chambers is compatible with transmitting an emitted light of a plurality of wavelengths from the interior of the plurality of reaction chambers. In some embodiments, the rotatable disc comprises a thermoformed film and a sealing film that are coupled together to form the plurality of reaction chambers. In some embodiments, the thermoformed film forms a shape and a size for the plurality of reaction chambers and a shape and size for the channel. In some embodiments, the sealing film is sealed to the thermoformed film. In some embodiments, the sealing film is sealed to the thermoformed film via a skeleton with two faces coextruded with heat sealed compliant material. In some embodiments, the thermoformed film comprises a thickness of from about 50 μm to about 500 μm. In some embodiments, a ratio of the width of the channel to the thickness of the thermoformed film is greater than two. In some embodiments, the sealing film comprises a thickness of from about 10 μm to about 500 μm. In some embodiments, the thermoformed film has a glass transition temperature (Tg) higher than about 1000° C. In some embodiments, the sealing film and thermoformed film comprise a resin. In some embodiments, the resin comprises a single polymer. In some embodiments, the resin comprises an inner polymer and an outer polymer, and the inner polymer has a lower Tg than the outer polymer. In some embodiments, the single polymer, the inner polymer, and the outer polymer are each independently selected from polyolefin, polycarbonate, polystyrene, polymethyl methylacrylate, polyethylene, and polypropylene. In some embodiments, the resin for the sealing film and the resin for the thermoformed film can be heat sealed together. In some embodiments, the resin for the sealing film and thermoformed films is the same.

In one aspect, the present disclosure provides a rotatable disc, comprising: a loading chamber; a plurality of reaction chambers, each aligned at the same radial distance from the center of the rotatable disc; and a channel connecting the loading chamber to the plurality of reaction chambers, wherein the channel comprises a thermoformed thermoplastic film sealed to a sealing thermoplastic film, and wherein the channel has a depth from 10 micrometers to 500 micrometers.

In one aspect, the present disclosure provides a rotatable disc, comprising: a loading chamber; a plurality of reaction chambers, each aligned at the same radial distance from the center of the rotatable disc; and a channel connecting the loading chamber to the plurality of reaction chambers, wherein the channel is heat sealed by compressing a thermoformed film of a ceiling of the channel in contact with a sealing film of a floor of the channel.

In one aspect, the present disclosure provides a rotatable disc, comprising: a loading chamber; a plurality of reaction chambers, each aligned at the same radial distance from the center of the rotatable disc; and a channel connecting the loading chamber to the plurality of reaction chambers, wherein the channel comprises coextrude thermoplastic film with an inner thermoplastic film layer having a lower Tg than an outer thermoplastic film layer, and wherein the inner layer is configured to seal the channel when heated to a temperature of 1100 Celsius to 3000 Celsius.

In one aspect, the present disclosure provides a rotatable disc, comprising: a loading chamber configured to seal a sample in a hyperbaric condition to a temperature above 1000 Celsius; a plurality of reaction chambers, each aligned at the same radial distance from the center of the rotatable disc; and a channel connecting the loading chamber to the plurality of reaction chambers. In some embodiments, the loading chamber is configured to seal a sample in a hyperbaric condition to a temperature from 1010 Celsius to 1600 Celsius. In some embodiments, the channel is heat sealed by compressing a thermoformed film of a ceiling of the channel in contact with a sealing film of a floor of the channel. In some embodiments, the loading chamber is configured to be heated by induction heating. In some embodiments, the loading chamber comprises a chelating agent, a single stranded nucleic acid binding protein, and a reducing agent. In some embodiments, the loading chamber further comprises a stabilizer.

In one aspect, the present disclosure provides a system for real-time polymerase chain reaction (PCR) comprising: (a) a rotatable disc comprising a loading chamber, a plurality of reaction chambers, and a channel connecting the loading chamber to the plurality of reaction chambers; (b) a sample holder for holding the rotatable disc in a substantially horizontal plane, the device configured to rotate the rotatable disc within the substantially horizontal plane; (c) a sealer and coupled to an actuator that moves the sealer, thereby changing a distance between the sealer and the rotatable disc; (d) a first heating element maintained at a first temperature located in close proximity to a second portion of the rotatable disc; (e) a second heating element maintained at a second temperature located in close proximity to a second portion of the rotatable disc; (f) a light source oriented to generate an excitation light of a first wavelength into the horizontal plane occupied by the reaction chambers of the rotatable disc; and (g) a first light detector oriented to detect emitted light of a second wavelength emitted from the reaction chambers of the rotatable disc; wherein when a liquid sample comprising a nucleic acid flows from the loading chamber to the plurality of reaction chambers via channel, the rotatable disc is brought in contact with the heat sealer, thereby sealing the channel and preventing fluid communication between the plurality of reaction chambers; wherein the rotatable disc is rotated in the substantially horizontal plane to (i) bring the plurality of reaction chambers adjacent to the first heating element, thereby denaturing the nucleic acid in the sample, (ii) bring the plurality of reaction chambers adjacent to the second heating element, thereby annealing the primer to the denatured nucleic acid and replicating the nucleic acid; and (iii) orient the rotatable disc such that the excitation light generated by the light source enters the reaction chamber, thereby generating the emitted light that is emitted from the reaction chamber and detected by the light detector. In some embodiments, the liquid sample from the loading chamber mixes with a PCR reagent mixture comprising a polymerase and a plurality of nucleotides in the mixing chamber prior to flowing via the channel to the plurality of reaction chambers. In some embodiments, each of the plurality of reaction chambers is preloaded with PCR reagents comprising a primer and a probe. In some embodiments, the loading chamber is configured to be heated by induction heating; and (b) an analytical device, comprising: (i) a sample holder for receiving the rotatable disc in a substantially horizontal plane, the sample holder configured to rotate the rotatable disc within the substantially horizontal plane; (ii) a first heating element configured to contact the reaction chambers and heat the plurality of reaction chambers to a first temperature; and (iii) a second heating element configured to contact the reaction chambers and heat the plurality of reaction chambers to a second temperature. In some embodiments, the loading chamber is centrally located on the rotatable disc. In some embodiments, the plurality of reaction chambers is located on the periphery of the rotatable disc.

In one aspect, the present disclosure provides a system for real-time polymerase chain reaction (PCR) comprising: (a) a rotatable disc comprising a loading chamber, a plurality of reaction chambers, and a channel connecting the loading chamber to the plurality of reaction chambers; and (b) an analytical device comprising: (i) a sample holder for receiving the rotatable disc in a substantially horizontal plane, the sample holder configured to rotate the rotatable disc within the substantially horizontal plane; (ii) a first heating element configured to heat the loading chamber to a first temperature above 100 degrees Celsius; (iii) a second heating element configured to contact the reaction chambers and heat the plurality of reaction chambers to a second temperature; and (iv) a third heating element configured to contact the reaction chambers and heat the plurality of reaction chambers to a third temperature. In some embodiments, the first heating element is configured to heat the loading chamber to a first temperature from 1010 Celsius to 160° Celsius.

In one aspect, the present disclosure provides a system for real-time polymerase chain reaction (PCR) comprising: (a) a rotatable disc comprising a loading chamber, a plurality of reaction chambers, and a channel connecting the loading chamber to the plurality of reaction chambers, wherein the loading chamber comprises a chelating agent, a single stranded nucleic acid binding protein, and a reducing agent; and (b) an analytical device comprising: (i) a sample holder for receiving the rotatable disc in a substantially horizontal plane, the sample holder configured to rotate the rotatable disc within the substantially horizontal plane; (ii) a first heating element configured to contact the reaction chambers and heat the plurality of reaction chambers to a first temperature; and (iii) a second heating element configured to contact the reaction chambers and heat the plurality of reaction chambers to a second temperature. In some embodiments, the analytical device further comprises a light source oriented to generate an excitation light of a first wavelength into the horizontal plane occupied by the plurality of reaction chambers of the rotatable disc. In some embodiments, the analytical device further comprises a light detector oriented to detect emission light of a second wavelength emitted from the plurality of reaction chambers of the rotatable disc.

In one aspect, the present disclosure provides a method of processing a target nucleic acid, the method comprising: (a) loading a sample comprising a target nucleic acid into a loading chamber on a rotatable disc, the rotatable disc further comprising a reaction chamber and a channel connecting the loading chamber to the reaction chamber; (b) heating the sample comprising the target nucleic acid in the loading chamber in a hyperbaric condition to a temperature above 1000 Celsius to produce a processed sample; (c) rotating the rotatable disc such that the processed sample flows to the reaction chamber via the channel; and (d) amplifying the target nucleic acid in the processed sample in the reaction chamber.

In one aspect, the present disclosure provides a method of processing a target nucleic acid, the method comprising: (a) loading a sample comprising a target nucleic acid into a loading chamber on a rotatable disc, the rotatable disc further comprising a reaction chamber and a channel connecting the loading chamber to the reaction chamber; (b) heating the sample comprising the target nucleic acid in the loading chamber in a hyperbaric condition to a temperature above 1000 Celsius to produce a processed sample; (c) rotating the rotatable disc such that the processed sample flows into the reaction chamber via the channel; and (d) contacting the rotatable disc with a sealer, thereby sealing the channel after the processed sample flows into the reaction chamber. In some embodiments, the heating comprises heating the sample to a temperature from 101° Celsius to 160° Celsius. In some embodiments, the heating occurs at a temperature ramp rate from 5° Celsius per second to 500 Celsius per second. In some embodiments, the sample comprising the target nucleic acid further comprises one or more reagents selected from the group consisting of: a chelating agent, a single stranded nucleic acid binding protein, a reducing agent, and a stabilizer. In some embodiments, the loading chamber is preloaded with one or more reagents selected from the group consisting of: a chelating agent, a single stranded nucleic acid binding protein, a reducing agent, and a stabilizer; and the sample mixes with the one or more reagents in the loading chamber. In some embodiments, the sample comprising the target nucleic acid comprises a bodily sample selected from the group consisting of: a blood sample, a lacrimal fluid sample, a saliva sample, a mucus sample, a sputum sample, a feces sample, a cerebrospinal fluid sample, and a urine sample. In some embodiments, the target nucleic acid is not extracted, isolated, or otherwise purified from the bodily sample prior to heating. In some embodiments, the sample comprising the target nucleic acid comprises a plurality of molecular amplification inhibitors and the heating inactivates a molecular amplification inhibitor of the plurality of molecular amplification inhibitors in the sample. In some embodiments, the heating inactivates at least 70% of the plurality of molecular amplification inhibitors to produce the processed sample.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 5A illustrates two components used to manufacture some embodiments of a rotatable disc described herein. FIG. 5B illustrates a close-up example of a reaction chamber comprised on a rotatable disc described herein. FIG. 5C illustrates an additional view of a manufactured rotatable disc comprising a plurality of reaction chambers designed for RT-PCR.

FIG. 8A illustrates a front view of the analytical device. FIG. 8B illustrates a side view of the analytical device.

FIG. 9A illustrates an overview of the heat sealer housed within an analytical above the channel on the rotatable disc. FIG. 9B illustrators a close view of the heat sealer housed within an analytical above the channel on the rotatable disc. FIG. 9C illustrates an overview of the heat sealer housed within an analytical device contact with the channel on the rotatable disc. FIG. 9D illustrators a close view of the heat sealer housed within an analytical device contact with the channel on the rotatable disc.

FIG. 13A shows an example of a manufactured rotatable disc. FIG. 13B shows an example of a close-up view for the sealed channels on the rotatable disc. FIG. 13C shows an example of the analytical device used for processing a target nucleic acid (e.g., RT-PCR).

FIG. 14A illustrates signal detection by one color channel implemented within the device. FIG. 14B illustrates signal detection by two color channels implemented within the device.

FIG. 15A shows a side view, FIG. 15B shows a top view, and FIG. 15C shows a bottom view of the hyperbaric heating vessel.

FIG. 16A shows a side view, and FIG. 16B shows a cut view of the hyperbaric heating vessel and the duckbill valve.

FIG. 20A illustrates the movement of the sample during sample injection and provides a zoom-in view of the outlet channel and closed laser valve. FIG. 20B illustrates the movement of the sample during sample release and provides a zoom-in view of the outlet channel and the sample movement through the open laser valve.

FIG. 23A shows the individual fluorescence traces collected for the PCR reactions using primer set PS3.3. FIG. 23B shows the individual fluorescence traces collected for the PCR reactions using primer set PS3.4.

FIG. 23C shows the individual fluorescence traces collected for the PCR reactions using primer set PS3.5. FIG. 23D shows the individual fluorescence traces collected for the PCR reactions using primer set PS3.6.

FIG. 24A shows the cycle threshold values for Flu A samples. FIG. 24B shows the cycle threshold values for Flu B samples.

FIG. 26A shows a diagram of the steps of the hyperbaric heating workflow. FIG. 26B shows the results from a time series experiment where a sample within a hyperbaric heating sample vessel was heated with magnetic induction. FIG. 26C shows an experiment where ribonuclease activity within a swab collected nasal matrix was measured by fluorescence acquisition after a 10 min incubation with a fluorescent RNA probe. FIG. 26D shows PCR cycle quantification for increasing volumes of hyperbaric heating-treated samples.

FIG. 27A shows PCR cycle quantification at multiple levels of contrived SARS-CoV-2 samples in a nasal specimen, for both hyperbaric heating-treated samples and Qiagen Viral RNA extraction. FIG. 27B shows PCR cycle quantification for two different bacterial organisms, *B. subtilis* and *B. cereus* spore. FIG. 27C shows PCR cycle quantification for *S. cerevisiae*.

DETAILED DESCRIPTION

Figure 1:
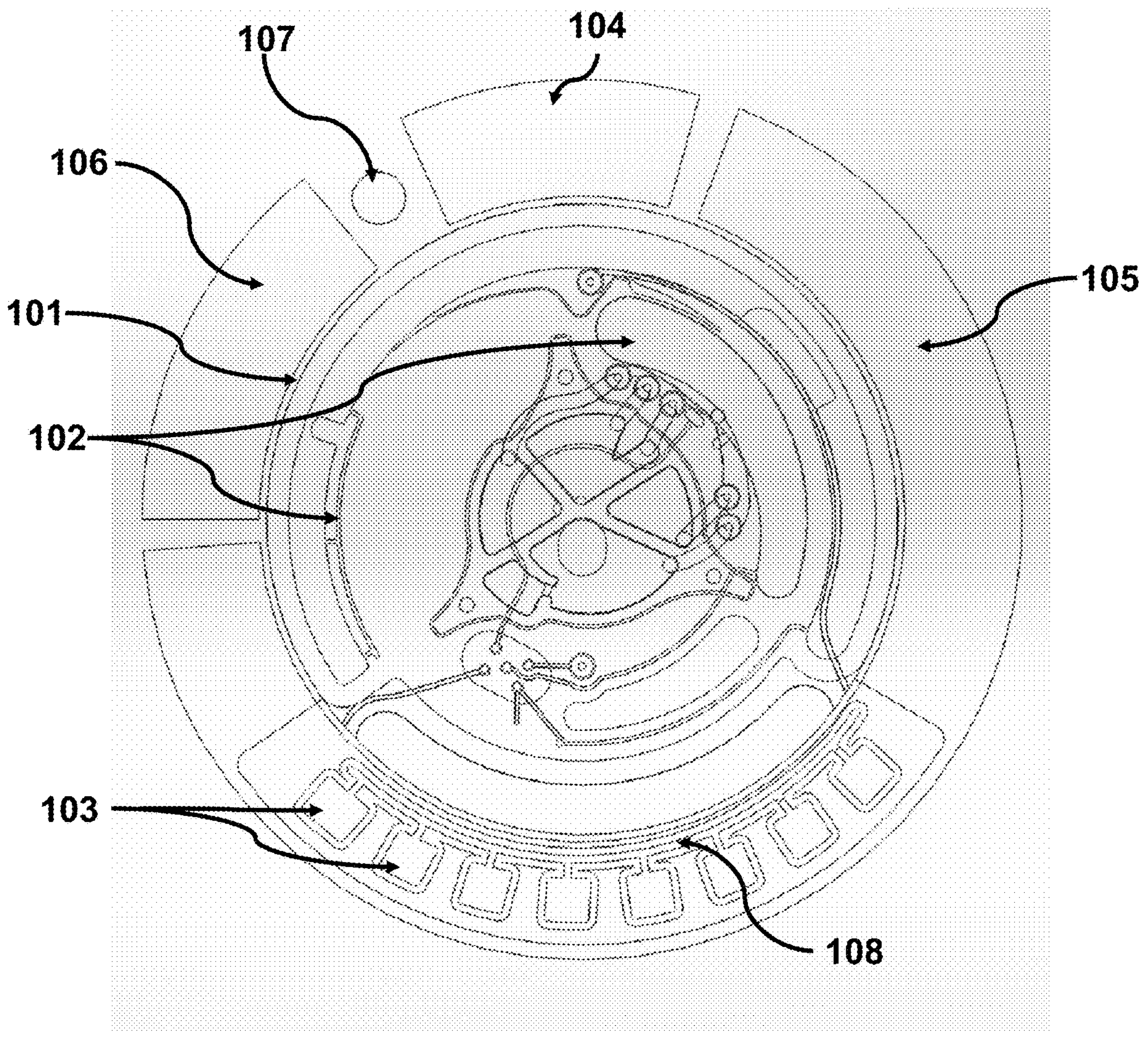
FIG. 1 illustrates a line drawing of a top view of a rotatable disc described herein in the context of an analytical device described herein.

The present disclosure provides a method and a system enabling ultra-fast real-time PCR for a high multiplexing assay from a volume comprising between about 20 and about 30 μL. The disclosed method may be readily integrated with a centripetal microfluidic device for sample preparation enabling a full sample-to-answer system. The system may be composed of a rotatable disc comprising PCR reaction chambers (e.g., cuvettes) located at the same radius from the center of rotation of the rotatable disc. These reaction chambers may be designed to allow an ultra-fast thermal transfer from an analytical device's heating blocks to the PCR reagents.

Two to three separate thermal blocks, e.g., heating blocks, set at a constant temperature of about 50° C. to about 98° C., may be arranged in a ring shape directly above and below the reaction chambers of the rotatable disc. In certain embodiments, the analytical device may have an optic head, placed at the same radius as the reaction chambers, that may detect one to 6 different wavelengths in the time it takes for the reaction chamber to pass over the sensor. The analytical device may have two distinct optic heads that can detect 2 different wavelengths each in the time it takes for the reaction chamber to pass over the sensor.

This disclosure further relates to a method for using the device, wherein after filling the reaction chambers via centripetal force, each reaction chamber may be sealed by contact or non-contact means to avoid evaporation and escape of the heated liquid. The thermocycling may be achieved by bringing the pair of heating blocks in contact with the reaction chambers in sequence, starting with denaturing block, followed by the annealing block, and optionally followed by the elongation block.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing genetic material. The biological entity can be a plant, animal, or microorganism, including, for example, bacteria, viruses, fungi, and protozoa. The subject can be tissues, cells, or fragments thereof, derived from a biological entity obtained in vivo or cultured in vitro. The subject can be a mammal, for example, a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the term "molecular amplification" refers to assay or method or test used to detect nucleic acids in sample. This can be used in, for example, experimental research, clinical medicine development, infectious diagnosis, gene cloning, and industrial quality control. Molecular amplification can also be used as part of a diagnostic test. The term "molecular amplification" referred herein intends to cover all methods that are designed to amplify (e.g., replicate, duplicate, etc.) nucleic acid thereby generating more copies of the nucleic acid in a sample. Molecular amplification comprises nucleic acid amplification, enzymatic amplification (e.g., PCR), isothermal amplification, and/or other alternative amplification methods that has been developed in the field.

As used herein, the terms "polymerase chain reaction" or "PCR" refers to a type of molecular or nucleic acid amplification that amplify or generate more copies of a nucleic acid template. The method of PCR can be used in conjunction with a method to detect, identify, and/or quantify the nucleic acid. The term "PCR" used herein intends to cover all different types of PCR, including, for example, sequential PCR and real-time PCR, or reverse transcription PCR (RT-PCR).

As used herein, the term "biological sample" means a sample containing nucleic acids/biological agents such as clinical (e.g., cell fractions, mucus membrane, nasal swab, whole blood, plasma, serum, urine, tissue, cells, etc.), agricultural, environmental (e.g., soil, mud, minerals, water, air), food, forensic, or any other biological samples. The sample may include infectious agents, such as, for example, viral, bacterial or parasitical infectious agents. With "whole blood," it is meant blood such as it is collected, e.g., by venous sampling, e.g. containing white and red cells, platelets, plasma, and any infectious agents that may be present. The clinical samples may be from human or animal origin. The sample analyzed can be solid or liquid in nature. It is evident when solid materials are used, these are first dissolved in a suitable solution as known in the art.

As used herein, the term "nucleic acid" refers to DNA molecules, e.g., cDNA or genomic DNA, RNA molecules, e.g., mRNA, DNA-RNA hybrids, and analogs of DNA or RNA produced using nucleotide analogs. Nucleic acid molecules comprise nucleotides, oligonucleotides, double-stranded DNA, single-stranded DNA, multi-stranded DNA, complementary DNA, genomic DNA, non-coding DNA, messenger RNA (mRNA), single-stranded RNA, microRNA (miRNA), and nuclear body small molecules. It may be RNA (snoRNA), ribosomal RNA (rRNA), transfer RNA (tRNA), small interfering RNA (siRNA), heteronuclear RNA (hnRNA), or small hairpin RNA (shRNA).

Overview

Centripetal microfluidics can be used for sample preparation and for fluorescence acquisition in multiple cuvettes during real-time PCR amplification. Thus, centripetal systems have been used both for sample to answer systems, such GenePOC, Spindiag or Simplexa, or for standalone real-time thermocycling systems, such as Rotorgene, light cycler or MIC. However, spinning the whole disposable can bring other challenges, especially for ultra-fast thermocycling In microfluidic systems, the liquid, after being pumped in the reaction chamber, may need to be maintained in place in order to avoid evaporation during the heating step of the PCR. In stationary pressure controlled microfluidic systems, it can be done by applying air pressure greater than the vapor pressure occurring during denaturation step.

One advantage of centripetal microfluidics can be that the centrifugal pumping is applied to the fluid without the need for any direct connection to the instrument, helping to prevent contamination. It may be difficult to apply air pressure to the system during thermocycling. Thus, liquid may need to be maintained in place during PCR cycling by continually spinning the disposable. However, ultra-fast heat transfers for ultra-fast thermocycling can be challenging when the disposable is spinning continually, since a non-contact heating and cooling strategy needs to be used. A non-contact cooling and heating system may be suboptimal.

For example, pulsed hot and cool air are used in GenePOC and Rotorgene to achieve the thermocycling. However, because of the poor thermal capacity of air, thermocycling can be slow in these technologies. Mic and Simplexa use contact between the disposable and a metallic holder heated via non-contact methods while spinning. Mic uses induction heating, while Simplexa uses an infrared lamp. Such methods still lack an efficient way to cool the PCR reagent fast. SpinDiag uses a fully electrified rotor, enabling heating and cooling of the disposable while spinning. This approach can make the instrument extremely complex. However, the cycling time can be too long to be considered ultra-fast.

Another challenge in enabling ultra-fast heat and cooling strategies in a centripetal device can be maintaining PCR reagents in place during heating. Another challenge can be prevention of evaporation in the PCR reactors. The present disclosure provides a way to fill all reactive chambers (e.g., cuvettes) in less than 30 seconds while being able to heat-seal each cuvette after it is filled with amplification reagent.

Channels for distributing liquid into reaction chambers formed by thermoformed thin film and enclosed by a heat-sealing film can be closed permanently by pressing the ceiling of the channel against the bottom sealing film. The seal, once applied, can prevent any liquid or steam from escaping. In various cases, the U shape of the channel can be crushed to bring the ceiling close to the bottom film to enable a tight seal.

The present disclosure relates to an analytical device, a rotatable disc, a method for preparing and processing samples, and a method for performing sample analysis, e.g., nucleic acid amplification such as polymerase chain reaction (PCR). In some embodiments, the analytical device comprises a thermocycling device comprising one or more reaction chambers. A nucleic acid-containing sample can be processed and/or analyzed within the one or more reaction chambers, e.g., in a PCR reaction. In some embodiments, the analytical device further comprises a heating chamber for sample preparation. Samples may be heated in this heating chamber prior to further processing and analysis in the plurality of reaction chambers. In some embodiments, the method for preparing and processing samples may comprise heating the sample in hyperbaric heating conditions to inactivate one or more nucleic acid amplification inhibitors prior to nucleic acid amplification. In some embodiments, the method for preparing and processing samples may comprise using a thermocycling device as described herein to amplify and analyze a nucleic acid.

The present disclosure provides a method of ultra-fast real-time polymerase chain reaction (PCR) for detecting the presence or absence of a target nucleic acid in a biological sample. In one aspect, the method comprises: (a) loading a sample into a loading chamber on a rotatable disc, the rotatable disc further comprising a plurality of reaction chambers and a channel fluidly connecting the loading chamber to the plurality of reaction chambers; wherein the reaction chambers are loaded with a PCR reagent mixture comprising a primer and a fluorescent probe; wherein the sample flows to the plurality of reaction chambers via the channel thereby filling the reaction chambers following loading of the sample; (b) contacting the channel within the rotatable disc with a sealer, thereby sealing the channel and preventing fluid communication between the plurality of reaction chambers after filling; (c) rotating the rotatable disc to bring the plurality of reaction chambers adjacent to a first heating element maintained at a first temperature, thereby denaturing the target nucleic acid in the sample if present, thereby producing a denatured target nucleic acid; (d) rotating the rotatable disc to bring the plurality of reaction chambers adjacent to a second heating element maintained at a second temperature, thereby annealing the primer to the denatured target nucleic acid and replicating the denatured target nucleic acid; (e) exposing the plurality of reaction chambers to an excitation light of a first wavelength, thereby exciting the fluorescent probe; and (f) repeating steps (c) through (e) for multiple cycles and measuring an emission light of a second wavelength from the plurality of reaction chambers, wherein if emission light of a second wavelength is detected, the sample comprises the target nucleic acid.

In some embodiments, the primer comprises an oligonucleotide sequence that is complementary to at least a portion of the target nucleic acid.

In some embodiments, the present disclosure may comprise an analytical device, wherein the analytical device comprises pairs of heating blocks (FIGS. 1, 104, 105, and 106) that are arranged at the same radius as a plurality of reaction chambers (e.g., cuvettes) (FIG. 1, 103) on the rotatable disc. In some embodiments, the rotatable disc may comprise a cuvette insert, wherein the cuvette insert comprises the plurality of reaction chambers (e.g., cuvettes). In some embodiments, the plurality of reaction chambers (e.g., cuvettes) (FIG. 1, 103) rotates between each heating block and stops at the location of each block for a dwelling time necessary for the corresponding PCR denaturing, annealing, or elongation steps.

In some embodiments, each pair of heating blocks may be mirrored across from the reaction chamber planes. Each pair of heating blocks may move perpendicularly to the reaction chamber plane. The heating blocks may have a speed comprising about 10 mm to about 200 mm per second. In some embodiments, the speed may be from about 50 mm to about 80 mm per second. In some embodiments, each heating block in the pair of heating blocks may be actuated separately. In some other embodiments, each heating block in the pair of heating blocks may be actuated at the same time.

In some embodiments, each pair of heating blocks may be set to a fixed temperature at the beginning of the reaction. Setting each pair of heating blocks to a fixed temperature may thereby allow rapid thermocycling. The reaction chambers may move in between heating blocks held at varying temperatures. This thus may avoid the inertia of changing the temperatures of the heating blocks themselves. In some embodiments, to minimize the required heating and cooling time, the heating blocks may be designed to have a thermal mass of at least about 4 times bigger than the reaction chamber's thermal mass.

In some embodiments, the pair of heating blocks may comprise a first heating block (FIG. 1 104, FIG. 7 704, FIG. 8A 802). The first heating block may be set at a temperature compatible with a PCR denaturing step. In some embodiments, the first heating block may be set at a fixed temperature from about 90° C. to about 99° C. In some embodiments, the pair of heating blocks may comprise a second heating block (FIG. 1 105, FIG. 7 705, FIG. 8A 803). The second heating block may be set at a temperature compatible with a PCR annealing step. In some embodiments, the second heating block may be set at a fixed temperature from about 50° C. to about 72° C. In some embodiments, the pair of heating blocks may comprise a third heating block (FIG. 1 106). The third heating block may be set at a temperature compatible with a PCR elongation step. In some embodiments, the third heating block may be set at a fixed temperature from about 70° C. to about 75° C. In some embodiments, a cooling step between the first heating block (set at the denaturation temperature) and the second heating block (set at the annealing temperature) may be provided by contacting the reaction chambers with the block set at the annealing temperature (e.g., 65° C.). In some embodiments, the bigger thermal mass of the block may adsorb the heat from the reaction chambers.

In some other embodiments, the pair of heating blocks comprises a first heating block (FIG. 7, 704) and a second heating block (FIG. 7, 705), located at the same radius. In some embodiments, the PCR annealing and elongation steps are performed by the same heating block (e.g., the second heating block). In some embodiments, the second heating block may be fixed to a temperature from about 50° C. to about 74° C. In some embodiments, the second heating block may be fixed to a temperature from about 65° C. to about 70° C.

Figure 10A:
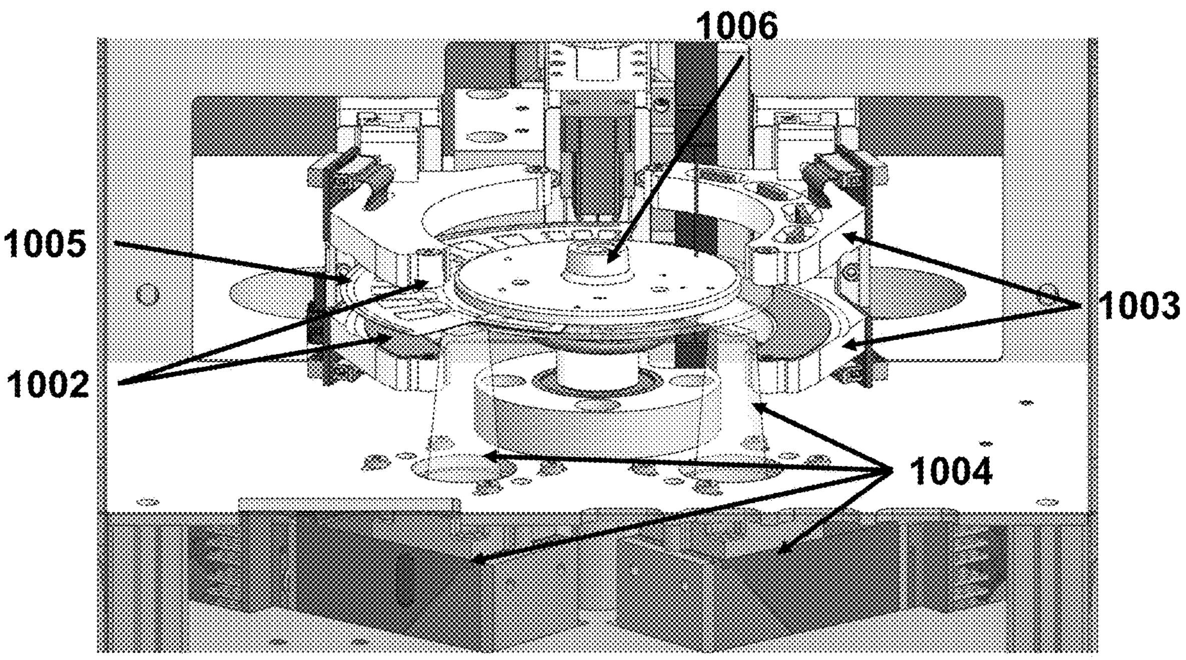
FIGS. 10A-10D illustrate a front-view cartoon schematic of an analytical device wherein the disclosed heating block elements clamp and unclamp the disclosed rotatable disc. A comparison of FIG. 10A to FIG. 10B illustrates the first pair of heating blocks clamping, or coming into contact with, the rotatable disc. A comparison of FIG. 10B to FIG. 10C shows the heating blocks unclamping from the rotatable disc and the rotatable disc rotating to the second pair of heating blocks. A comparison of FIG. 10C to FIG. 10D illustrates the second pair of heating blocks clamping, or coming into contact with, the rotatable disc
Figure 10B:
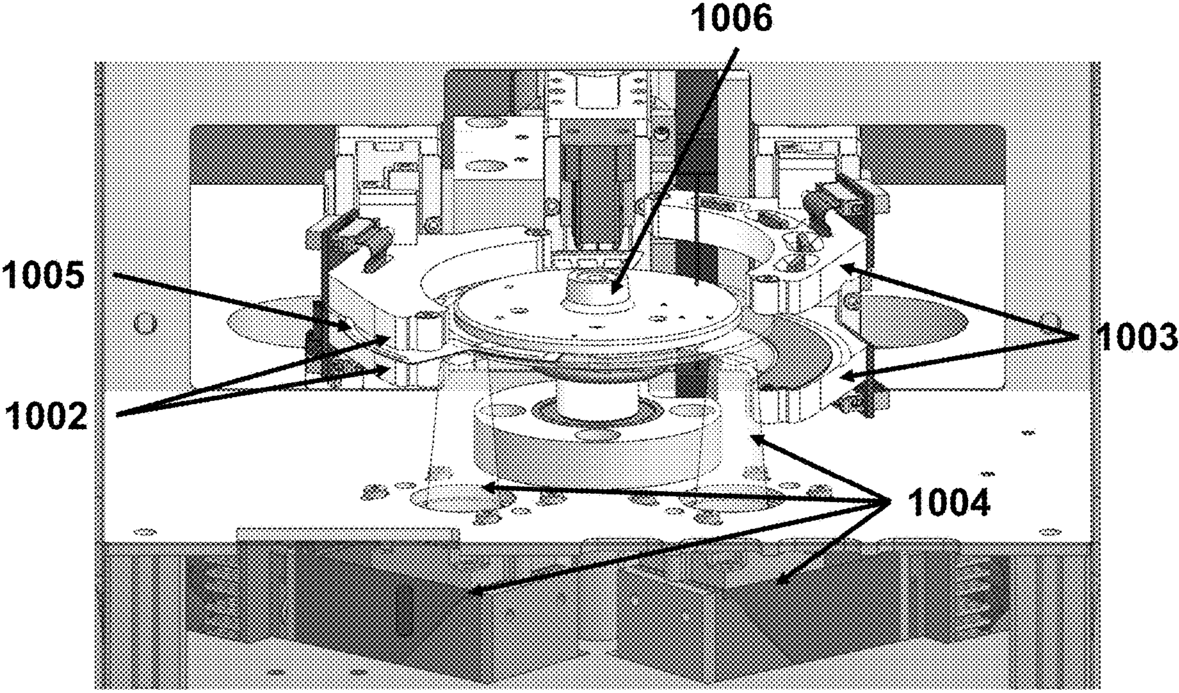

In some embodiments, each pair of heating blocks (e.g., the first heating block, the second heating block, or the third heating block) may come into contact with the reaction chamber or the plurality of reaction chambers from the top and the bottom (FIG. 10B 1005 and 1002). The pair of heating blocks may contact the reaction chamber or plurality of reaction chambers with a force of about 1 N to about 100 N. The pair of heating blocks may contact the reaction chamber or plurality of reaction chambers for a period of time from about 0.1 seconds to about 10 seconds, thereby allowing for a ramping and a dwelling time necessary for optimal PCR amplification.

In some embodiments, the reaction chambers (e.g., cuvettes) on the rotatable disc may be designed and manufactured to be filled and sealed before thermocycling. In some embodiments, the rotatable disc may comprise a cuvette insert, wherein the cuvette insert may comprise the reaction chambers (e.g., cuvettes). In some embodiments, the ultra-fast thermocycling of the present disclosure may be performed after the reaction chamber or the plurality of reaction chambers are solidly sealed from the atmosphere. The reaction chambers may, before sealing, be openly connected via microfluidic connections to an upper chamber. The reaction chambers may be filled via this microfluidic connection.

Figure 5A:
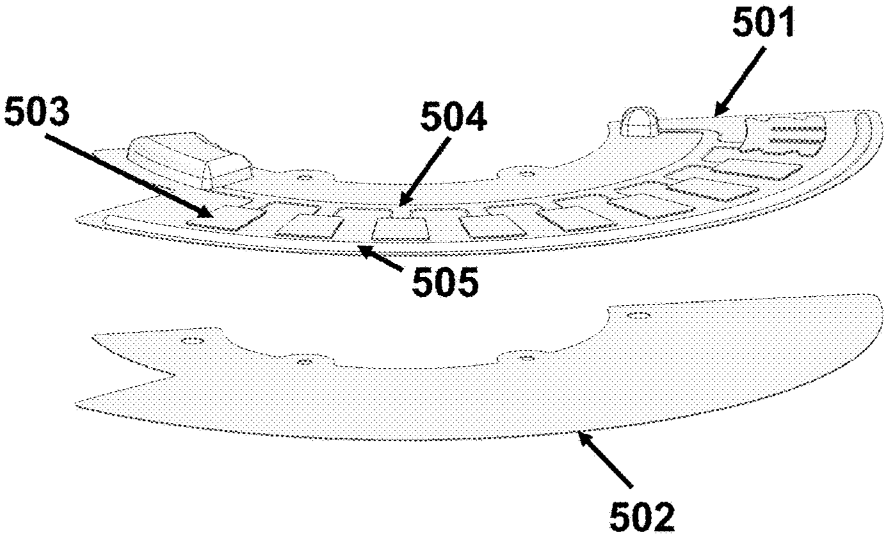
FIGS. 5A-5C illustrate multiple views of a rotatable disc described herein.
Figure 5B:
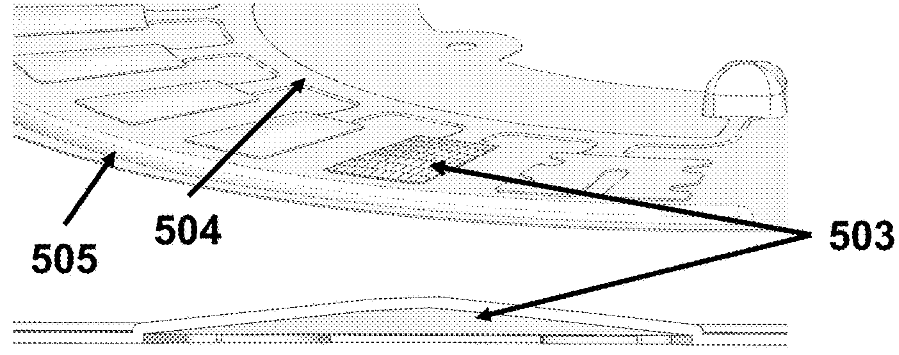

In some embodiments, the reaction chambers may be formed by sealing two thin polymer films together (FIG. 5A, FIG. 5B). For example, but not by way of limitation, one film (FIG. 5A 501) may be thermoformed to define reaction chamber shape and size (FIG. 5B 503) as well as a channel (FIG. 5B. 504). For example, but not by way of limitation, the second film may be a flat film (FIG. 5A 502), which may be used to laminate and seal the thermoformed film. In some embodiments, the thermoformed reaction chamber and channel have an aspect ratio of at least about 10 to 1. In some embodiments, the aspect ratio is at least about 20 to 1. In some embodiments, the depth of the reaction chamber is at most about 1 mm. In some embodiments, the depth of the reaction chamber is at most about 250 μm. In some embodiments, the depth of the channel is at most about 200 μm. In some embodiments, the depth of the channel is at most about 100 μm.

In some embodiments, the channel is formed by a thermoformed film. This thermoformed film can be heated in order to seal the channel. The channel can be heat sealed by compressing the thermoformed film composing the ceiling of the channel against the sealing film composing the floor of the channel. In some embodiments, the thermoformed film comprises a thickness from about 50 μm to about 500 μm. In some embodiments, the thermoformed film comprises a thickness from about 100 μm to about 300 μm. In some embodiments, the channel comprises a width from about 1 mm to about 5 mm. In some embodiments, the channel comprises a width from about 0.05 mm to about 5 mm. In some embodiments, the channel comprises a width from about 2 mm to about 4 mm. In some embodiments, the channel comprises a width from about 0.25 mm to about 4 mm. In some embodiments, the width of channel divided by the thickness of thermoformed film is above 2, thereby allowing the channel to be readily compressed to obtain a strong heat seal and completely close the channel.

In some embodiments, the sealing film comprises a thickness from about 10 μm to about 500 μm. In some embodiments, the sealing film comprises a thickness from about 40 μm to about 100 μm. In some embodiments, the sealing film and thermoformed film comprise a thermoplastic resin. In some embodiments, the sealing film and the thermoformed film comprise the same thermoplastic resin. In some other embodiments, the sealing film and thermoformed film comprise a thermoplastic resin that can be heat sealed together. In some embodiments, the sealing film or thermoformed film comprise a single polymer. In some embodiments, the sealing film or thermoformed film are coextruded and comprise a thermoplastic resin further comprising an inner layer polymer having a lower glass transition temperature (Tg) than the outer layer polymer. In some embodiments, the resin is selected from polyolefin, polycarbonate, polystyrene, PMMA, polyethylene, and polypropylene.

In one aspect of the present disclosure, three heating blocks (e.g., a first heating block (FIG. 1 104), a second heating block (FIG. 1 105), and a third heating block (FIG. 1 104)) are set to three different temperatures (e.g., a first temperature, a second temperature, and a third temperature) corresponding to a denaturation temperature (e.g., about 90° C. to about 99° C.), an annealing temperature (e.g., about 50° C. to about 70° C.), and an elongation temperature (e.g., about 70° C. to about 75° C.). In some embodiments, the three heating blocks comprise a radial length, wherein the radial lengths are designed to correspond to a ratio of time favorable for denaturation, annealing, and elongation steps. The analytical device may thereby perform the PCR amplification process while the rotatable disc rotates at a constant speed above the fixed heating blocks, and may keep physical contact with the block during the entire process. In some embodiments, the disclosure comprises two heating blocks (e.g., a first heating block (FIG. 7 704) and a second heating block (FIG. 7 705)) set at two different temperatures (e.g., a first temperature and a second temperature) corresponding to a denaturation temperature (e.g., about 90° C. to about 99° C.) and an annealing/elongation temperature (e.g., about 50° C. to about 75° C.). In this embodiment, the analytical device may thereby perform the annealing and elongation PCR steps with the same heating block at the same temperature.

In some embodiments, the first heating block, set at a denaturing temperature (e.g., a first temperature), comprises a radial length (e.g., a first radial length) designed to translate to a contact time of about 500 ms to about 2 sec for each reaction chamber moving above the first heating block, while the rotatable disc rotates at a speed of about 4 RPM to about 16 RPM. In some embodiments, the second heating block, set at the annealing temperature (e.g., a second temperature), comprises a radial length (e.g., a second radial length) of about 6 to about 7 times the radial length of the first heating block. In some embodiments, the second heating block, set at the annealing/elongation temperature (e.g., a second temperature), comprises a radial length (e.g., a second radial length) of about 8 to about 9 times the radial length of the first heating block. In some embodiments, the third heating block, set at the elongation temperature (e.g., a third temperature) comprises a radial length of about 2 to about 3 times of the radial length of the first heating block.

In some embodiments, the heating blocks (e.g., a first heating block, a second heating block, or a third heating block) comprise a material having a low friction coefficient (e.g., Teflon or Boron Aluminum Magnesium). For example, and not by way of limitation, the heating blocks may be constituted or coated with a material having a low friction coefficient. In some embodiments, contact between the rotatable disc and the heating block allows fast heat transfer to the reaction chambers. In some embodiments, contact between the rotatable disc and the heating block allows the rotatable disc to rotate at a constant speed. In some embodiments, the speed of the rotatable disc is from about 4 RPM to about 16 RPM.

In some embodiments, the heating blocks (e.g., a first heating block, a second heating block, or a third heating block) comprise one heating block, wherein the rotatable disc is located above the heating block. In some other embodiments, the heating blocks comprise one heating block, wherein the rotatable disc is located below the heating block. In some other embodiments, the heating blocks comprise a pair of heating blocks (FIG. 10A, 1002; FIG. 10A 1003), mirrored from the rotatable disc plane, which sandwich the rotatable disc (FIG. 10A, 1005).

Figure 10C:
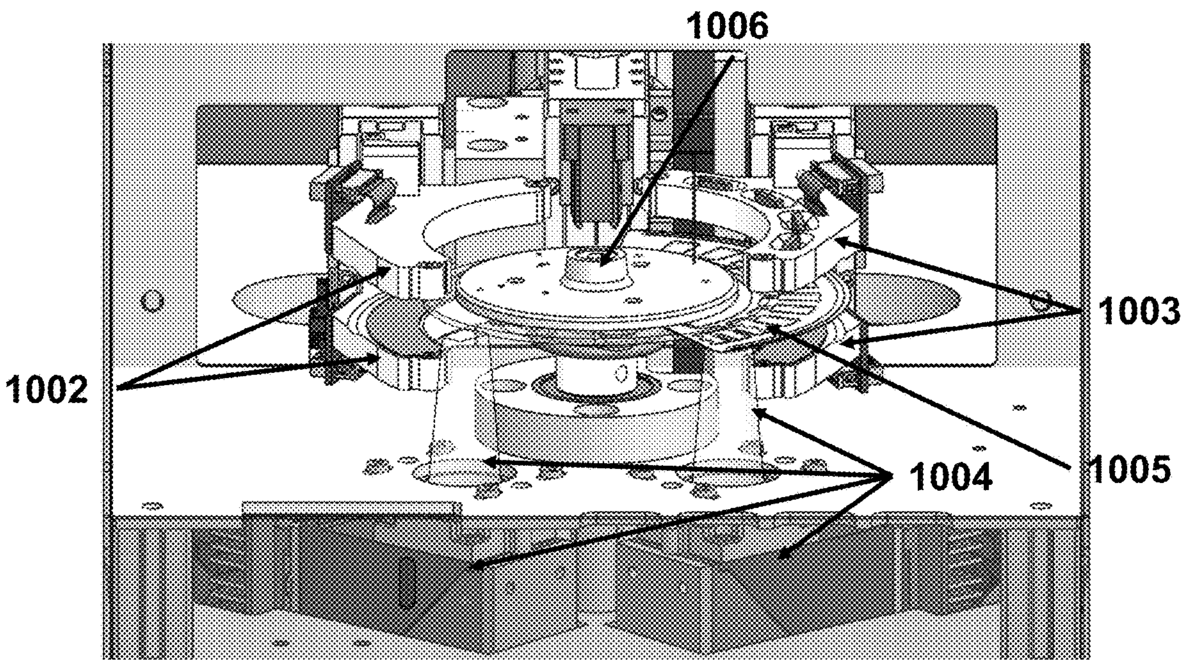
Figure 10D:
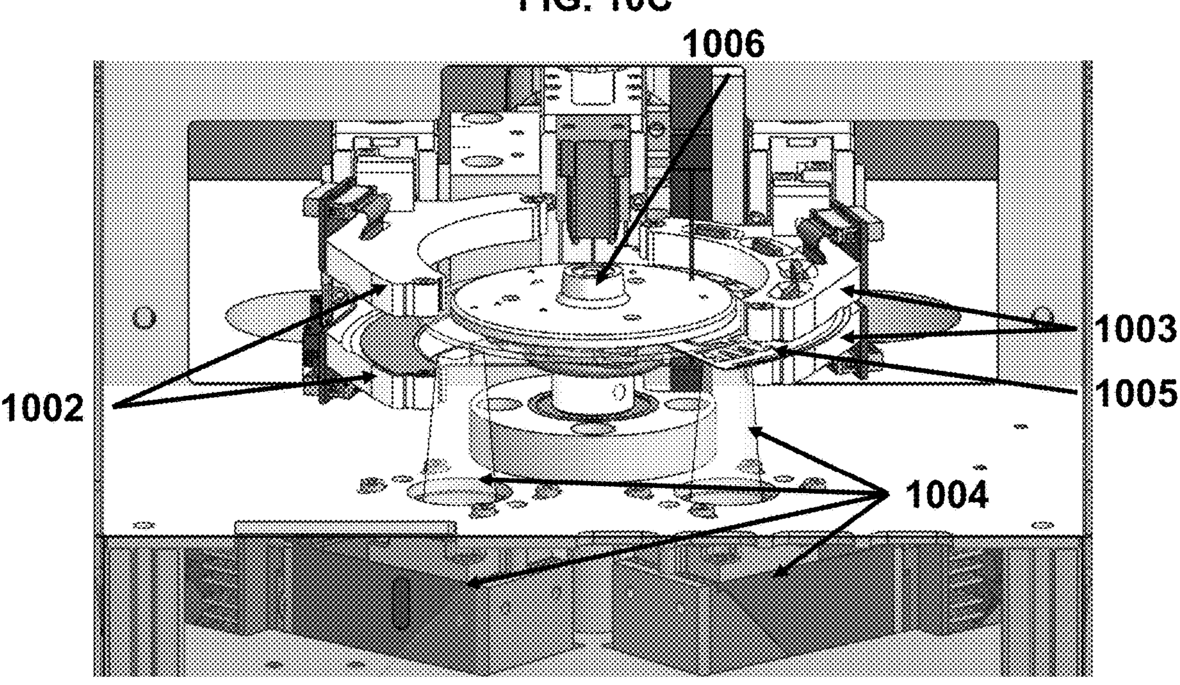
Figure 11A:
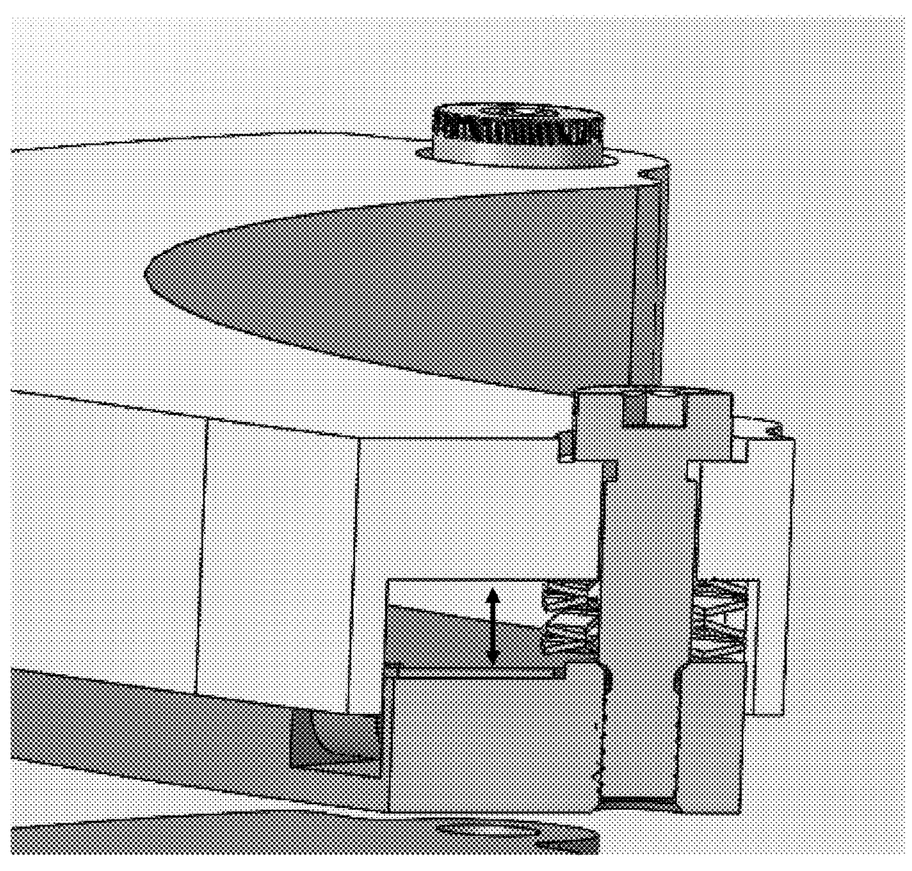
FIGS. 11A-11B illustrate zoom-in views of a heating element of the analytical device provided herein.
Figure 11B:
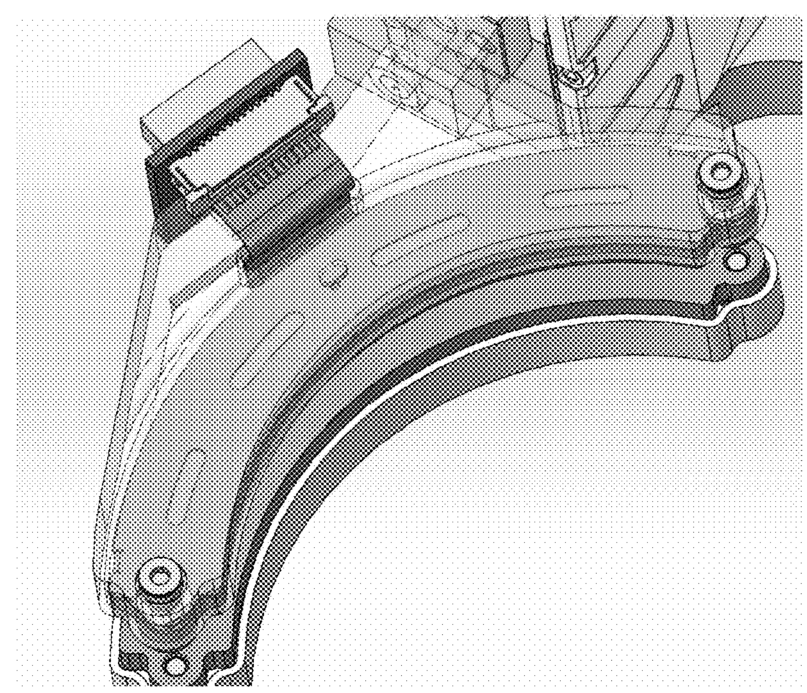

In some embodiments, the rotatable disc is maintained at each heating block where the bottom and top block are mechanically placed in contact with the rotatable disc. For example, the disc can be clamped between the pair of heating blocks, as shown by comparison of element 1002 in FIG. 10A and FIG. 10B. In some embodiments, the rotatable disc moves from one heating block to another heating block after the rotatable disc is mechanically un-clamped from the heating block, as shown by comparison of element 1005 in FIG. 10A and FIG. 10C.

In some embodiments, the analytical device further comprises an optic head (FIG. 1, 107; FIG. 7, 706, FIG. 8A, 804) that excites and detects fluorescence inside the reaction chambers while in rotation. In some embodiments, an excitation source and a detector are on the same side of the rotatable disc. In some embodiments, an excitation source and detector are placed on opposing sides of the rotatable disc. In some embodiments, the excitation source is a light source encompassing the wavelength of the fluorophore of interest (e.g., LASER or LED). In some embodiments, the fluorophore of interest is selected from FAM (e.g., 495 nm/520 nm), SUN (e.g., 538 nm/554 nm), TEX 615 (e.g., 596 nm/613 nm), or Cy5 (e.g., 648 nm/667 nm).

In some embodiments, the rotatable disc comprises a reaction chamber (e.g., cuvette) or a plurality of reaction chambers (e.g., cuvettes) as shown by element 209 in FIG.

Figure 2:
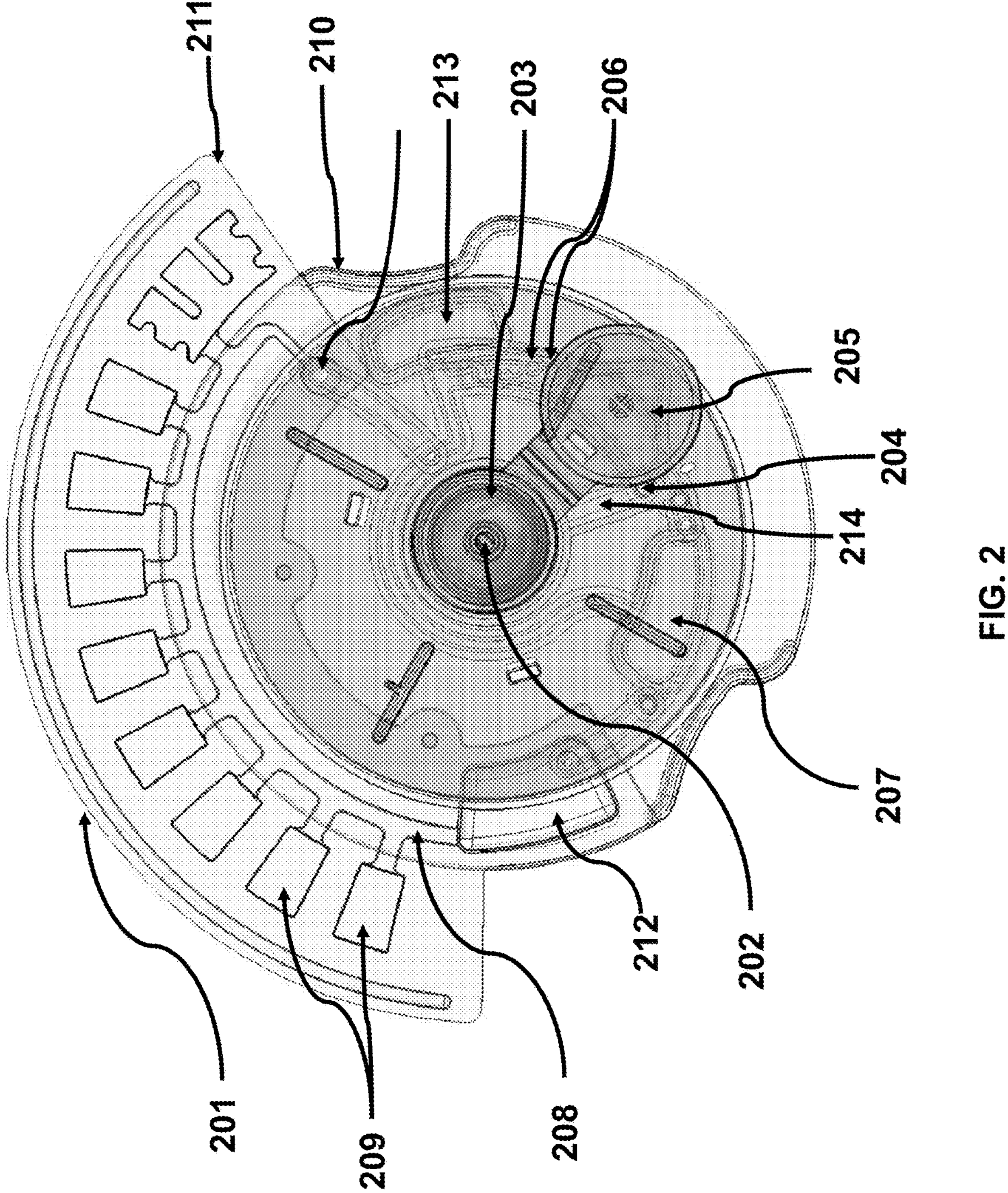
FIG. 2 illustrates a top view of a rotatable disc described herein.

2. In some embodiments, the rotatable disc comprises a cuvette insert 211 comprising the plurality of reaction chambers 209. In some embodiments, the reaction chambers (e.g., cuvettes) are located at the edge of the rotatable disc (FIG. 2, 201). In some embodiments, the plurality of reaction chambers comprises from one to about 100 reaction chambers. In some embodiments, the plurality of reaction chambers comprises from about 4 to about 10 reaction chambers. In one example, but not by way means of limitation, there may be 8 reaction chambers equally spaced from each other. In some embodiments, the plurality of reaction chambers are equally spread over 360 degrees of the rotatable disc. In some embodiments, the plurality of reaction chambers (e.g., cuvettes) occupies a section of the rotatable disc, e.g., from about 10 degrees of arc to about 100 degrees of arc.

In some embodiments, each of the plurality of reaction chambers (FIG. 2, 209) is connected to an upstream mixing chamber (FIG. 2, 207) and to the adjacent reaction chamber (FIG. 2, 209) via a channel (FIG. 2, 208). In some embodiments, the channel comprises a thin plastic film (e.g., a sealing film) sealed on the rotatable disc. In some embodiments, the thin plastic film (e.g., the sealing film) is in direct contact with the material of the rotatable disc (e.g., hard plastic disc). For example, but not by way of limitation, the channel may not have any depth, and a sample liquid may be forced through by applying a high centripetal force to the rotatable disc. In some embodiments, the thin plastic film (e.g., sealing film or thermoplastic material) comprises a material (e.g., a resin) selected from polycarbonate, polypropylene, PEET, and COC. In some embodiments, the thin plastic film (e.g., sealing film or thermoplastic material) comprises a material (e.g., a resin) with a Tg of at least about 100° C. In some embodiments, the thin film (e.g., a sealing film) comprises a thickness from about 10 μm to about 400 μm. In some embodiments, the rotatable disc comprises a thermoplastic (e.g., a thermoformed film) with a Tg of at least about 100° C. In some embodiments, the rotatable disc comprises the thermoplastic (e.g., a thermoformed film) polycarbonate. In some embodiments, sealing of the channel is achieved via heat and pressure, via LASER welding or via ultrasonic welding. In some embodiments, sealing of the channel is achieved via heat and pressure, such as, but not limited to, by a heat sealer.

In some embodiments, each of the plurality of reaction chambers (e.g., cuvettes) has a volume capacity from about 10 μl to about 100 μl. In some embodiments, each of the plurality of reaction chambers has a depth of about 0.1 mm to about 1 mm. In some embodiments, each of the plurality of reaction chambers has a depth of about 0.2 mm to about 0.7 mm.

In some embodiments, the rotatable disc comprises different chambers (e.g., a loading chamber FIG. 2, 203, also referred to as a heating chamber herein; a metering chamber FIG. 2, 205; or a mixing chamber, FIG. 2, 207) linked by a channel (e.g., a channel comprising fluidic canals) (FIG. 1, 102) to accomplish metering and PCR reagent mixing after sample heating (e.g., hyperbaric heating). In some embodiments, and not by way of limitation, after extraction, nucleic acids may be brought to the plurality of reaction chambers (e.g., cuvettes) (FIG. 1, 103; FIG. 2, 209) via the channel (FIG. 1, 108; FIG. 2, 208). In some embodiments, the RT-PCR reagents are stored in the mixing chamber in a lyophilized form. Samples may be treated via heating in the loading chamber 203, metered into metering chamber 205, mixed with PCR lyophilized reagent inside chamber 207, and then flowed to the reaction chambers (e.g., cuvettes) 209 via channel 208. In some embodiments, the PCR primers and fluorescent probes are stored in the plurality of reaction chambers 209 in a dried format and are reconstituted when a solution containing the nucleic acid of interest is forced through the channel and fills the plurality of reaction chambers (e.g., cuvettes).

Figure 9A:
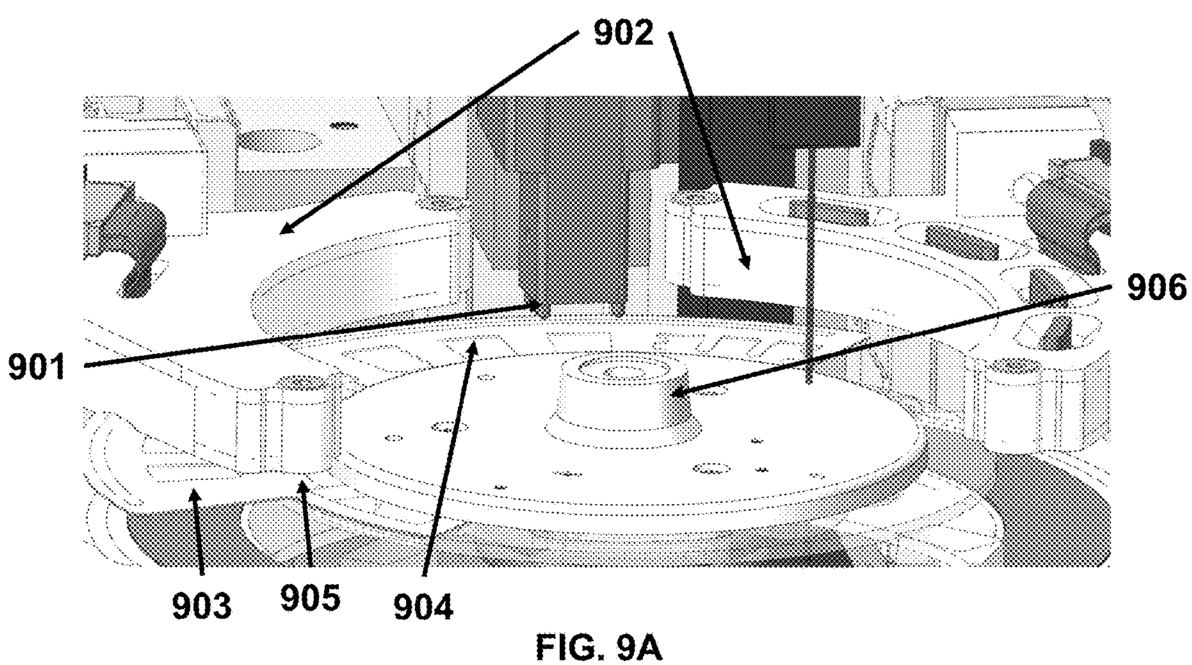
FIGS. 9A-9D illustrate a cartoon schematic of an analytical device for processing a target nucleic acid showing a heat sealer element for sealing a channel on a rotatable disc.
Figure 9B:
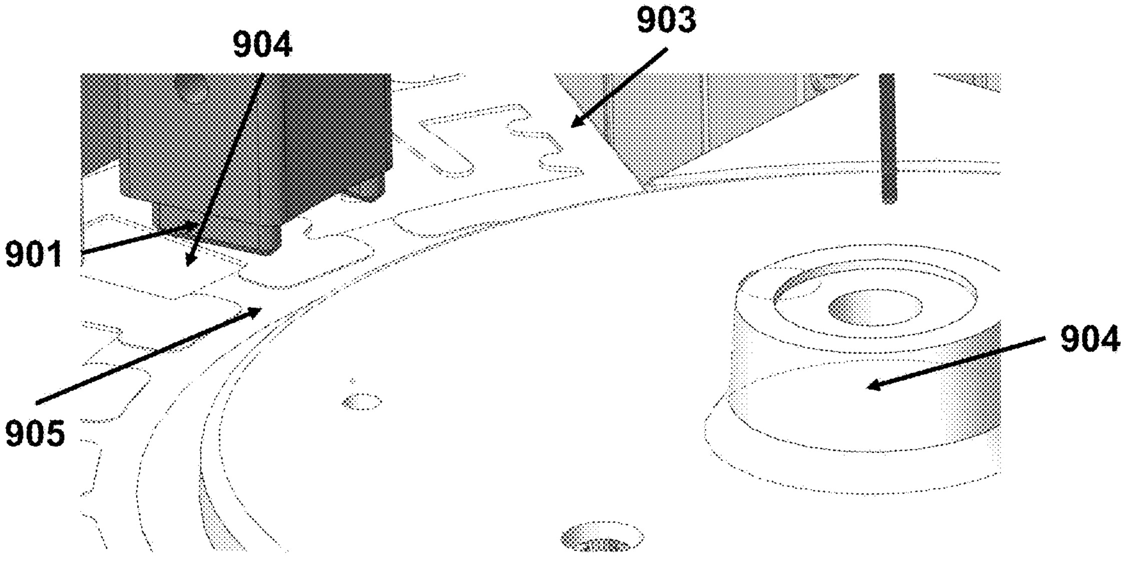
Figure 9C:
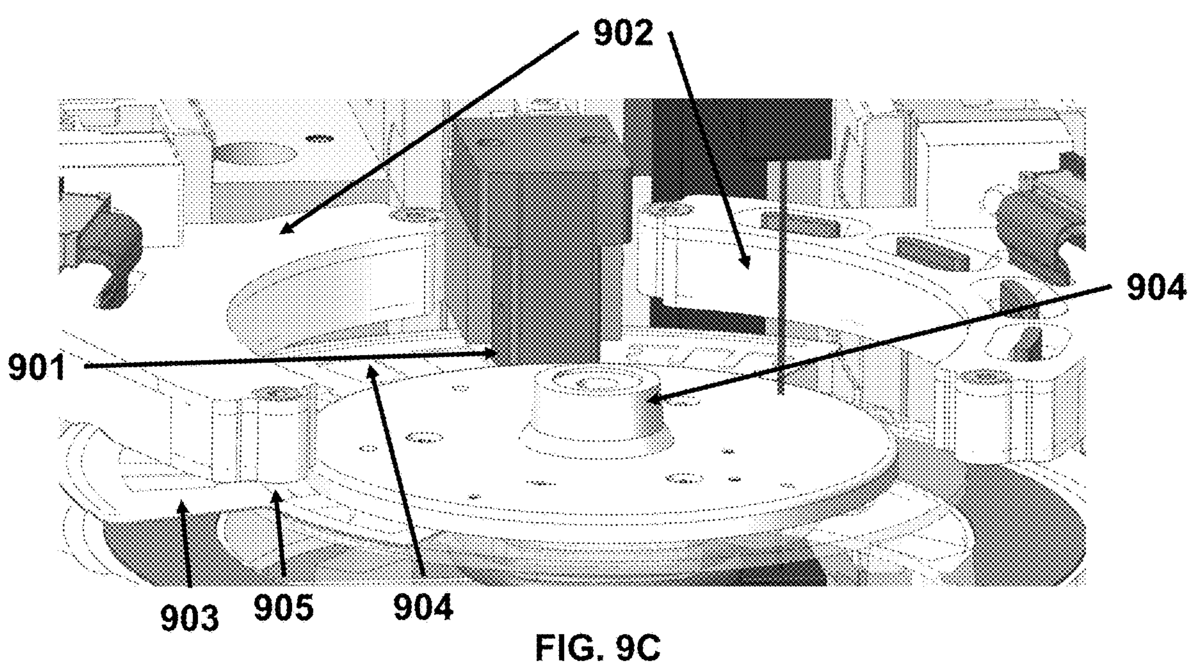
Figure 9D:
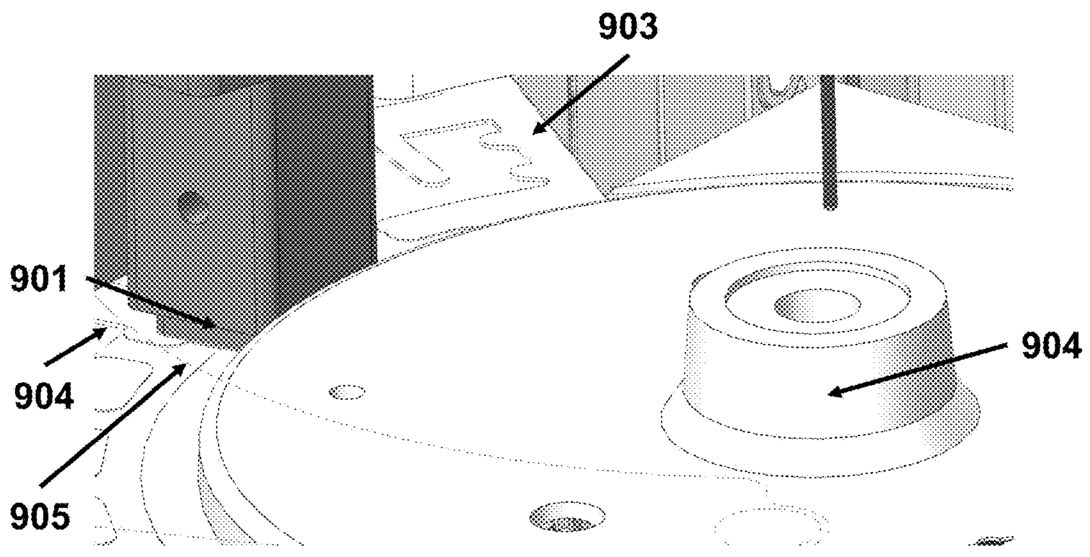

In some embodiments, the channel is sealed between each of the plurality of reaction chambers after filling each reaction chamber with liquid, thereby preventing evaporation and escape of liquid when the reaction chambers are heated to a high temperature. In some embodiments, the channel is sealed with an electromagnetic source, such as but not limited to a LASER light mounted on a trail. In some embodiments, the channel is sealed by applying pressure and heat to the channel by, for example, a heat sealer (FIG. 9B, 901 to FIG. 9D, 901). In some aspects, the present disclosure relates to a method wherein the analytical device described herein is used to rapidly temperature cycle a volume of about 10 to about 100 μl of PCR or RT-PCR reagents in each reaction chamber. In the method described herein, at most about 6 fluorophores per reaction chamber may be monitored simultaneously. In some embodiments, the method comprises filling the reaction chambers with PCR or RT-PCR reagents via the channel using centripetal force generated by rotating the rotatable disc. In some embodiments, the reaction chambers are filled by spinning the rotatable disc at from about 1,000 RPM to about 15,000 RPM. In some embodiments, after the reaction chambers are filled, the method further comprises sealing the reaction chambers by applying a heat source across the channel. In some embodiments, the heat source can be applied by contact or via an electromagnetic source, such as but not limited to, a LASER. In some embodiments, the sealing film is sealed to the thermoformed film across the channel by pressing two vis a vis blocks against the rotatable disc; see comparison between element 901 of FIG. 9B to FIG. 9D. In some embodiments, a LASER mounted on a trail seals the channel via a window between heating blocks.

In some embodiments, the analytical device further comprises a heating chamber for sample preparation of a nucleic acid containing sample prior to processing and analysis by PCR. In some embodiments, the heating chamber is a part of or connected to the rotatable disc comprising the reaction chambers. In some embodiments, the heating chamber is connected to a microfluidics network that can transfer a heat-treated sample to a mixing chamber, wherein the heat-treated sample can be mixed with PCR reagents, and further transferred to one or more reaction chambers wherein the nucleic acid amplification reactions are performed.

The methods and compositions provided herein can achieve fast nucleic acid amplification. For example, in some cases, the time period from loading a sample to obtaining a signal output indicating presence or absence of a target can be equal to or less than about 15 min, less than about 14 min, less than about 13 min, less than about 12 min, less than about 11 min, less than about 10 min, less than about 9 min, less than about 8 min, less than about 7 min, less than about 6 min, less than about 5 min, less than about 4 min, or less than about 3 min.

Methods for Sample Heating or Sample Preparation

The present disclosure provides methods for sample preparation for application to biological samples comprising a nucleic acid. Examples of biological samples comprising a nucleic acid may be bodily samples (e.g., saliva or mucus) or cells (e.g., a bacterial cell, a fungal cell, or a mammalian cell). The present disclosure provides methods for sample preparation of a nucleic acid in a bodily sample that do not involve extraction, isolation, or other forms of purification of the nucleic acid from the bodily sample. The present disclosure provides methods of heating a nucleic acid sample in hyperbaric heating conditions, thereby preparing it for further processing or analysis. In some embodiments, the heat-treated sample may undergo further sample processing or analysis. The present disclosure provides methods of inactivating molecular amplification inhibitors in the sample (e.g., RNAses present in saliva or mucus), thereby preparing the sample for further processing. The heat-treated sample or inactivated sample may be used for nucleic acid detection and/or analysis using PCR analysis or a biological (e.g., diagnostic) assay or any of the nucleic acid analysis methods disclosed elsewhere herein.

The present disclosure further provides methods of analyzing the nucleic acid in the biological sample, comprising preparing the sample using a method of the present disclosure and subsequently analyzing the nucleic acid. The methods of sample preparation described herein may prepare the sample for molecular amplification of the nucleic acid in the sample. In some embodiments, the methods described herein may improve the efficiency of nucleic acid analysis by improving the efficiency of molecular amplification. The methods described herein may reduce the degree of nucleic acid degradation and improve the detectability of the nucleic acid or molecular amplification products thereof for analysis.

Analyzing the nucleic acid can be performed using any number of techniques known in the art (for example, sequencing the nucleic acid (e.g., sequencing by synthesis, sequencing by hybridization, nanopore sequencing, etc.), genotyping the amino acid (e.g., genotyping by hybridization, genotyping by sequencing, etc.), or detecting the nucleic acid (e.g., detection by hybridization, antibody binding, fluorescence, radioisotope detection, etc.). For example, in some embodiments, detecting the nucleic acid comprises hybridizing the nucleic acid to a fluorescently-labeled nucleic acid comprising a sequence that is complementary to at least a portion of the nucleic acid using methods known in the art.

In some embodiments, analyzing the nucleic acid comprises one or more of the following: detecting the nucleic acid, sequencing the nucleic acid, and genotyping the nucleic acid. In some embodiments, analyzing the nucleic acid comprises detecting the nucleic acid. In some embodiments, analyzing the nucleic acid comprises sequencing the nucleic acid. In some embodiments, analyzing the nucleic acid comprises genotyping the nucleic acid.

In some embodiments, analyzing the nucleic acid comprises analyzing a molecular amplification product of the nucleic acid (e.g., DNA copies of RNA produced during PCR amplification of the RNA in the sample using reverse transcriptase). For example, in some embodiments, detecting the nucleic acid may comprise detecting a molecular amplification product of the nucleic acid. In some embodiments, sequencing the nucleic acid comprises sequencing a molecular amplification product of the nucleic acid. In some embodiments, genotyping the nucleic acid comprises genotyping a molecular amplification product of the nucleic acid. One of ordinary skill in the art will understand that many means for analyzing the nucleic acid are known in the art, all of which are compatible with methods of the present disclosure and contemplated herein.

In some embodiments, the molecular amplification comprises enzymatic amplification. In some embodiments, the molecular amplification comprises isothermal amplification. In some embodiments, the nucleic acid amplification comprises polymerase chain reaction ("PCR"), loop mediated isothermal amplification (LAMP), nucleic acid sequence based amplification (NASBA), self-sustained sequence replication (3 SR), strand displacement amplification (SDA), multiple displacement amplification (MDA), rolling cycle amplification (RCA), ligase chain reaction (LCR), helicase dependent amplification (HAD), ramification amplification method (RAM), transcription-mediated assay (TMA), Nicking enzyme amplification reaction (NEAR), Recombinase Polymerase Amplification (RPA), or whole genome amplification (WGA).

In some embodiments, the molecular amplification comprises polymerase chain reaction ("PCR"). In some embodiments, the PCR comprises reverse transcriptase-polymerase chain reaction (RT-PCR), reverse transcription-quantitative PCR (RT-qPCR), quantitative real-time PCR (qPCR), digital PCR (dPCR), digital droplet PCR (ddPCR), microfluidic PCR, multiplex PCR, variable number of tandem repeats (VNTR) PCR, asymmetric PCR, nested PCR, quantitative PCR, Hot-start PCR, touchdown PCR, assembly PCR, colony PCR, suicide PCR, co-amplification at lower denaturation temperature-PCR (COLD-PCR), rapid amplification of cDNA ends (RACE) PCR, two-tailed PCR, ligation-mediated PCR, methylation-specific PCR (MSP), InterSequence-Specific PCR (or ISSR-PCR), RNase H-dependent PCR (rhPCR), or Vectorette PCR.

In some embodiments, the nucleic acid can be analyzed after molecular amplification (e.g., PCR) of the nucleic acid. In some embodiments, the nucleic acid is analyzed as part of a downstream application. In some embodiments, the downstream application comprises molecular amplification or sequencing. In some embodiments, the downstream application comprises probe hybridization and/or detecting the probe.

In some aspects, the methods of the present disclosure comprise heating a treatment sample. A "treatment sample", as referred to herein, is a sample (e.g., an aqueous solution or suspension) containing at least a nucleic acid and optionally reagents such as enzymes or chelating agents. In certain embodiments, a treatment sample may be a biological sample of nucleic acids collected from a subject and diluted with water or a buffer and optionally including the one or more reagents. The biological sample may be a bodily sample, such as saliva or mucus. The biological sample may comprise a cell (e.g., an unlysed cell). In certain embodiments, the sample of nucleic acid collected from a subject may be isolated or purified, e.g., isolated or purified from the cell, proteins, or other biologics in the biological sample, prior to dilution and/or addition of reagents. In certain embodiments, the sample of nucleic acid collected from a subject may not be isolated or purified, e.g., isolated or purified from the cell, proteins, or other biologics in the biological sample, prior to dilution and/or addition of reagents.

In some aspects, the method comprises heating the treatment sample to a temperature above 100 degrees Celsius in a closed heating chamber in hyperbaric heating conditions. For instance, the closed heating chamber may substantially prevent air and vapor from entering or leaving the chamber. In some cases, there is negligible air flow in and out of the closed heating chamber. The closed heating chamber may remain closed during hyperbaric heating. In some embodiments, "hyperbaric heating conditions" referred to herein are conditions in which heating generates a higher pressure inside the closed heating chamber than outside the closed heating chamber. In some embodiments, the temperature referred to herein is each an average temperature for the duration of the sample heating step or a portion thereof. In some embodiments, the temperature referred to herein is the temperature inside the closed vessel. In some embodiments, the temperature referred to herein is the temperature of the heating device used to hyperbarically heat the sample. In some cases, the temperature is estimated using an internal temperature sensor inside the closed vessel. In some cases, the internal temperature is correlated via an external temperature infrared sensor assessing the exterior temperature of the closed vessel. In some aspects, the heating of the treatment sample occurs at a temperature ramp rate, for example, from 6 degrees Celsius per second to 20 degrees Celsius per second. In some aspects, the methods of the present disclosure comprise heating the treatment sample from a first temperature to a second temperature above 100 degrees over a ramp time.

In some aspects, the methods of the present disclosure comprise analyzing a nucleic acid in a bodily sample selected from: blood, lacrimal fluid, saliva, mucus, sputum, feces, cerebrospinal fluid, and urine. In one aspect, the method comprises providing the bodily sample and heating a treatment sample comprising the bodily sample. In some embodiments, the nucleic acid is not extracted, isolated, or otherwise purified from the bodily sample.

In some aspects, the methods of the present disclosure comprise heating a treatment sample comprising an unlysed cell comprising a nucleic acid, thereby producing a heat-treated sample. In some embodiments, the method further comprises analyzing the nucleic acid. In some embodiments, the nucleic acid is not extracted, isolated, or otherwise purified from the heat-treated sample prior to analyzing the nucleic acid.

In some aspects, the treatment sample comprising the nucleic acid further comprises one or more reagents selected from: a chelating agent, a single stranded nucleic acid binding protein, and a reducing agent. In some embodiments, the treatment sample comprises a chelating agent, a single stranded nucleic acid binding protein, and a reducing agent.

In some aspects, the present disclosure provides a method of inactivating a molecular amplification inhibitor in a treatment sample comprising a nucleic acid. In some aspects, the method comprises heating a treatment sample comprising i) a nucleic acid and ii) a plurality of molecular amplification inhibitors. In one aspect, the method comprises heating the treatment sample in a closed heating chamber to a temperature above 100 degrees Celsius in hyperbaric heating conditions, thereby inactivating a molecular amplification inhibitor of the plurality of amplification inhibitors and producing a heat-treated sample. In another aspect, the method comprises heating the treatment sample in a closed heating chamber in hyperbaric heating conditions from a first temperature to a second temperature over a ramp time above 100 degrees Celsius, thereby inactivating a molecular amplification inhibitor of said plurality of amplification inhibitors and producing a heat-treated sample, wherein the nucleic acid is not substantially degraded. In some embodiments, the method further comprises detecting the nucleic acid.

In some aspects, the methods described herein comprise heating a treatment sample in a closed heating chamber in hyperbaric conditions to a temperature above 100 degrees Celsius. In some embodiments, the method comprises hyperbaric heating the treatment sample to a temperature above 100 degrees Celsius. The temperature may be above the boiling point of water. In some embodiments, the treatment sample does not boil in the hyperbaric conditions at the temperature above 100 degrees. In some embodiments, the method comprises hyperbaric heating the treatment sample to a temperature from 100 degrees Celsius to 160 degrees Celsius. In some embodiments, the temperature is from 101 degrees Celsius to 160 degrees Celsius. In some embodiments, the temperature is from 105 degrees Celsius to 160 degrees Celsius. In some embodiments, the temperature is from 110 degrees Celsius to 160 degrees Celsius. In some embodiments, the temperature is from 120 degrees Celsius to 160 degrees Celsius. In some embodiments, the temperature is from 130 degrees Celsius to 160 degrees Celsius. In some embodiments, the temperature is from 140 degrees Celsius to 160 degrees Celsius. In some embodiments, the temperature is from 150 degrees Celsius to 160 degrees Celsius. In some embodiments, the temperature is from 100 degrees Celsius to 140 degrees Celsius. In some embodiments, the temperature is from 110 degrees Celsius to 140 degrees Celsius. In some embodiments, the temperature is from 120 degrees Celsius to 140 degrees Celsius. In some embodiments, the temperature is from 130 degrees Celsius to 140 degrees Celsius. In some embodiments, the temperature is about 110 degrees Celsius. In some embodiments, the temperature is about 120 degrees Celsius. In some embodiments, the temperature is about 130 degrees Celsius. In some embodiments, the temperature is about 140 degrees Celsius. In some embodiments, the temperature is about 150 degrees Celsius. In some embodiments, the temperature is about 160 degrees Celsius.

In some aspects, the heating of the treatment sample happens for a first time period. In some embodiments, the first time period is, for example, about 10 seconds, about 20 seconds, 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, 190 seconds, 200 seconds or 300 seconds. In some embodiments, the first time period is, for example, from 1 second to 300 seconds, 5 seconds to 300 seconds, 30 seconds to 300 seconds, from 40 seconds to 300 seconds, from 50 seconds to 300 seconds, from 60 seconds to 300 seconds, from 70 seconds to 300 seconds, from 80 seconds to 300 seconds, from 90 seconds to 300 seconds, from 100 seconds to 300 seconds, from 110 seconds to 300 seconds, from 120 seconds to 300 seconds, or from 200 seconds to 300 seconds. In some embodiments, the first time period is, for example, from 10 seconds to 180 seconds, from 20 seconds to 180 seconds, from 30 seconds to 180 seconds, from 40 seconds to 180 seconds, from 50 seconds to 180 seconds, from 60 seconds to 180 seconds, from 70 seconds to 180 seconds, from 80 seconds to 180 seconds, from 90 seconds to 180 seconds, from 100 seconds to 180 seconds, from 110 seconds to 180 seconds, or from 120 seconds to 180 seconds. In some embodiments, the first time period is, for example, from 10 seconds to 120 seconds, from 20 seconds to 120 seconds, from 30 seconds to 120 seconds, from 40 seconds to 120 seconds, from 50 seconds to 120 seconds, from 60 seconds to 120 seconds, from 70 seconds to 120 seconds, from 80 seconds to 120 seconds, from 90 seconds to 120 seconds, from 100 seconds to 120 seconds, or from 110 seconds to 120 seconds. In some embodiments, the first time period is, for example, from 30 seconds to 90 seconds, from 40 seconds to 90 seconds, from 50 seconds to 90 seconds, from 60 seconds to 90 seconds, from 70 seconds to 90 seconds, or from 80 seconds to 90 seconds. In some embodiments, the first time period is, for example, from 10 seconds to 60 seconds, from 20 seconds to 60 seconds, 30 seconds to 60 seconds, from 40 seconds to 60 seconds, or from 50 seconds to 60 seconds.

In some embodiments, the first time period is, for example, about 1 minute, about 2 minutes, about 3 minutes, about 4 minutes, about 5 minutes, about 6 minutes, about 7 minutes, about 8 minutes, about 9 minutes, or about 10 minutes. In some embodiments, the first time period is, for example, from 1 minute to 2 minutes, from 1 minute to 3 minutes, from 1 minute to 4 minutes, from 1 minute to 5 minutes, from 1 minute to 6 minutes, from 1 minute to 7 minutes, from 1 minute to 8 minutes, from 1 minute to 9 minutes, or from 1 minute to 10 minutes. In some embodiments, the first time period is, for example, from 1 minute to 5 minutes, from 2 minutes to 5 minutes, from 3 minutes to 5 minutes, or from 4 minutes to 5 minutes.

In some aspects, the method further comprises, after heating the treatment sample to a temperature above 100 degrees Celsius, maintaining the treatment sample at the temperature for a maintenance time prior to a cooling time. In some embodiments, the maintenance time is from 0 seconds to 300 seconds, from 0 seconds to 250 seconds, from 0 second to 200 seconds, from 0 seconds to 150 seconds, from 0 seconds to 120 seconds, from 0 seconds to 100 seconds, from 0 seconds to 50 seconds, from 0 seconds to 40 seconds, from 0 seconds to 30 seconds, from 0 seconds to 20 seconds, or from 1 to 10 seconds. In some embodiments, the maintenance time is from 5 seconds to 300 seconds, from 5 seconds to 250 seconds, from 5 seconds to 200 seconds, from 5 seconds to 150 seconds, from 5 seconds to 100 seconds, from 5 seconds to 50 seconds, from 5 seconds to 40 seconds, from 5 seconds to 30 seconds, from 5 seconds to 20 seconds, or from 5 to 10 seconds.

During the maintenance time, the closed heating chamber may remain closed (e.g., substantially prevent air and vapor from entering or leaving the chamber).

In some embodiments, the cooling time is from 5 seconds to 300 seconds. In some embodiments, the cooling time is from 30 seconds to 300 seconds. In some embodiments, the cooling time is from 60 seconds to 300 seconds. In some embodiments, the cooling time is from 90 seconds to 300 seconds. In some embodiments, the cooling time is from 120 seconds to 300 seconds. In some embodiments, the cooling time is from 150 seconds to 300 seconds. In some embodiments, the cooling time is from 180 seconds to 300 seconds. In some embodiments, the cooling time is from 240 seconds to 300 seconds. In some embodiments, the cooling time is from 270 seconds to 300 seconds.

In some embodiments, the cooling time is from 10 seconds to 120 seconds. In some embodiments, the cooling time is from 30 seconds to 120 seconds. In some embodiments, the cooling time is from 60 seconds to 120 seconds. In some embodiments, the cooling time is from 90 seconds to 120 seconds. During the cooling time, the closed heating chamber may remain closed (e.g., substantially preventing air and vapor from entering or leaving the chamber). In some embodiments, the nucleic acid is not substantially degraded after heating.

In some aspects, heating the treatment sample comprising said nucleic acid occurs at a temperature ramp rate. In some embodiments, the temperature ramp rate is calculated as the time derivative of temperature. In some embodiments, the temperature ramp rate is calculated as the average rate of change of temperature with respect to time. In some embodiments, the temperature ramp rate is at least 0.5 degrees Celsius per second, at least 1 degrees Celsius per second, at least 2 degrees Celsius per second, at least 3 degrees Celsius per second, at least 4 degrees Celsius per second, at least 5 degrees Celsius per second, at least 6 degrees Celsius per second, at least 7 degrees Celsius per second, at least 8 degrees Celsius per second, at least 9 degrees Celsius per second, at least 10 degrees Celsius per second, at least 11 degrees Celsius per second, at least 12 degrees Celsius per second, at least 13 degrees Celsius per second, at least 14 degrees Celsius per second, at least 15 degrees Celsius per second, at least 16 degrees Celsius per second, at least 17 degrees Celsius per second, at least 18 degrees Celsius per second, at least 19 degrees Celsius per second, at least 20 degrees Celsius per second, at least 25 degrees Celsius per second, at least 27.5 degrees Celsius per second, at least 30 degrees Celsius per second, at least 32.5 degrees Celsius per second at least 35 degrees Celsius per second, at least 37.5 degrees Celsius per second, at least 40 degrees Celsius per second, at least 42.5 degrees Celsius per second, at least 45 degrees Celsius per second, at least 47.5 degrees Celsius per second, or at least 50 degrees Celsius per second.

In some embodiments, the temperature ramp rate is from 0.5 degrees Celsius per second to 50 degrees Celsius per second, from 0.5 degrees Celsius per second to 40 degrees Celsius per second, from 0.5 degrees Celsius per second to 35 degrees Celsius per second, from 0.5 degrees Celsius per second to 30 degrees Celsius per second, from 0.5 degrees Celsius per second to 25 degrees Celsius per second, from 0.5 degrees Celsius per second to 20 degrees Celsius per second, or from 0.5 degrees Celsius per second to 15 degrees Celsius per second.

In some embodiments, the temperature ramp rate is from 2 degrees Celsius per second to 50 degrees Celsius per second, from 2 degrees Celsius per second to 40 degrees Celsius per second, from 2 degrees Celsius per second to 35 degrees Celsius per second, from 2 degrees Celsius per second to 30 degrees Celsius per second, from 2 degrees Celsius per second to 25 degrees Celsius per second, from 2 degrees Celsius per second to 20 degrees Celsius per second, or from 2 degrees Celsius per second to 15 degrees Celsius per second.

In some embodiments, the temperature ramp rate is from 5 degrees Celsius per second to 50 degrees Celsius per second, from 5 degrees Celsius per second to 40 degrees Celsius per second, from 5 degrees Celsius per second to 35 degrees Celsius per second, from 5 degrees Celsius per second to 30 degrees Celsius per second, from 5 degrees Celsius per second to 25 degrees Celsius per second, from 5 degrees Celsius per second to 20 degrees Celsius per second, or from 5 degrees Celsius per second to 15 degrees Celsius per second. In some embodiments, the nucleic acid is not substantially degraded after heating.

In some aspects, the methods described herein comprise heating a treatment sample comprising said nucleic acid in a closed heating chamber in hyperbaric conditions from a first temperature to a second temperature above 100 degrees Celsius over a ramp time, thereby producing a heat-treated sample. The closed heating chamber may remain closed (e.g., substantially preventing air from entering or exiting the chamber) during heating from the first temperature to the second temperature. In some embodiments, the treatment sample does not boil in the hyperbaric conditions at the second temperature above 100 degrees. In some embodiments, the first temperature is from 4 degrees Celsius to 40 degrees Celsius and the second temperature is from 100 degrees Celsius to 160 degrees Celsius. In some embodiments, the first temperature is from 4 degrees Celsius to 40 degrees Celsius and the second temperature is from 101 degrees Celsius to 160 degrees Celsius. In some embodiments, the first temperature is from 4 degrees Celsius to 40 degrees Celsius and the second temperature is from 105 degrees Celsius to 160 degrees Celsius. In some embodiments, the first temperature is from 4 degrees Celsius to 40 degrees Celsius and the second temperature is from 110 degrees Celsius to 160 degrees Celsius. In some embodiments, the first temperature is from 4 degrees Celsius to 40 degrees Celsius and the second temperature is from 120 degrees Celsius to 160 degrees Celsius. In some embodiments, the first temperature is from 4 degrees Celsius to 40 degrees Celsius and the second temperature is from 130 degrees Celsius to 160 degrees Celsius. In some embodiments, the first temperature is from 4 degrees Celsius to 40 degrees Celsius and the second temperature is from 140 degrees Celsius to 160 degrees Celsius.

In some embodiments, the first temperature is from 20 degrees Celsius to 30 degrees Celsius and the second temperature is from 100 degrees Celsius to 160 degrees Celsius. In some embodiments, the first temperature is from 20 degrees Celsius to 30 degrees Celsius and the second temperature is from 101 degrees Celsius to 160 degrees Celsius. In some embodiments, the first temperature is from 20 degrees Celsius to 30 degrees Celsius and the second temperature is from 105 degrees Celsius to 160 degrees Celsius. In some embodiments, the first temperature is from 20 degrees Celsius to 30 degrees Celsius and the second temperature is from 110 degrees Celsius to 160 degrees Celsius. In some embodiments, the first temperature is from 20 degrees Celsius to 30 degrees Celsius and the second temperature is from 120 degrees Celsius to 160 degrees Celsius. In some embodiments, the first temperature is from 20 degrees Celsius to 30 degrees Celsius and the second temperature is from 130 degrees Celsius to 160 degrees Celsius. In some embodiments, the first temperature is from 20 degrees Celsius to 30 degrees Celsius and the second temperature is from 140 degrees Celsius to 160 degrees Celsius.

In some embodiments, the first temperature is from 4 degrees Celsius and 40 degrees Celsius and the second temperature is at least 100 degrees Celsius. In some embodiments, the first temperature is from 4 degrees Celsius and 40 degrees Celsius and the second temperature is at least 101 degrees Celsius. In some embodiments, the first temperature is from 4 degrees Celsius and 40 degrees Celsius and the second temperature is at least 105 degrees Celsius. In some embodiments, the first temperature is from 4 degrees Celsius and 40 degrees Celsius and the second temperature is at least 110 degrees Celsius. In some embodiments, the first temperature is from 4 degrees Celsius and 40 degrees Celsius and the second temperature is at least 120 degrees Celsius. In some embodiments, the first temperature is from 4 degrees Celsius and 40 degrees Celsius and the second temperature is at least 130 degrees Celsius. In some embodiments, the first temperature is from 4 degrees Celsius and 40 degrees and the second temperature is at least 140 degrees Celsius. In some embodiments, the first temperature is from 4 degrees Celsius and 40 degrees Celsius and the second temperature is at least 150 degrees Celsius. In some embodiments, the first temperature is from 4 degrees Celsius and 40 degrees Celsius and the second temperature is at least 160 degrees Celsius.

In some embodiments, the ramp time is from 3 to 100 seconds, from 6 to 100 seconds, from 7 to 100 seconds, from 8 to 100 seconds, from 9 to 100 seconds, or from 10 to 100 seconds. In some embodiments, the ramp time is from 3 to 50 seconds, from 6 to 50 seconds, from 7 to 50 seconds, from 8 to 50 seconds, from 9 to 50 seconds, or from 10 to 50 seconds.

In some embodiments, the method of analyzing the nucleic acid further comprises, after (a), maintaining said treatment sample at the second temperature for a maintenance time prior to a cooling time. In some embodiments, the maintenance time is from 0 seconds to 300 seconds. In some embodiments, the maintenance time is from 5 seconds to 300 seconds. In some embodiments, the maintenance time is from 30 seconds to 300 seconds. In some embodiments, the maintenance time is from 60 seconds to 300 seconds. In some embodiments, the maintenance time is from 90 seconds to 300 seconds. In some embodiments, the maintenance time is from 120 seconds to 300 seconds. In some embodiments, the maintenance time is from 150 seconds to 300 seconds. In some embodiments, the maintenance time is from 180 seconds to 300 seconds. In some embodiments, the maintenance time is from 240 seconds to 300 seconds. In some embodiments, the maintenance time is from 270 seconds to 300 seconds.

In some embodiments, the maintenance time is from 0 seconds to 120 seconds. In some embodiments, the maintenance time is from 10 seconds to 120 seconds. In some embodiments, the maintenance time is from 30 seconds to 120 seconds. In some embodiments, the maintenance time is from 60 seconds to 120 seconds. In some embodiments, the maintenance time is from 90 seconds to 120 seconds. During the maintenance time, the closed heating chamber may remain closed (e.g., substantially prevent air and vapor from entering or leaving the chamber).

In some embodiments, the cooling time is from 0 seconds to 300 seconds. In some embodiments, the cooling time is from 5 seconds to 300 seconds. In some embodiments, the cooling time is from 30 seconds to 300 seconds. In some embodiments, the cooling time is from 60 seconds to 300 seconds. In some embodiments, the cooling time is from 90 seconds to 300 seconds. In some embodiments, the cooling time is from 120 seconds to 300 seconds. In some embodiments, the cooling time is from 150 seconds to 300 seconds. In some embodiments, the cooling time is from 180 seconds to 300 seconds. In some embodiments, the cooling time is from 240 seconds to 300 seconds. In some embodiments, the cooling time is from 270 seconds to 300 seconds.

In some embodiments, the cooling time is from 10 seconds to 120 seconds. In some embodiments, the cooling time is from 30 seconds to 120 seconds. In some embodiments, the cooling time is from 60 seconds to 120 seconds. In some embodiments, the cooling time is from 90 seconds to 120 seconds. During the cooling time, the closed heating chamber may remain closed (e.g., substantially prevent air and vapor from entering or leaving the chamber).

In some aspects, heating the treatment sample in a closed chamber generates a pressure inside the chamber. In some embodiments, the pressure inside of the chamber is from, e.g., 1 to 200 PSI, 10 to 200 PSI, 20 to 200 PSI, 30 to 200 PSI, 40 to 200 PSI, 50 to 200 PSI, 10 to 100 PSI, 20 to 100 PSI, 30 to 100 PSI, 40 to 100 PSI, 50 to 100 PSI, 60 to 100 PSI, 70 to 100 PSI, 80 to 100 PSI, or 90 to 100 PSI, each of which is over 1 atm. In some embodiments, the pressure inside of the chamber is from, e.g., 10 to 100 PSI, 10 to 90 PSI, 10 to 80 PSI, 10 to 70 PSI, 10 to 60 PSI, 10 to 50 PSI, 10 to 40 PSI, 10 to 30 PSI, 10 to 20 PSI, 20 to 100 PSI, 20 to 90 PSI, 20 to 80 PSI, 20 to 70 PSI, 20 to 60 PSI, 20 to 50 PSI, 20 to 40 PSI, 20 to 30 PSI, 30 to 100 PSI, 30 to 90 PSI, 30 to 80 PSI, 30 to 70 PSI, 30 to 60 PSI, 30 to 50 PSI, or 30 to 40 PSI, each of which is over 1 atm. In some embodiments, the pressure inside the chamber is from 40 to 60 PSI over 1 atm. In some embodiments, the pressure inside the chamber is from 40 to 50 PSI over 1 atm. In some embodiments, the nucleic acid is not substantially degraded after heating.

Any means for heating the sample can be used, including but not limited to, contact heating in a dry heating block, induction heating, microwave heating, nanophotonic heating, or any other heating means known to the art. In some aspects, the treatment sample is heated with a heat source. In some embodiments, the heat source comprises an induction heater, a heating element, or a microwave. For example, in some embodiments, a heating block or heat bath can be used, e.g., by filling with pre-heated aluminum beads. In some embodiments, the heating of the biological sample is hyperbaric heating. In some embodiments, the treatment sample is hyperbarically heated with a heat source.

For example, in some embodiments, the treatment sample is heated using a heating block or heat bath is pre-heated at temperature ranging from 100 degrees Celsius to 300 degrees Celsius, or more preferably from 100 to 150 degrees Celsius where the hyperbaric heating vessel is placed on and leave for, e.g., 1 second to 10 minutes after reaching 100 degrees Celsius. In another embodiments, the vessel is hyperbarically heated for 20 to 40 seconds after reaching the temperature of 100 degrees Celsius or higher.

In another embodiment of the present disclosure, heat can be applied to the sample via induction heating. In some embodiments, the vessel can be made from a paramagnetic material or paramagnetic material can be placed directly in contact with the said sample inside the heating vessel made of non-paramagnetic heat resistant material such as plastic polymer. This provides an extreme temperature ramp rate enabling to bring the sample above 100 degrees Celsius in less than 30 seconds, which allow a complete sample preparation in one minute or less.

In some embodiments, a laser can be used to heat the treatment sample inside the vessel at temperature above 100 degrees Celsius (e.g., hyperbaric heating). Nanoparticles can be added to the heating system to capture laser energy and transduce it directly into the sample. This technique provides a very high heating ramp rate compatible with superheating sample preparation. In some embodiments, the heat source is a laser. In some embodiments, nanoparticles are added to the laser.

In some aspects, the present disclosure provides methods of heating a treatment sample comprising a nucleic acid. In some embodiments, the nucleic acid is DNA. In some embodiments, the nucleic acid is RNA. In some embodiments, the nucleic acid is derived from a eukaryotic cell or a prokaryotic cell. In some embodiments, the nucleic acid is derived from a virus. In some embodiments, the nucleic acid is selected from a viral nucleic acid, a bacterial nucleic acid, a protozoan nucleic acid, a eukaryotic nucleic acid, and a fungal nucleic acid. In some embodiments, the nucleic acid is a viral nucleic acid.

In some embodiments, the treatment sample comprising a bodily sample comprising the nucleic acid is heated in a closed heating chamber in hyperbaric conditions. In some embodiments, the bodily sample comprises a substance selected from blood, plasma, serum, lacrimal fluid, saliva, mucus, sputum, feces, cerebrospinal fluid, lymph fluid, bile, synovial fluid, cyst fluid, ascites, pleural fluid, ocular fluid, interstitial fluid, cervical fluid, and urine. In some embodiments, the bodily sample is selected from blood, lacrimal fluid, saliva, mucus, sputum, feces, cerebrospinal fluid, and urine. In some embodiments, the bodily sample comprises mucus. In some embodiments, the bodily sample comprises body fluid sample, tissue, or cell of a subject. In some embodiments, the nucleic acid is not extracted, isolated, or otherwise purified from the bodily sample.

In some aspects, the bodily sample may be collected from a subject (e.g., a human). The bodily sample may be collected via nasopharyngeal swab, cervical swab, or nasal swab from said subject. In some cases, the bodily sample may comprise a pathogen or a portion thereof. In some embodiments, the pathogen or portion thereof is selected from a virus or a portion thereof, a bacterium or a portion thereof, a protozoon or a portion thereof, a yeast or a portion thereof, and a fungus or a portion thereof. In some embodiments, the pathogen is a blood-borne pathogen or portion thereof. In some embodiments, the pathogen is a respiratory pathogen or portion thereof.

In some embodiments, the treatment sample comprising a bodily sample comprising the nucleic acid is heated in a closed heating chamber in hyperbaric conditions to a temperature above 100 degrees Celsius, thereby producing a heat-treated sample. In some aspects, the nucleic acid is analyzed after hyperbaric heating. In some cases, the nucleic acid is not extracted, isolated, or otherwise purified from said bodily sample. For example, in some cases, the nucleic acid is not extracted by phenol chloroform extraction or purified via a commercial nucleic acid purification kit or purified via column chromatography.

In some aspects, a treatment sample comprising a cell comprising the nucleic acid is heated in a closed heating chamber in hyperbaric conditions. The cell may be an unlysed cell. In some embodiments, the cell is embedded in a biological matrix such as nasal mucus, cerebrospinal fluid, feces, vaginal mucus, urine, or saliva. In some embodiments, the cell is embedded in nasal mucus. In some embodiments, the cell is a bacteria cell, e.g., *B. subtilis*, E. *Coli*, or S. *Pyogenes*. In some embodiments, the cell is a fungal cell, e.g., *C. albicans*. In some embodiments, the cell is a yeast cell, e.g., *S. cerevisiae*. In some embodiments, the cell is a mammalian cell, e.g., a Chinese hamster ovary cell, a BHK cell, or a murine C127 cell. In some embodiments, the cell is a human cell, e.g., a HeLa cell. In some embodiments, the treatment sample comprises a bacterial spore, e.g., *B. cereus* bacterial spore.

In some embodiments, the treatment sample comprising the unlysed cell comprising a nucleic acid is heated in a closed heating chamber in hyperbaric conditions to a temperature above 100 degrees Celsius, thereby producing a heat-treated sample. In some embodiments, the nucleic acid is analyzed after hyperbaric heating. In some cases, the nucleic acid is not extracted, isolated, or otherwise purified from the heat-treated sample prior to analyzing the nucleic acid.

In some aspects, the present disclosure provides a method of inactivating a molecular amplification inhibitor in a treatment sample comprising the nucleic acid. In some cases, the molecular amplification inhibitor may be an agent that binds to nucleic acid. The molecular amplification inhibitor may be an agent that degrades nucleic acid. In some cases, the molecular amplification inhibitor may be a nuclease. In some cases, the molecular amplification inhibitor is a DNase. In other cases, the molecular amplification inhibitor is an RNase.

In some aspects, the method comprises heating a treatment sample comprising i) a nucleic acid and ii) a plurality of molecular amplification inhibitors. In one aspect, the method comprises heating the treatment sample in a closed heating chamber to a temperature above 100 degrees Celsius in hyperbaric heating conditions, thereby inactivating a molecular amplification inhibitor of the plurality of amplification inhibitors and producing a heat-treated sample. In another aspect, the method comprises heating the treatment sample in a closed heating chamber in hyperbaric heating conditions from a first temperature to a second temperature over a ramp time above 100 degrees Celsius, thereby inactivating a molecular amplification inhibitor of said plurality of amplification inhibitors and producing a heat-treated sample, wherein the nucleic acid is not substantially degraded. In some embodiments, the nucleic acid is not more than, e.g., 20%, 15%, 12%, 11%, 10%, 9%, 8%, 7%, 6%, 5%, 4%, 3%, 2%, or 1% degraded. In some embodiments, the method further comprises amplifying the nucleic acid using molecular amplification. In some embodiments, the method further comprises detecting the nucleic acid.

In some aspects, the method inactivates at least one molecular amplification inhibitor in the treatment sample. In some embodiments, the method inactivates at least 60% of the plurality of molecular amplification inhibitors. In some embodiments, the method inactivates at least 70% of the plurality of molecular amplification inhibitors. In some embodiments, the method inactivates at least 80% of the plurality of molecular amplification inhibitors. In some embodiments, the method inactivates at least 90% of the plurality of molecular amplification inhibitors.

In some aspects, the nucleic acid is not substantially degraded after heating, such as hyperbaric heating. In some embodiments, the nucleic acid is, e.g., not more than 20%, not more than 15%, not more than 12%, not more than 11%, not more than 10%, not more than 9%, not more than 8%, not more than 7%, not more than 6%, not more than 5%, not more than 4%, not more than 3%, not more than 2%, or not more than 1% degraded after hyperbaric heating. In some embodiments, the nucleic acid is, e.g., at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, at least 99.5% intact after hyperbaric heating.

In some aspects, the nucleic acid is analyzed after hyperbaric heating. In some aspects, the method of analyzing the nucleic acid comprises amplifying the nucleic acid by molecular amplification (e.g., by a polymerase) after hyperbaric heating using any of the methods disclosed elsewhere herein. The molecular amplification may occur during real-time polymerase chain reaction (real-time PCR), transcription-mediated amplification (TMA), or loop-mediated isothermal amplification (LAMP). The molecular amplification of the nucleic acid may produce a molecular amplification product. In some embodiments, the method of analyzing the nucleic acid further comprises amplifying said nucleic acid by polymerase chain reaction (PCR) after heating, thereby producing a PCR product. In some embodiments, the method further comprises detecting the PCR product. In some cases, the PCR product is detected via a fluorescence signal emitted during amplification.

In some embodiments, the molecular amplification product (e.g., PCR product) is detectable following a lower number of molecular amplification cycles than would be required in the absence of hyperbaric heating of the treatment sample. In some embodiments, the molecular amplification product (e.g., PCR product) is detectable following a lower number of molecular amplification cycles than would be required as compared to heating the treatment sample at a temperature below 100 degrees Celsius. In some embodiments, the nucleic acid is detectable following a lower number of molecular amplification cycles than would be required as compared to heating the sample at a temperature below the boiling point of the sample for the same time.

In some embodiments, the molecular amplification product (e.g., PCR product) is detectable following from 10 to 50 molecular amplification cycles, from 15 to 50 molecular amplification cycles, from 20 to 50 molecular amplification cycles, from 25 to 50 molecular amplification cycles, from 26 to 50 molecular amplification cycles, from 27 to 50 molecular amplification cycles, from 28 to 50 molecular amplification cycles, from 29 to 50 molecular amplification cycles, or from 30 to 50 molecular amplification cycles.

In some embodiments, the molecular amplification product (e.g., PCR product) is detectable following from 10 to 40 molecular amplification cycles, from 20 to 40 molecular amplification cycles, from 25 to 40 molecular amplification cycles, from 26 to 40 molecular amplification cycles, from 27 to 40 molecular amplification cycles, from 28 to 40 molecular amplification cycles, from 29 to 40 molecular amplification cycles, or from 30 to 40 molecular amplification cycles.

In some embodiments, the molecular amplification product (e.g., PCR product) is detectable following from 10 to 35 molecular amplification cycles, from 20 to 35 molecular amplification cycles, from 25 to 35 molecular amplification cycles, from 26 to 35 molecular amplification cycles, from 27 to 35 molecular amplification cycles, from 28 to 35 molecular amplification cycles, from 29 to 35 molecular amplification cycles, or from 30 to 35 molecular amplification cycles. In some embodiments, the molecular amplification product (e.g., PCR product) is detectable following from 28 to 35 molecular amplification cycles. In some embodiments, the nucleic acid is detectable following, for example, from 25 to 35 molecular amplification cycles, from 25 to 34 molecular amplification cycles, from 25 to 33 molecular amplification cycles, from 25 to 32 molecular amplification cycles, from 25 to 31 molecular amplification cycles, from 25 to 30 molecular amplification cycles, from 25 to 29 molecular amplification cycles, or from 25 to 28 molecular amplification cycles.

In some embodiments, the molecular amplification product (e.g., PCR product) is detectable following 25 or more molecular amplification cycles. In some embodiments, the nucleic acid is detectable following, for example, 25 or more molecular amplification cycles, 26 or more molecular amplification cycles, 27 or more molecular amplification cycles, 28 or more molecular amplification cycles, 29 or more molecular amplification cycles, 30 or more molecular amplification cycles, 31 or more molecular amplification cycles, 32 or more molecular amplification cycles, 33 or more molecular amplification cycles, 34 or more molecular amplification cycles, or 35 or more molecular amplification cycles.

In some embodiments, the molecular amplification product (e.g., PCR product) is detected after the nucleic acid is amplified using from 10 to 40 molecular amplification cycles, from 10 to 35 molecular amplification cycles, from 20 to 35 molecular amplification cycles, from 25 to 35 molecular amplification cycles, from 26 to 35 molecular amplification cycles, from 27 to 35 molecular amplification cycles, from 28 to 35 molecular amplification cycles, from 29 to 35 molecular amplification cycles, or from 30 to 35 molecular amplification cycles.

In some embodiments, the detecting of the nucleic acid occurs simultaneously with the molecular amplification of the nucleic acid. In some embodiments, the detecting of the nucleic acid and the molecular amplification of the nucleic acid occur sequentially. In some embodiments, the detecting of the nucleic acid occurs after each cycle of molecular amplification.

In some embodiments, the method of analyzing the nucleic acid further comprises at least one of the following: detecting said nucleic acid, sequencing said nucleic acid, and genotyping said nucleic acid. In some embodiments, the method of analyzing the nucleic acid further comprises at least two of the following: detecting said nucleic acid, sequencing said nucleic acid, and genotyping said nucleic acid. In some embodiments, the method of analyzing the nucleic acid further comprises: detecting said nucleic acid, sequencing said nucleic acid, and genotyping said nucleic acid. In some embodiments, the method of analyzing the nucleic acid comprises detecting the nucleic acid via fluorescence detection.

As described herein, the treatment sample that is heated contains at least a nucleic acid and optionally reagents such as enzymes or chelating agents. In some embodiments, the nucleic acid is DNA. In some embodiments, the nucleic acid is RNA. In some embodiments, the nucleic acid is derived from a eukaryotic cell or a prokaryotic cell. In some embodiments, the nucleic acid is derived from a virus. In some embodiments, the nucleic acid is selected from a viral nucleic acid, a bacterial nucleic acid, a protozoan nucleic acid, a eukaryotic nucleic acid, and a fungal nucleic acid. In some embodiments, the nucleic acid is a viral nucleic acid.

In some embodiments, the nucleic acid is extracted from an organism selected from a prokaryote. In some embodiments, the nucleic acid is extracted from an organism selected from a eukaryote. In some embodiments, the nucleic acid is extracted from a parasite. In some embodiments, the nucleic acid is extracted from a virus, a bacterium, a fungus, an animal, or a plant.

In some embodiments, the nucleic acid is extracted from a virus. In some embodiments, the nucleic acid is extracted from a respiratory virus. In some embodiments, the virus is selected from an influenza virus, a rhinovirus, a coronavirus, a metapneumovirus, an adenoviruses, a syncytial virus, a bocaviruses, and a parainfluenza virus.

In some embodiments, the nucleic acid is extracted from a bacterium. In some embodiments, the nucleic acid is extracted from a gram-negative bacterium. In some embodiments, the nucleic acid is extracted from a gram-positive bacterium. In some embodiments, the nucleic acid is extracted from a fungus. In some embodiments, the nucleic acid is extracted from a yeast. In some embodiments, the nucleic acid is extracted from an animal. In some embodiments, the nucleic acid is extracted from a plant.

In some cases, the nucleic acid is in a bodily sample. In some embodiments, the nucleic acid is not extracted, isolated, or otherwise purified from the bodily sample. The bodily sample may be selected from blood, lacrimal fluid, saliva, mucus, sputum, feces, cerebrospinal fluid, and urine. In some embodiments, the bodily sample comprises a substance selected from blood, plasma, serum, lacrimal fluid, saliva, mucus, sputum, feces, cerebrospinal fluid, lymph fluid, bile, synovial fluid, cyst fluid, ascites, pleural fluid, ocular fluid, interstitial fluid, cervical fluid, and urine. In some embodiments, the bodily sample comprises mucus. In some embodiments, the bodily sample comprises body fluid sample, tissue, or cell of a subject.

In some aspects, the bodily sample may be collected from a subject. In some embodiments, the subject is a mammal. In some embodiments, the mammal is non-human primates (such as marmosets, macaques, chimpanzees), rodents (such as mouses, rats, gerbil jird, globefish Mouses, hamsters, cotton mouses, naked moles), rabbits, livestock mammals (such as goats, sheep, pigs, milk cows, ox, horses, camels), pet animals (such as dogs, cats), or zoo mammals. In some embodiments, the subject is a human.

The bodily sample may be collected via nasopharyngeal swab, cervical swab, or nasal swab from the subject. In some cases, the bodily sample may comprise a pathogen or a portion thereof. In some embodiments, the pathogen or portion thereof is selected from a virus or a portion thereof, a bacterium or a portion thereof, a protozoon or a portion thereof, a yeast or a portion thereof, and a fungus or a portion thereof. In some embodiments, the pathogen is a blood-borne pathogen or portion thereof. In some embodiments, the pathogen is a respiratory pathogen or portion thereof. In some embodiments, the respiratory pathogen comprises bacterial or fungal pathogens. In some embodiments, the respiratory pathogen is *Streptococcus pneumoniae, Haemophilus influenzae, Moraxella catarrhalis, Streptococcus pyogenes, Chlamydophila pneumoniae, Mycoplasma pneumoniae, Bordetella pertussis, Klebsiella pneumoniae, Staphylococcus aureus*, or *Aspergillus* sp. In some embodiments, the pathogen is a virus or a portion thereof. In some embodiments, the virus is respiratory virus. In some embodiments, the virus is SARS-CoV2, Influenza A viruses (-H1N1 and other subtypes), Influenza B virus, Human Respiratory Syncycial Virus (HRSV), Human Parainfluenza Viruses Type I (HPIV-1), II (HPIV-2), III (HPIV-3), IV (HPIV-4), Rhinovirus/Enterovirus (RV/EV), Adenoviruses (ADVs), HumanMetapneumovirus (hMPV), Human Coronavirus (HCoV)-229E, HCoV-HKU1, HCoV-NL63, or HCoV-OC43. In some embodiments, the virus is SARS-CoV2.

In some embodiments, the virus is selected from an influenza virus, a rhinovirus, a coronavirus, a metapneumovirus, an adenovirus, a syncytial virus, a bocavirus, and a parainfluenza virus. In some embodiments, the virus is an influenza virus. In some embodiments, the virus is a rhinovirus. In some embodiments, the virus is a coronavirus. In some embodiments, the virus is a metapneumovirus. In some embodiments, the virus is an adenovirus. In some embodiments, the virus is a syncytial virus. In some embodiments, the virus is a bocavirus. In some embodiments, the virus is a parainfluenza virus.

In some aspects, the treatment sample comprises the bodily sample and is heated in a closed heating chamber in hyperbaric conditions to a temperature above 100 degrees Celsius, thereby producing a heat-treated sample.

In some aspects, the treatment sample comprises a cell comprising the nucleic acid. The cell may be an unlysed cell. The cell may be a eukaryotic cell or a prokaryotic cell. In some embodiments, the cell is a bacteria cell, e.g., *B. subtilis, E. Coli*, or S. *Pyogenes*. In some embodiments, the cell is a fungal cell, e.g., *C. albicans*. In some embodiments, the cell is a yeast cell, e.g., *S. cerevisiae*. In some embodiments, the cell is a mammalian cell, e.g., a Chinese hamster ovary cell, a BHK cell, or a murine C127 cell. In some embodiments, the cell is a human cell, e.g., a HeLa cell. In some embodiments, the cell is a bacterial spore, e.g., *B. cereus* bacterial spore.

In some embodiments, the cell may be in a bodily sample. In some embodiments, the cell is embedded in a biological matrix such as nasal mucus, cerebrospinal fluid, feces, vaginal mucus, urine, or saliva. In some embodiments, the cell is embedded in nasal mucus.

The treatment sample may be an aqueous solution or suspension. In some embodiments, the treatment sample comprises isolated nucleic acid diluted in a collection buffer. In other embodiments, the treatment sample comprises a bodily sample (e.g., saliva or mucus) comprising a nucleic acid that is diluted in a collection buffer. In further embodiments, the treatment sample comprises an undiluted bodily sample comprising the nucleic acid. In some embodiments, the treatment sample comprises a cell that is suspended in a collection buffer. The collection solution or buffer in the present disclosure can be made of pure water, or can be a mix of a low buffer capacity buffer. An example of such buffer could be based on Tris HCl buffer ranging from 1 mM to 50 mM, with or without EDTA at a concentration ranging from 0.5 mM to 1 mM.

In some embodiments, the treatment sample comprises a pH of from about 8.0 to about 12.0. In some embodiments, the treatment sample comprises a pH of from about 9.0 to about 12.0. In some embodiments, the treatment sample comprises a pH of from about 10.0 to about 12.0. In some embodiments, the treatment sample comprises a pH of from about 11.0 to about 12.0. In some embodiments, the treatment sample comprises a pH of from about 8.0 to about 11.0. In some embodiments, the treatment sample comprises a pH of from about 9.0 to about 11.0. In some embodiments, the treatment sample comprises a pH of from about 10.0 to about 11.0. In some embodiments, the treatment sample comprises a pH of from about 8.0 to about 10.0. In some embodiments, the treatment sample comprises a pH of from about 9.0 to about 10.0.

In some embodiments, the treatment sample comprises a pH above 7.0. In some embodiments, the treatment sample comprises a pH above 8.0. In some embodiments, the treatment sample comprises a pH above 8.5. In some embodiments, the treatment sample comprises a pH above 9.0. In some embodiments, the treatment sample comprises a pH above 9.5. In some embodiments, the treatment sample comprises a pH above 10.0. In some embodiments, the treatment sample comprises a pH above 10.5. In some embodiments, the treatment sample comprises a pH above 11.0.

In some embodiments, the treatment sample comprises a pH about 7.0. In some embodiments, the treatment sample comprises a pH about 8.0. In some embodiments, the treatment sample comprises a pH about 9.0. In some embodiments, the treatment sample comprises a pH about 10.0. In some embodiments, the treatment sample comprises a pH about 11.0. In some embodiments, the treatment sample comprises a pH about 12.0.

In some embodiments, the treatment sample comprises a pH of from about 8.0 to 11.0. In some embodiments, the treatment sample comprises a pH of from about 9.0 to 11.0. In some embodiments, the treatment sample comprises a pH of from about 10.0 to 11.0.

In some embodiments, the treatment sample comprises a pH of from about 8.0 to 12.0. In some embodiments, the treatment sample comprises a pH of from about 9.0 to 12.0. In some embodiments, the treatment sample comprises a pH of from about 10.0 to 12.0. In some embodiments, the treatment sample comprises a pH of from about 11.0 to 12.0.

In some embodiments, the treatment sample comprises a pH of from about 4.0 to about 7.0. In some embodiments, the treatment sample comprises a pH of from about 5.0 to about 7.0. In some embodiments, the treatment sample comprises a pH of from about 6.0 to about 7.0. In some embodiments, the treatment sample comprises a pH of from about 4.0 to about 6.0. In some embodiments, the treatment sample comprises a pH of from about 5.0 to about 6.0. In some embodiments, the treatment sample comprises a pH of from about 4.0 to about 5.0.

In some embodiments, the treatment sample comprises a pH about 3.0. In some embodiments, the treatment sample comprises a pH about 4.0. In some embodiments, the treatment sample comprises a pH about 5.0. In some embodiments, the treatment sample comprises a pH about 6.0. In some embodiments, the treatment sample comprises a pH about 7.0.

In some embodiments, the treatment sample comprises a pH below about 3.0. In some embodiments, the treatment sample comprises a pH below about 4.0. In some embodiments, the treatment sample comprises a pH below about 5.0. In some embodiments, the treatment sample comprises a pH below about 6.0. In some embodiments, the treatment sample comprises a pH a below bout 7.0.

In some embodiments, the volume of the treatment sample is the total volume of the mixture of the biological sample, the collection buffer, to one or more additives prior to hyperbaric heating. In some embodiments, the volume of the treatment sample is from 100 μL to 5 mL. In some embodiments, the volume of the treatment sample is from 200 μL to 5 mL. In some embodiments, the volume of the treatment sample is from 300 μL to 5 mL. In some embodiments, the volume of the treatment sample is from 400 μL to 5 mL. In some embodiments, the volume of the treatment sample is from 500 μL to 5 mL. In some embodiments, the volume of the treatment sample is from 1 mL to 5 mL. In some embodiments, the volume of the treatment sample is from 1.5 mL to 5 mL. In some embodiments, the volume of the treatment sample is from 2 mL to 5 mL. In some embodiments, the volume of the treatment sample is from 2.5 mL to 5 mL. In some embodiments, the volume of the treatment sample is from 3 mL to 5 mL. In some embodiments, the volume of the treatment sample is from 3.5 mL to 5 mL. In some embodiments, the volume of the treatment sample is from 4 mL to 5 mL. In some embodiments, the volume of the treatment sample is from 4.5 mL to 5 mL.

In some embodiments, the treatment sample comprises from 10 copies/mL to $10^9$ copies/mL of the nucleic acid. In some embodiments, the treatment sample comprises from 50 copies/mL to $10^9$ copies/mL of the nucleic acid. In some embodiments, the treatment sample comprises from 100 copies/mL to $10^9$ copies/mL of the nucleic acid. In some embodiments, the treatment sample comprises from $10^3$ copies/mL to $10^9$ copies/mL of the nucleic acid. In some embodiments, the treatment sample comprises from $10^4$ copies/mL to $10^9$ copies/mL of the nucleic acid. In some embodiments, the treatment sample comprises from $10^5$ copies/mL to $10^9$ copies/mL of the nucleic acid. In some embodiments, the treatment sample comprises from $10^6$ copies/mL to $10^9$ copies/mL of the nucleic acid.

In some embodiments, the treatment sample comprises from 10 copies/mL to $10^8$ copies/mL of the nucleic acid. In some embodiments, the treatment sample comprises from 50 copies/mL to $10^8$ copies/mL of the nucleic acid. In some embodiments, the treatment sample comprises from 100 copies/mL to $10^8$ copies/mL of the nucleic acid. In some embodiments, the treatment sample comprises from $10^3$ copies/mL to $10^8$ copies/mL of the nucleic acid. In some embodiments, the treatment sample comprises from $10^4$ copies/mL to $10^8$ copies/mL of the nucleic acid. In some embodiments, the treatment sample comprises from $10^5$ copies/mL to $10^8$ copies/mL of the nucleic acid. In some embodiments, the treatment sample comprises from $10^6$ copies/mL to $10^8$ copies/mL of the nucleic acid.

In some embodiments, the treatment sample comprises from 10 copies/mL to $10^7$ copies/mL of the nucleic acid. In some embodiments, the treatment sample comprises from 50 copies/mL to $10^7$ copies/mL of the nucleic acid. In some embodiments, the treatment sample comprises from 100 copies/mL to $10^7$ copies/mL of the nucleic acid. In some embodiments, the treatment sample comprises from $10^3$ copies/mL to $10^7$ copies/mL of the nucleic acid. In some embodiments, the treatment sample comprises from $10^4$ copies/mL to $10^7$ copies/mL of the nucleic acid. In some embodiments, the treatment sample comprises from $10^1$ copies/mL to $10^7$ copies/mL of the nucleic acid. In some embodiments, the treatment sample comprises from $10^6$ copies/mL to $10^7$ copies/mL of the nucleic acid.

In some aspects, the treatment sample comprises one or more additives. The one or more additives may comprise a chelating agent, a single-stranded nucleic acid binding protein, a reducing agent, a protease, a nuclease inhibitor, or combination thereof.

In some embodiments, the treatment sample comprises a chelating agent. In some embodiments, the chelating agent is an insoluble chelating agent. In some embodiments, the insoluble chelating agent comprises a chelating resin. The chelating resin may be a polymer or copolymer. The chelating resin may be a cation-binding agent or a metal ion-binding agent. The chelating resin may be in the form of microbeads. In some embodiments, the chelating agent comprises crosslinked polystyrene. The chelating agent may comprise one or more functional groups. The one or more functional groups may comprise a sulfonic acid or sulfonate group; a quaternary amino group (e.g., trimethylammonium); a primary, secondary, and/or tertiary amino group (e.g., polyethylene amine); or a carboxylic acid or carboxylate group. In some embodiments, the insoluble chelating agent comprises a styrene divinylbenzene co-polymer. In some embodiments, the insoluble chelating agent comprises Chelex resin or Chelex. In some embodiments, the Chelex is stored in the collection buffer.

In some embodiments, the chelating agent is a soluble chelating agent. In some embodiments, the soluble chelating agent comprises ethylenediaminetetraacetic acid (EDTA). In some embodiments, the chelating agent comprises EDTA, nitrilotriacetic acid, n-hydroxyethylethylenediaminetriacetic acid (HEDTA), ethylenediamine, dimercaprol, porphine, heme, hemoglobin, or chlorophyll. In some embodiments, the chelating agent comprises simple organic acids such as oxalic acid, malic acid, rubeanic acid, or citric acid.

In some embodiments, the chelating agent is added at a final concentration, defined as the percent weight by volume of the chelating agent weight by the volume of the treatment sample (e.g., mixture comprising biological sample, collection buffer, chelating agent, single stranded nucleic acid binding protein, and reducing agent) prior to heating. In some embodiments, the final concentration of chelating agent in the treatment sample prior to heating is from 1% to 40%, from 2.5% to 35%, from 5% to 25%, from 7.5% to 20%, or from 10% to 15% weight by volume of the chelating agent weight by the treatment sample volume. In some embodiments, the final concentration of chelating agent in the treatment sample prior to heating is at about 2%, at about 4%, at about 6%, at about 8%, at about 10%, at about 12%, at about 14%, at about 16%, at about 18%, or at about 20% weight by volume of the chelating agent weight by the treatment sample volume.

In some embodiments, the treatment sample further comprises a single stranded nucleic acid binding (SSB) protein. In some embodiments, the single stranded nucleic acid binding protein is thermostable. In some embodiments, the SSB protein is thermostable at a temperature of from 4 degrees Celsius to 170 degrees Celsius, from 4 degrees Celsius to 160 degrees Celsius, from 4 degrees Celsius to 150 degrees Celsius, from 4 degrees Celsius to 140 degrees Celsius, from 4 degrees Celsius to 130 degrees Celsius, or from 4 degrees Celsius to 120 degrees Celsius. In some embodiments, the SSB protein is thermostable at a temperature of from 90 to 170 degrees Celsius, from 90 to 160 degrees Celsius, from 90 to 150 degrees Celsius, from 90 to 140 degrees Celsius, from 90 to 130 degrees Celsius, from 90 to 120 degrees Celsius, or from 90 to 110 degrees Celsius.

In some embodiments, the final molar concentration of the SSB protein in the treatment sample (e.g., mixture comprising biological sample, collection buffer, chelating agent, SSB protein, and reducing agent) prior to heating is at a concentration from 0.1 μM to 5 μM, from 0.1 μM to 4 μM, from 0.1 μM to 3 μM, from 0.1 μM to 2 μM, from 0.1 μM to 1 μM, from 0.2 μM to 0.9 μM, from 0.3 μM to 0.7 μM, or from 0.4 μM to 0.6 μM.

In some embodiments, the final molar concentration of the SSB protein in the treatment sample (e.g., mixture comprising biological sample, collection buffer, chelating agent, SSB protein, and reducing agent) prior to heating is at about 0.1 μM, at about 0.2 μM, at about 0.3 μM, at about 0.4 μM, at about 0.5 μM, at about 0.6 μM, at about 0.7 μM, at about 0.8 μM, at about 0.9 μM, at about 1 μM, at about 1.1 μM, at about 1.2 μM, at about 1.3 μM, at about 1.4 μM, at about 1.5 μM, at about 1.6 μM, at about 1.7 μM, at about 1.8 μM, at about 1.9 μM, at about 2 μM, at about 2.2 μM, at about 2.4 μM, 2.6 μM, at about 2.8 μM, at about 3 μM, at about 3.5 μM, at about 4 μM, at about 4.5 μM, or at about 5 μM.

In some embodiments, the single stranded nucleic acid binding protein is derived from a thermophilic organism. In some embodiments, the thermophilic organism is a thermophilic microorganism or a thermophilic bacteria. In some embodiments, the single stranded nucleic acid binding protein is derived from an organism selected from *Thermotoga maritima* (TmaSSB), *Thermotoga* neapolitana (TneSSB), *Thermococcus kodakarensis* (KOD), and *Thermus thermophilus* (TthSSB). In some embodiments, the single stranded nucleic acid binding protein is, for example, derived from *Thermus aquaticus* (TaqSSB) or *Thermococcus kodakarensis* (KOD). In some embodiments, the single stranded nucleic acid binding protein is derived from an organism selected from *Thermotoga maritima* (TmaSSB), *Thermotoga* neapolitana (TneSSB), and *Thermus thermophilus* (TthSSB). In some embodiments, the single stranded nucleic acid binding protein is derived from *Thermotoga maritima* (TmaSSB). In some embodiments, the single stranded nucleic acid binding protein is derived from *Thermotoga* neapolitana (TneSSB). In some embodiments, the single stranded nucleic acid binding protein is derived from *Thermococcus kodakarensis* (KOD). In some embodiments, the single stranded nucleic acid binding protein is derived from *Thermus thermophilus* (TthSSB). In some embodiments, the single stranded nucleic acid binding protein is selected from ET SSB, *E. Coli* SSB, KOD SSB, TthSSB, TneSSB, TmaSSB, and TaqSSB.

In some embodiments, the treatment sample comprises a reducing agent. In some embodiments the reducing agent is added to the treatment sample prior to heating. The reducing agent may be 2-Mercaptoethanol, 2-Mercaptoethylamine-HCl, TCEP, Cysteine-HCl, Dithiothreitol (DTT), TCEP-HCl, thiol-based reducing agent, Guanidine-HCl, or urea.

In some embodiments, the final molar concentration of the reducing agent in the treatment sample (e.g., mixture comprising biological sample, collection buffer, chelating agent, SSB protein, and reducing agent) prior to heating is at a concentration from 0.1 mM to 10 mM, 0.1 mM to 9 mM, from 0.1 mM to 8 mM, from 0.1 mM to 7 mM, from 0.1 mM to 6 mM, from 0.1 mM to 5 mM, from 0.1 mM to 4 mM, from 0.1 mM to 3 mM, from 0.1 mM to 2 mM, from 0.2 mM to 1.8 mM, from 0.4 mM to 1.6 mM, from 0.6 mM to 1.4 mM, or from 0.8 mM to 1.2 mM. In some embodiments, the final molar concentration of the reducing agent in the treatment sample (e.g., mixture comprising biological sample, collection buffer, chelating agent, SSB protein, and reducing agent) prior to heating is at about 0.1 mM, at about 0.2 mM, at about 0.3 mM, at about 0.4 mM, at about 0.5 mM, at about 0.6 mM, at about 0.7 mM, at about 0.8 mM, at about 0.9 mM, at about 1 mM, at about 1.2 mM, at about 1.4 mM, at about 1.6 mM, at about 1.8 mM, at about 2 mM, at about 2.5 mM, at about 5 mM, at about 7.5 mM, or at about 10 mM.

In some embodiments, the treatment sample comprises one or more reagents selected from: a chelating agent, a single stranded nucleic acid binding protein, and a reducing agent. In some embodiments, the treatment sample comprises at least two reagents selected from: a chelating agent, a single stranded nucleic acid binding protein, and a reducing agent. In some embodiments, the treatment sample comprises a chelating agent, a single stranded nucleic acid binding protein, and a reducing agent. In some embodiments, the concentration of the chelating agent is from 2.5% to 35% weight by volume of the treatment sample, the concentration of the single-stranded nucleic acid binding protein in the treatment sample is from 0.1 μM to 5 μM, and the concentration of the reducing agent in the treatment sample is from 0.1 mM to 5 mM. In some embodiments, the concentration of the chelating agent is from 5% to 25% weight by volume of the treatment sample, the concentration of the single-stranded nucleic acid binding protein in the treatment sample is from 0.1 μM to 2 μM, and the concentration of the reducing agent in the treatment sample is from 0.1 mM to 2 mM. In some embodiments, the concentration of the chelating agent is from 10% to 15% weight by volume of the treatment sample, the concentration of the single-stranded nucleic acid binding protein in the treatment sample is from 0.3 μM to 0.7 μM, and the concentration of the reducing agent in the treatment sample is from 0.6 mM to 1.4 mM.

In some embodiments, the treatment sample comprises a stabilizer. In some embodiments, the treatment sample is mixed with a stabilizer prior to heating. In some cases, the stabilizer may help prevent degradation of a nucleic acid. In some cases, the stabilizer may help inactivate a molecular amplification inhibitor during hyperbaric heating. In some embodiments, the stabilizer may stabilize a protein. In some embodiments, the stabilizer may stabilize a nucleic acid. In some embodiments, the stabilizer may stabilize a nucleic acid and a protein. A stabilizer may improve the viscosity of the treatment sample. A stabilizer may help prevent or reduce aggregation between one or more proteins. A stabilizer may improve solubility of a protein. A stabilizer may reduce nonspecific binding between one or more components (e.g., proteins). A stabilizer may be a blocking agent. A stabilizer may be a component that stabilizes one or more components in the treatment sample. In some embodiments, the stabilizer may stabilize the nucleic acid. In some embodiments, the stabilizer may stabilize the chelating agent. In some embodiments, the stabilizer may stabilize the single-stranded nucleic acid binding protein. For example, a stabilizer may be bovine serum albumin (BSA). A stabilizer may be gelatin. In some embodiments, the stabilizer has a concentration from 100 ng/mL to 15 mg/mL, from 200 ng/mL to 15 mg/mL, from 300 ng/mL to 15 mg/mL, from 400 ng/mL to 15 mg/mL, from 500 ng/mL to 15 mg/mL, or from 1 mg/mL to 15 mg/mL in the treatment sample. In some embodiments, the stabilizer has a concentration from 100 ng/mL to 10 mg/mL, from 200 ng/mL to 10 mg/mL, from 300 ng/mL to 10 mg/mL, from 400 ng/mL to 10 mg/mL, from 500 ng/mL to 10 mg/mL, or from 1 mg/mL to 10 mg/mL in the treatment sample. In some embodiments, the stabilizer has a concentration from 500 ng/mL to 2 mg/mL, from 500 ng/mL to 3 mg/mL, from 500 ng/mL to 4 mg/mL, from 500 ng/mL to 5 mg/mL, from 500 ng/mL to 6 mg/mL, from 500 ng/mL to 7 mg/mL, from 500 ng/mL to 8 mg/mL, from 500 ng/mL to 9 mg/mL, or from 500 ng/mL to 10 mg/mL in the treatment sample.

In some embodiments, the treatment sample comprises one or more reagents selected from: a chelating agent, a single stranded nucleic acid binding protein, a reducing agent, stabilizer. In some embodiments, the treatment sample comprises at least two reagents selected from: a chelating agent, a single stranded nucleic acid binding protein, a reducing agent, and a stabilizer. In some embodiments, the treatment sample comprises at least three reagents selected from: a chelating agent, a single stranded nucleic acid binding protein, a reducing agent, and a stabilizer. In some embodiments, the treatment sample comprises a chelating agent, a single stranded nucleic acid binding protein, and a reducing agent. In some embodiments, the concentration of the chelating agent is from 2.5% to 35% weight by volume of the treatment sample, the concentration of the single-stranded nucleic acid binding protein in the treatment sample is from 0.1 μM to 5 μM, the concentration of the reducing agent in the treatment sample is from 0.1 mM to 5 mM, and the concentration of the stabilizer is from 500 ng/mL to 10 mg/mL. In some embodiments, the concentration of the chelating agent is from 5% to 25% weight by volume of the treatment sample, the concentration of the single-stranded nucleic acid binding protein in the treatment sample is from 0.1 μM to 2 μM, the concentration of the reducing agent in the treatment sample is from 0.1 mM to 2 mM, and the concentration of the stabilizer is from 500 ng/mL to 10 mg/mL. In some embodiments, the concentration of the chelating agent is from 10% to 15% weight by volume of the treatment sample, the concentration of the single-stranded nucleic acid binding protein in the treatment sample is from 0.3 μM to 0.7 μM, the concentration of the reducing agent in the treatment sample is from 0.6 mM to 1.4 mM, and the concentration of the stabilizer is from 500 ng/mL to 10 mg/mL.

In some embodiments, the treatment sample comprises a protease. In some embodiments, the treatment sample is mixed with a protease prior to heating. In some embodiments, the protease is, for example, Proteinase K. In some embodiments, the biological sample is mixed with a reducing agent and a protease prior to heating. In some embodiments, the final concentration of the protease in the treatment sample (e.g., mixture comprising biological sample, collection buffer, chelating agent, SSB protein, reducing agent, and protease) prior to heating is at a concentration from 0.01 mg/mL to 5 mg/mL, from 0.02 mg/mL to 4 mg/mL, from 0.03 mg/mL to 3 mg/mL, from 0.04 mg/mL to 2 mg/mL, from 0.05 mg/mL to 1 mg/mL, from 0.075 mg/mL to 0.75 mg/mL, or from 0.1 mg/mL to 0.5 mg/mL. In some embodiments, the final concentration of the protease in the treatment sample (e.g., mixture comprising biological sample, collection buffer, chelating agent, SSB protein, reducing agent, and protease) prior to heating is at about 0.05 mg/mL, at about 0.075 mg/mL, at about 0.1 mg/mL, at about 0.25 mg/mL, at about 0.5 mg/mL, at about 0.75 mg/mL, or at about 1 mg/mL.

In some embodiments, the treatment sample comprises a nuclease inhibitor. In some embodiments, the treatment sample comprises an RNAse inhibitor. In some embodiments, an amount of RNAse inhibitor is added prior to heating, e.g., at about 1 U, at about 10 U, at about 50 U, at about 100 U, at about 150 U, at about 200 U, at about 250 U, at about 300 U, at about 350 U, at about 400 U, at about 450 U, or at about 500 U.

In some embodiments, an amount of RNAse inhibitor in the treatment sample is from about 1 U to about 500 U. In some embodiments, the amount of RNAse inhibitor in the treatment sample is from about 10 U to about 500 U. In some embodiments, the amount of RNAse inhibitor in the treatment sample is from about 50 U to about 500 U. In some embodiments, the amount of RNAse inhibitor in the treatment sample is from about 100 U to about 500 U. In some embodiments, the amount of RNAse inhibitor in the treatment sample is from about 150 U to about 500 U. In some embodiments, the amount of RNAse inhibitor in the treatment sample is from about 200 U to about 500 U. In some embodiments, the amount of RNAse inhibitor in the treatment sample is from about 250 U to about 500 U. In some embodiments, the amount of RNAse inhibitor in the treatment sample is from about 300 U to about 500 U. In some embodiments, the amount of RNAse inhibitor in the treatment sample is from about 350 U to about 500 U. In some embodiments, the amount of RNAse inhibitor in the treatment sample is from about 400 U to about 500 U. In some embodiments, the amount of RNAse inhibitor in the treatment sample is from about 450 U to about 500 U.

In some embodiments, the amount of RNAse inhibitor in the treatment sample is from about 1 U to about 200 U. In some embodiments, the amount of RNAse inhibitor in the treatment sample is from about 10 U to about 200 U. In some embodiments, the amount of RNAse inhibitor in the treatment sample is from about 50 U to about 200 U. In some embodiments, the amount of RNAse inhibitor in the treatment sample is from about 100 U to about 200 U. In some embodiments, the amount of RNAse inhibitor in the treatment sample is from about 150 U to about 200 U.

In some embodiments, the treatment sample further comprises a molecular amplification inhibitor. In some cases, the molecular amplification inhibitor may be an agent that binds to nucleic acid. The molecular amplification inhibitor may be an agent that degrades nucleic acid. In some cases, the molecular amplification inhibitor may be a nuclease. In some cases, the molecular amplification inhibitor is a DNase. In other cases, the molecular amplification inhibitor is an RNase. In some embodiments, the treatment sample comprises one or more molecular amplification inhibitors that may be inactivated after heating.

Additional details and examples of using hyperbaric conditions to process samples are disclosed in International Application No. PCT/US23/67879, the entire content of which is incorporated herein by reference.

Methods for Sample Processing or Analysis

The present disclosure provides a method for sample processing and/or analysis. For example, the method can be used to subject a sample comprising a nucleic acid to nucleic acid amplification such as real-time polymerase chain reaction (PCR). In some embodiments, centripetal microfluidics are applied to fluid within a PCR device. One advantage of centripetal microfluidics, for example, is that the centrifugal pumping is applied to the fluid without the need to any direct connection to the instrument, helping to prevent contamination. In some embodiments, the present disclosure provides a method of amplifying nucleic acid in a PCR device comprising a rotatable disc. In some embodiments, the method comprises maintaining one or more reaction samples in place in one or more reaction chambers during heating and substantially preventing evaporation in the one or more reaction chambers. In some embodiments, the method comprises transferring a sample comprising the target nucleic acid to be analyzed to one or more reaction chambers in 30 seconds or less and subsequently, sealing the one or more reaction chambers. In some embodiments, sealing a reaction chamber substantially prevents any liquid or steam from escaping the reaction chamber.

In some embodiments, the method comprises loading a sample comprising a target nucleic acid (e.g., a bodily sample, a treatment sample, or a heat-treated sample) into a loading chamber on the rotatable disc. In some cases, the sample is heated in a separate heating chamber (e.g., in hyperbaric heating conditions) prior to loading into the loading chamber. In some cases, the loading chamber is or comprises a heating chamber, and the method comprises heating the sample comprising the target nucleic acid in the loading chamber in a hyperbaric condition to produce a processed sample (e.g., a heat treated sample), as described elsewhere herein. In some cases, the sample is heated in a hyperbaric condition to a temperature above 100 degrees Celsius. In some cases, the sample is heated in a hyperbaric condition to a temperature of from 101 degrees Celsius to 160 degrees Celsius. In some cases, the heating occurs at a temperature ramp rate from 5 degrees Celsius per second to 50 degrees Celsius per second.

In some embodiments, the loaded sample is a treatment sample as described elsewhere herein (e.g., a nucleic acid containing sample prior to treatment by hyperbaric heating) and is directly heated in the loading chamber. In some cases, the sample comprising the target nucleic acid that is heated comprises a bodily sample selected from the group consisting of: a blood sample, a lacrimal fluid sample, a saliva sample, a mucus sample, a sputum sample, a feces sample, a cerebrospinal fluid sample, and a urine sample. In some cases, the target nucleic acid is not extracted, isolated, or otherwise purified from said bodily sample prior to heating. In some cases, the sample comprising the target nucleic acid comprises a plurality of molecular amplification inhibitors and the heating inactivates a molecular amplification inhibitor of the plurality of molecular amplification inhibitors in the sample, as described elsewhere herein. In some cases, the heating inactivates at least 70% of the plurality of molecular amplification inhibitors to produce the processed sample.

In some cases, the sample further comprises one or more reagents selected from the group consisting of: a chelating agent, a single stranded nucleic acid binding protein, a reducing agent, and a stabilizer. For example, a bodily sample comprising nucleic acid as described elsewhere herein (e.g., saliva) can be pre-mixed with additives (e.g., a reducing agent, chelating agent, a single-stranded binding protein, a stabilizer, or a combination thereof) to produce the treatment sample that is subsequently loaded into the loading chamber, where the sample is heated. Alternatively, a bodily sample can be loaded into a loading chamber that is pre-loaded with additives (e.g., a reducing agent, chelating agent, a single-stranded binding protein, a stabilizer, or a combination thereof), wherein the sample mixes with the one or more reagents and is subsequently heated in the loading chamber.

During sample heating, the sample may be in a sealed or closed heating chamber. In some embodiments, following heating, an exit valve is opened to release the sample from the loading chamber (e.g., heating chamber). The exit valve may be opened by electromagnetic means. For example, the exit valve may be a laser valve that is opened using a laser. In some embodiments, the method comprises rotating the rotatable disc such that the processed sample exits the loading chamber from the exit valve via centrifugation forces. In some cases, the centrifugation forces are generated using spin speeds from 3000 rpm to 6000 rpm. In some cases, the rotatable disc further comprises a reaction chamber and a channel connecting the loading chamber to the reaction chamber. In some cases, the rotatable disc is rotated in order to transfer the processed sample from the loading chamber to the reaction chamber via the channel. In some cases, the processed sample flows from the loading chamber to one or more intermediate chambers before flowing to the reaction chamber via the channel.

For example, rotating the rotatable disc may cause the processed sample to flow from the loading chamber into a collection chamber (e.g., a metering chamber) that is immediately downstream of the loading chamber via a channel. In some embodiments, the method for sample processing and/or analysis further comprises metering a specific volume of sample to be processed or analyzed (e.g., a nucleic acid containing sample, bodily sample, treatment sample, or post-hyperbaric heating treatment sample). In some embodiments, sample metering occurs after loading the sample into the loading chamber on the rotatable disc. In some embodiments, sample metering occurs after initial sample preparation (e.g., treatment by hyperbaric heating). The sample metering can occur in a metering chamber, which can be the loading chamber where the sample is loaded or a separate collection chamber to where the sample flows after initial sample preparation (e.g., hyperbaric heating in a heating chamber). In some cases, the volume is pre-set depending on the requirements of a sample processing and/or analysis assay. In some cases, multiple aliquots of sample are metered for multiplexed sample processing and/or analysis. In some embodiments, following sample metering, the metered volume is sent toward a reagent mixing chamber. In embodiments, the flow of the metered volume into the reagent mixing chamber is controlled by a valve (e.g., a laser valve). In some embodiments, any extra volume of sample above the metered volume(s) flows into an overflow chamber.

In some embodiments, the method for sample processing and/or analysis further comprises mixing the sample to be processed or analyzed with a PCR reagent mixture (e.g., RT-PCR reagent mixture). The PCR reagent mixture can comprise a polymerase or a reverse transcriptase or a combination thereof. The PCR reagent mixture can comprise a buffer and a plurality of nucleotides (e.g., dNTPs). The PCR reagent mixture can comprise BSA. In some embodiments, the PCR reagent mixture comprises a primer comprising a sequence that is complementary to at least a portion of the target nucleic acid. In some embodiments, the PCR reagent mixture comprises a probe comprising a sequence that is complementary to at least a portion of the target nucleic acid. In some embodiments, the PCR reagent mixture comprises a polymerase, a reverse transcriptase, magnesium, a buffer solution, BSA, and a plurality of nucleotides. In some embodiments, the PCR reagent mixture is provided as a lyophilized powder. In some embodiments, one or more of the PCR reagents in the PCR reagent mixture is provided as a lyophilized reagent bead. In some embodiments, the PCR reagent mixture is provided in a reagent mixing chamber, and the sample is mixed with the PCR reagent mixture in the reagent mixing chamber. In some embodiments, the reagent mixing chamber is or is connected to the loading chamber. In some embodiments, the reagent mixing chamber is connected to the metering chamber and receives a metered volume of the sample comprising the target nucleic acid. The sample comprising the target nucleic acid and the PCR reagent mixture can be mixed by Euler forces, producing a combined target nucleic acid and the PCR reagent mixture.

In some embodiments, the method for sample processing and/or analysis comprises transferring the target nucleic acid into a reaction chamber (e.g., a cuvette) or a plurality of reaction chambers (e.g., a plurality of cuvettes) on the rotatable disc. In some cases, the combined target nucleic acid and PCR reagent mixture is transferred from the reagent mixing chamber to the one or more reaction chambers. The release of the combined mixture from the reagent mixing chamber can be controlled by a valve (e.g., a laser valve). In some embodiments, the nucleic acid and PCR reagent mixture is transferred from the reagent mixing chamber into the reaction chamber or the plurality of reaction chambers via centrifugation forces. In some cases, the centrifugation forces are generated using spin speeds from 1000 rpm to 3000 rpm.

In some embodiments, the one or more reaction chambers (e.g., cuvettes) are pre-loaded with one or more PCR reagents. For example, the one or more reaction chambers can be pre-loaded with one or more primers complementary to at least a portion of the target nucleic acid. The one or more primers can be provided as a lyophilized powder. In some embodiments, the one or more reaction chambers are pre-loaded with a probe complementary to at least a portion of the target nucleic acid. The probe can be provided as a lyophilized powder. In another embodiment, the primer or probe is dried inside the one or more reaction chambers (e.g., cuvettes). In some embodiments, the sample comprising the target nucleic acid is mixed with one or more PCR reagents in the PCR reagent mixing chamber and is mixed with one or more additional PCR reagents in the reaction chamber. For example, the sample comprising the target nucleic acid can be mixed with a PCR reagent mixture comprising a polymerase or reverse transcriptase, a plurality of nucleotides, BSA, and a reaction buffer in the PCR reagent mixing chamber and subsequently mixed with a primer and a probe in the reaction chamber.

In some embodiments, the method for sample processing and/or analysis further comprises sealing the one or more reaction chambers after transferring the mixture comprising the target nucleic acid into the one or more reaction chambers. In some embodiments, sealing the reaction chambers substantially prevents the mixture from exiting the chamber. In some embodiments, the rotatable disc comprises a cuvette insert that comprises the one or more reaction chambers and a cuvette channel by which the sample containing the target nucleic acid flows into a plurality of reaction chambers (e.g., cuvettes). The one or more reaction chambers (e.g., cuvettes) can be sealed using a heat sealer. In some embodiments, the rotatable disc is contacted with a sealer, thereby sealing the channel after the processed sample flows into the one or more reaction chambers. In some embodiments, the channel is heat sealed at a temperature from 200 to 300 degrees Celsius. In some embodiments, the channel is sealed by using the heat sealer to compress or crush the channel. In some embodiments, sealing the cuvette channel substantially prevents fluid communication between the plurality of reaction chambers.

In some embodiments, the method for sample processing and/or analysis further comprises amplifying the target nucleic acid in the one or more reaction chambers. In some embodiments, the nucleic acid amplification reactions are carried out after heat sealing of the one or more reaction chambers. In some embodiments, the cuvette insert comprising the one or more reaction chambers is first pressed between the 95° C. temperature block for 5 to 30 seconds to activate the DNA polymerase. In some embodiments, the cuvette insert is moved between different heating elements (e.g., temperature blocks) to carry out different thermocycling steps. In some embodiments, thermocycling comprises rotating the rotatable disc to bring the reaction chamber (e.g., cuvette) adjacent to a first heating element maintained at a first temperature, thereby denaturing the target nucleic acid in the sample. In some embodiments, thermocycling further comprises rotating the rotatable disc to bring the reaction chamber adjacent to a second heating element maintained at a second temperature, thereby annealing the primer to the denatured nucleic acid and replicating the target nucleic acid. In some embodiments, thermocycling further comprises rotating the rotatable disc to bring the plurality of reaction chambers (e.g., cuvettes) adjacent to a third heating element maintained at a third temperature, thereby replicating the target nucleic acid.

In some aspects, the present disclosure provides a method for sample analysis. The method can comprise: (a) loading a sample comprising a target nucleic acid into a loading chamber on a rotatable disc. The rotatable disc can further comprise a plurality of reaction chambers and a channel connecting the loading chamber to the plurality of reaction chambers. The sample can flow to the plurality of reaction chambers via the channel following loading of the sample. The method can further comprise (b) contacting the rotatable disc with a sealer. The sealer can seal the channel and prevent fluid communication between the plurality of reaction chambers after filling. In certain embodiments, the sealer is incorporated into the PCR device. The method may further comprise (c) rotating the rotatable disc to bring the plurality of reaction chambers adjacent to a first heating element maintained at a first temperature. The first heating element can be used to denature the target nucleic acid in the sample. The method can further comprise (d) rotating the rotatable disc to bring the plurality of reaction chambers adjacent to a second heating element maintained at a second temperature. The second heating element can be used to anneal the primer to the denatured target nucleic acid and replicate the denatured target nucleic acid. The method may further comprise (e) exposing the plurality of reaction chambers to an excitation light of a first wavelength. The method may further comprise (f) measuring an emitted light of a second wavelength from the plurality of reaction chambers. In some cases, some of the steps, e.g., steps (c) through (f) described herein, can be repeated until the emitted light is measured at an intensity indicating the presence of the target nucleic acid.

Another aspect of the present disclosure is directed to a method for multiplexed real-time amplification and detection of a plurality of different target nucleic acids using a rotatable disc comprising a plurality of reaction chambers (e.g., cuvettes). The method can comprise (a) loading a sample comprising the plurality of different target nucleic acids into the rotatable disc. The sample can then be transferred to the plurality of reaction chambers. The sample can be mixed with a plurality of primers, wherein each of the plurality of primers is complementary to a portion of a corresponding target nucleic acid of the plurality of different target nucleic acids. The plurality of primers can be pre-loaded to the plurality of reaction chambers. The method may further comprise (b) rotating the rotatable disc to bring the plurality of reaction chambers adjacent to a first heating element maintained at a first temperature. The first heating element may be used to denature each of the plurality of target nucleic acids in the sample. The method may further comprise (c) rotating the rotatable disc to bring the plurality of chambers adjacent to a second heating element maintained at a second temperature. The second heating element may be used to anneal the plurality of primers to the corresponding target nucleic acids denatured in (b) and replicate the plurality of different target nucleic acids. The method can further comprise (d) exposing the plurality of reaction chambers (e.g., cuvettes) to an excitation light comprising a plurality of excitation wavelengths. The method may further comprise detecting a signal from the sample. For example, the method may further comprise (e) measuring an emitted light comprising a plurality of emission wavelengths from the plurality of reaction chambers (e.g., cuvettes), wherein each of the plurality of emission wavelengths corresponds to the presence of each of the plurality of different target nucleic acids. In some cases, some of the steps, e.g., steps (b) through (e), can be repeated until the emitted light is measured at an intensity indicating the presence of the plurality of different target nucleic acids. In some embodiments, the rotatable disc further comprises a loading chamber in fluid communication with the plurality of reaction chambers through a channel. In some embodiments, prior to (b), the method further comprises contacting the rotatable disc with a sealer, thereby sealing the channel and preventing fluid communication between the plurality of reaction chambers (e.g., cuvettes).

In some embodiments, the sealer is housed within an analytical device for real-time PCR, thereby enabling a full sample-answer system by integrating a microfluidic sample preparation system with a nucleic acid processing system. In some embodiments, each reaction chamber (e.g., cuvette) is sealed by contact or non-contact means to avoid evaporation and escape of the heated liquid. In some embodiments, sealing of the channel is achieved via heat and pressure, via LASER welding or via ultrasonic welding. In some embodiments, sealing of the channel is achieved via heat and pressure, such as, but not limited to, by a heat sealer. In some embodiments, the sealer is a heat sealer. In some embodiments, the sealer comprises a first element configured to provide a thermal energy and a pressure on the rotatable disc and a second element configured to provide a counter force to the pressure. In some embodiments, contacting the rotatable disc with the sealer comprises applying the pressure on the rotatable disc such that the channel deforms.

In some embodiments, prior to (b), the method further comprises rotating the rotatable disc to generate a sufficient centripetal force on the sample to cause the sample to flow through the channel and into the plurality of reaction chambers. In some embodiments, the sufficient centripetal force is generated by spinning the rotatable disc from about 500 RPM to about 15000 RPM.

In some embodiments, the channel is defined by two plastic sheets welded together by two parallel lines. In some embodiments, the channel comprises a thin plastic film with diameter ranging from about 1 μm to about 1 mm. In some embodiments, the channel defines a lumen with a diameter ranging from about 1 μm to about 1 mm. In some embodiments, the channel comprises a thermoplastic material that seals the channel when heated to a target temperature. In some embodiments, the target temperature comprises from about 110 degrees C. to about 300 degrees C.

In some embodiments, the reaction chambers FIG. 5 503 are defined by a thermoplastic film FIG. 5 501 sealed to a sealing film FIG. 5 502.

Figure 6:
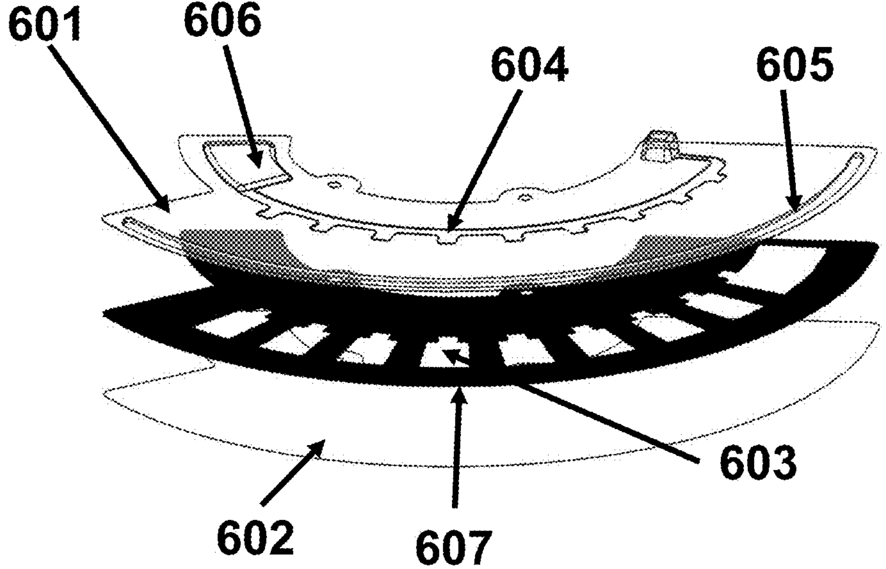
FIG. 6 illustrates the components used to manufacture some embodiments of a rotatable disc described herein.

In another embodiment, the reaction chambers are defined by a film FIG. 6 607 sealed in both side by two films, thermoformed film FIG. 6 601 and a sealing film FIG. 6 602. In this embodiment, reaction chamber depth is not defined by thermoforming but by the thickness of film FIG. 6 607 which is from 0.1 to 1 mm.

In some embodiments, the excitation light or the emission light comprises one wavelength each. In some embodiments, the excitation light or the emission light comprises two or more wavelengths each. In some embodiments, the excitation light or the emission light comprises one to 10 wavelengths each. In some embodiments, the excitation light or the emission light comprises one to 6 wavelengths each. In some embodiments, the excitation light or the emission light comprises one to 4 wavelengths each. In some embodiments, the excitation light and the emission light are independently selected at each occurrence from about 400 nm to about 750 nm. In some embodiments, the excitation light and the emission light are pairs of wavelengths associated with excitation and emission from a fluorescent probe. For example, the first wavelength and the second wavelength are compatible with FAM (e.g., 495 nm/520 nm), SUN (e.g., 538 nm/554 nm), 5' TEX 615 (e.g., 596 nm/613 nm), or Cy5 (e.g., 648 nm/667 nm) detection. For example, and not by way of limitation, the first wavelength is independently selected from about 495 nm, about 538 nm, about 596 nm, and about 648 nm. For example, and not by way of limitation, the second wavelength is independently selected from about 520 nm, about 554 nm, about 613 nm, and about 667 nm.

In some embodiments, the sample is mixed with a primer complementary to at least a portion of the target nucleic acid pre-loaded within the plurality of reaction chambers. In some embodiments, the plurality of reaction chambers further comprises a probe, and wherein the sample is further mixed with the probe. In some embodiments, the plurality of primers is stored in the plurality of reaction chambers. In some embodiments, the plurality of primers is provided as a lyophilized powder. In some embodiments, the probe is provided as a lyophilized powder. In another embodiment, primers and probes are dried inside each reaction chamber (e.g., cuvette).

In some embodiments, prior to transferring the sample to the plurality of reaction chambers, the sample is mixed with a PCR reagent mixture. In some embodiments, the PCR reagent mixture comprises a polymerase, a reverse transcriptase, magnesium, a buffer solution, BSA, and a plurality of nucleotides. In some embodiments, the components of the PCR reagent mixture are pre-mixed before contacting the sample or loading to the plurality of reaction chambers. In some embodiments, the PCR reagent mixture is provided in a reagent mixing chamber, and the sample is mixed with the PCR reagent mixture in the reagent mixing chamber. In some embodiments, the PCR reagent mixture is provided as a lyophilized powder. In some embodiments, the sample is mixed with the PCR reagent mixture prior to transferring into the plurality of reaction chambers.

In some embodiments, the plurality of reaction chambers is each aligned at the same radial distance from a center of the rotatable disc and are equally spaced from each other. In some embodiments, the plurality of reaction chambers (e.g., cuvettes) occupies 360 degrees of arc on the rotatable disc. In some embodiments, the plurality of reaction chambers occupies a section from about 10 degrees to 100 degrees of arc on the rotatable disc. In some embodiments, the plurality of reaction chambers (e.g., cuvettes) comprises from one to 100 reaction chambers. In some embodiments, each of the plurality of reaction chambers comprises a volume of from about 5 μL to about 100 μL and further comprises a depth from about 0.1 mm to about 1.0 mm. In some embodiments, the plurality of reaction chambers comprises a depth from about 0.1 to about 0.7 mm. In some embodiments, wherein the plurality of reaction chambers comprises a depth of at most about 0.25 mm.

In some embodiments, subsequent to rotating the rotatable disc to bring the plurality of reaction chambers (e.g., cuvettes) adjacent to a second heating element, the method of the present disclosure further comprises rotating the rotatable disc to bring the plurality of reaction chambers (e.g., cuvettes) adjacent to a third heating element maintained at a third temperature. In some embodiments, the first temperature is maintained for a first period of time and the second temperature is maintained for a second period of time. In some embodiments, the third temperature is maintained for a third period of time. In some embodiments, the first period of time is selected from about 500 ms to about 2 s and the second period of time is selected from about 2 s to about 18 s. In some embodiments, the third period of time is selected from about 1 s to about 6 s. In some embodiments, the first temperature is selected from about 90 degrees C. to about 99 degrees C. and the second temperature is selected from about 50 degrees C. to about 74 degrees C. In some embodiments, the third temperature is selected from about 65 degrees C. to about 75 degrees C. In some embodiments, the first heating element comprises a first radial length, and the second heating element comprises a second radial length. In some embodiments, the second radial length is about 6 to about 9 times the first radial length. In some embodiments, the third heating element comprises a third radial length. In some embodiments, the third radial length is about 2 to about 3 times the radial length of the first radial length. In some embodiments, all blocks have the same radial length.

In some embodiments, the method further comprises stabilizing the rotatable disc at the first temperature for the first period of time, the second temperature for the second period of time and/or the third temperature for the third period of time. In some embodiments, stabilizing comprises clamping the rotatable disc between a first heating block and a second heating block of the first heating element, the second heating element or the third heating element. In some embodiments, subsequent to clamping the rotatable disc, the method further comprises unclamping the rotatable disc from the first heating block and the second heating block of the first, second, or third heating element.

In some embodiments, the excitation light is supplied by an optic head or a plurality of optic heads. In some embodiments, the optic head or plurality of optic heads further comprise one or more wavelength filters to change the first wavelength or the plurality of wavelengths for the excitation light. For example, and not by way of limitation, all excitation wavelengths are activated sequentially over an excitation time period. In some embodiments, the excitation time period is from about 200 ms to about 500 ms. In some embodiments, the excitation time period is about 350 ms. In another example, but not by way of limitation, all wavelengths are activated simultaneously by the optic head. In some embodiments, the emission light is measured on a first fluorescence detector or a plurality of fluorescence detectors. In some embodiments, the first detector or plurality of fluorescence detectors comprises one or more wavelength channels to measure an emission intensity. For example, and not by way of limitation, all wavelengths are detected or measured sequentially over a measurement time period. In some embodiments, the measurement time period is from about 200 ms to about 500 ms. In some embodiments, the measurement time period is about 350 ms. In another example, but not by way of limitation all wavelengths are measured simultaneously on the fluorescence detectors.

Another aspect of the present disclosure is directed to a method for multiplexed real-time amplification and detection of a plurality of target sequences in a rotatable disc comprising a reaction chamber, the method comprising: (a) loading a sample comprising the plurality of target sequences into the reaction chamber (e.g., cuvette); wherein the sample is mixed with a primer and/or a probe stored within the reaction chamber. (b) thermal cycling the sample mixed with the PCR reaction mixture by rotating the rotatable disc, thereby sequentially bringing the reaction chamber in proximity of a plurality of heating elements positioned adjacent to the rotatable disc, wherein each of plurality of heating elements is maintained at a denaturing temperature, an annealing temperature, or an elongation temperature; and (c) detecting a plurality of fluorescence signals from the combined sample and first PCR reaction mixture.

In some embodiments, the rotatable disc further comprises a loading chamber in fluid communication with the reaction chambers through a channel. In some embodiments, the method further comprises loading the sample into the loading chamber. In some embodiments, the channel is defined by two plastic sheets welded together by two parallel lines. In some embodiments, the channel comprises a thin plastic film with a z dimension from about 1 μm to about 1 mm.

In some embodiments, the reaction chamber (e.g., cuvette) comprises one or more reaction chambers. In some embodiments, each of the reaction chamber comprises a volume of from about 5 μL to about 100 μL and further comprises a depth from about 0.1 mm to about 1.0 mm. In some embodiments, the reaction chamber comprises a depth of at most about 0.25 mm.

In some embodiments, loading the sample into the reaction chamber comprises rotating the rotatable disc, thereby generating a sufficient centripetal force on the sample to cause the sample to flow through the channel and into the reaction chamber. In some embodiments, the sufficient centripetal force is generated by spinning the rotatable disc from about 500 RPM to about 15000 RPM.

In some embodiments, prior to thermocycling the sample, the method further comprises contacting the rotatable disc with a sealer, thereby sealing the channel and preventing fluid communication the reaction chamber (e.g., cuvette). In some embodiments, the sealer is housed within an analytical device for real-time PCR, thereby enabling a full sample-answer system by integrating a microfluidic sample preparation system with a nucleic acid processing system. In some embodiments, each reaction chamber is sealed by contact or non-contact means to avoid evaporation and escape of the heated liquid. In some embodiments, sealing of the channel is achieved via heat and pressure, via LASER welding or via ultrasonic welding. In some embodiments, sealing of the channel is achieved via heat and pressure, such as, but not limited to, by a heat sealer. In some embodiments, the sealer is a heat sealer. In some embodiments, the sealer comprises a first element configured to provide a thermal energy and a pressure on the rotatable disc and a second element configured to provide a counter force to the pressure. In some embodiments, contacting the rotatable disc with the sealer comprises applying the pressure on the rotatable disc such that the channel deforms.

In some embodiments, thermal cycling the sample mixed with comprises sequentially maintaining the reaction chamber at the denaturing temperature for about 500 ms to about 2 s, at the annealing temperature for about 3 s to about 18 s, and at the elongation temperature for about 1 s to about 6 s. In some embodiments, the denaturing temperature is selected from about 90 degrees C. to about 99 degrees C., the annealing temperature is selected from about 50 degrees C. to about 74 degrees C., and the elongation temperature is selected from about 65 degrees C. to about 75 degrees C.

In some embodiments, prior to detecting a plurality of fluorescence wavelength, the method further comprises exposing the reaction chamber to a plurality of excitation wavelengths. In some embodiments, the plurality of fluorescence signals each corresponds to one target sequence of the plurality of target sequences. In some embodiments, the plurality of excitation wavelengths and the plurality of fluorescence signals comprises one wavelength each. In some embodiments, the plurality of excitation wavelengths and the plurality of fluorescence signals comprise two or more wavelengths each. In some embodiments, the plurality of excitation wavelengths and the plurality of fluorescence signals comprise one to 10 wavelengths each. In some embodiments, the plurality of excitation wavelengths and the plurality of fluorescence signals comprise one to 6 wavelengths each. In some embodiments, the plurality of excitation wavelengths and the plurality of fluorescence signals comprise one to 4 wavelengths each. In some embodiments, the plurality of excitation wavelengths and the plurality of fluorescence signals are independently selected at each occurrence from about 400 nm to about 750 nm. In some embodiments, the plurality of excitation wavelengths and the plurality of fluorescence signals are pairs of wavelengths associated with excitation and emission from a fluorescent probe. For example, without limitation, the plurality of excitation wavelengths and the plurality of fluorescence signals can be compatible with FAM (e.g., 495 nm/520 nm), SUN (e.g., 538 nm/554 nm), TEX 615 (e.g., 596 nm/613 nm), or Cy5 (e.g., 648 nm/667 nm) detection. For example, and not by way of limitation, the plurality of excitation wavelengths can be independently selected from about 495 nm, about 538 nm, about 596 nm, and about 648 nm. For example, and not by way of limitation, the plurality of fluorescence signals can be independently selected from about 520 nm, about 554 nm, about 613 nm, and about 667 nm.

In some embodiments, the first PCR reagent mixture comprises a plurality of primers complimentary to at least a portion of the plurality of target sequences and a plurality of fluorescence probes complimentary to each of the plurality of target sequences. In some embodiments, the primer or the probe is provided as a lyophilized powder.

In some embodiments, prior to loading the sample into the reaction chamber, the method further comprises contacting the sample with a PCR reagent mixture. In some embodiments, the PCR reaction mixture comprises a polymerase and a plurality of nucleotides. In some embodiments, the PCR reagent mixture is provided in a mixing chamber of the rotatable disc and the sample is mixed with the PCR reagent mixture in the mixing chamber. In some embodiments, the PCR reagent mixture is provided as a lyophilized powder in the mixing chamber.

The present disclosure provides methods for amplifying a target nucleic acid. The method can comprise (a) providing a sample comprising the target nucleic acid in a loading chamber on a rotatable disc. The rotatable disc can further comprise a plurality of reaction chambers (e.g., cuvette) in fluid communication with the loading chamber through a channel. The method can further comprise (b) contacting the rotatable disc with a sealer within a housing of an analytic device to seal the channel. The fluid communication between the plurality of reaction chambers (e.g., cuvette) can be prevented after sealing. The method can further comprise (c) subjecting the rotatable disc to thermocycling within the housing of the analytic device, thereby amplifying the target nucleic acid.

In some embodiments, thermocycling comprises rotating the rotatable disc to bring the reaction chamber (e.g., cuvette) adjacent to a first heating element maintained at a first temperature, thereby denaturing the target nucleic acid in the sample. In some embodiments, thermocycling further comprises rotating the rotatable disc to bring the reaction chamber adjacent to a second heating element maintained at a second temperature, thereby annealing the primer to the denatured nucleic acid and replicating the target nucleic acid. In some embodiments, thermocycling further comprises rotating the rotatable disc to bring the plurality of reaction chambers (e.g., cuvettes) adjacent to a third heating element maintained at a third temperature, thereby replicating the target nucleic acid. In some embodiments, the first temperature is maintained for a first period of time. the second temperature is maintained for a second period of time, and the third temperature is maintained for a third period of time. In some embodiments, the first temperature is selected from about 90 degrees C. to about 99 degrees C., the second temperature is selected from about 50 degrees C. to about 74 degrees C., and the third temperature is selected from about 65 degrees C. to about 75 degrees C. In some embodiments, the first period of time is selected from about 500 ms to about 2 s, the second period of time is selected from about 3 s to about 18 s and, the third period of time is selected from about 1 s to about 6 s. In some embodiments, the first heating element comprises a first radial length, and the second heating element comprises a second radial length, and the third heating element comprises a third radial length. In some embodiments, second radial length is about 6 to about 9 times the first radial length and the third radial length is about 2 to about 3 times the radial length of the first radial length. In some embodiments, the method further comprises independently stabilizing the rotatable disc at the first temperature for the first period of time and the second temperature for the second period of time and the third temperature for the third period of time. In some embodiments, stabilizing comprises clamping the rotatable disc between a first heating block and a second heating block of the first heating element, the second heating element, or the third heating element. In some embodiments, the method further comprises, subsequent to stabilizing the rotatable disc, unclamping the rotatable disc from the first, second, or third heating element.

In some embodiments, subsequent to thermocycling within the housing of the device, the method further comprises exposing the reaction chamber to an excitation light of a first wavelength. In some embodiments, the method further comprises measuring an emitted light of a second wavelength from the reaction chamber. In some embodiments, the target nucleic acid comprises a plurality of different target nucleic acids. In some embodiments, the method further comprises exposing the plurality of different target nucleic acids within the reaction chamber to an excitation light of a plurality of wavelengths. In some embodiments, the excitation light of the plurality of wavelengths comprises about 400 nm to about 750 nm. In some embodiments, the method further comprises detecting an emission light of a plurality of wavelengths from the plurality of different target nucleic acids. In some embodiments, the emission light of the plurality of wavelengths comprises from about 400 nm to about 750 nm. In some embodiments, the plurality of excitation wavelengths and the plurality of fluorescence signals comprises one wavelength each. In some embodiments, the plurality of excitation wavelengths and the plurality of fluorescence signals comprise two or more wavelengths each. In some embodiments, the plurality of excitation wavelengths and the plurality of fluorescence signals comprise one to 10 wavelengths each. In some embodiments, the plurality of excitation wavelengths and the plurality of fluorescence signals comprise one to 6 wavelengths each. In some embodiments, the plurality of excitation wavelengths and the plurality of fluorescence signals comprise one to 4 wavelengths each. In some embodiments, the plurality of excitation wavelengths and the plurality of fluorescence signals are independently selected at each occurrence from about 400 nm to about 750 nm. In some embodiments, the plurality of excitation wavelengths and the plurality of fluorescence signals are pairs of wavelengths associated with excitation and emission from a fluorescent probe. For example, without limitation, the plurality of excitation wavelengths and the plurality of fluorescence signals can be compatible with FAM (e.g., 495 nm/520 nm), SUN (e.g., 538 nm/554 nm), TEX 615 (e.g., 596 nm/613 nm), or Cy5 (e.g., 648 nm/667 nm) detection. For example, and not by way of limitation, the plurality of excitation wavelengths can be independently selected from about 495 nm, about 538 nm, about 596 nm, and about 648 nm. For example, and not by way of limitation, the plurality of fluorescence signals can be independently selected from about 520 nm, about 554 nm, about 613 nm, and about 667 nm.

In some embodiments, the excitation light is supplied by an optic head or a plurality of optic heads. In some embodiments, the optic head or plurality of optic heads further comprise one or more wavelength filters to change the first wavelength or the plurality of wavelengths for the excitation light. For example, and not by way of limitation, all excitation wavelengths are activated sequentially over an excitation time period. In some embodiments, the excitation time period is from about 200 ms to about 500 ms. In some embodiments, the excitation time period is about 350 ms. In another example, but not by way of limitation, all wavelengths are activated simultaneously by the optic head. In some embodiments, two or more excitation wavelengths, selected from about 495 nm, about 538 nm, about 596 nm, and about 648 nm, are used to illuminate the reaction chambers (e.g., cuvettes) simultaneously. In some embodiments, three or more excitation wavelengths, selected from about 495 nm, about 538 nm, about 596 nm, and about 648 nm, are used to illuminate the reaction chambers (e.g., cuvettes) simultaneously. In some embodiments, all four excitation wavelengths, selected from about 495 nm, about 538 nm, about 596 nm, and about 648 nm, are used to illuminate the reaction chambers (e.g., cuvettes) simultaneously. In some embodiments, one or more filters are used to prevent crosstalk between the different wavelengths.

In some embodiments, the emission light is measured on a first fluorescence detector or a plurality of fluorescence detectors. In some embodiments, the first detector or plurality of fluorescence detectors comprises one or more wavelength channels to measure an emission intensity. For example, and not by way of limitation, all fluorescence emission wavelengths can be detected or measured sequentially over a measurement time period. In some embodiments, the measurement time period is from about 200 ms to about 500 ms. In some embodiments, the measurement time period is about 350 ms. In some embodiments, fluorescence emission wavelengths of fluorophores that substantially crosstalk are measured sequentially. In some embodiments, fluorescence emission wavelengths that substantially overlap are measured sequentially. In some embodiments, fluorescence emission wavelengths of fluorophores that substantially crosstalk or fluorescence emission wavelengths that substantially overlap are measured in separate passages of the reaction chambers through the plurality of heating elements or separate cycles of thermocycling. In some embodiments, fluorescence emission wavelengths of fluorophores that do not substantially crosstalk are measured simultaneously. In some embodiments, two or more fluorescence emission wavelengths that do not substantially overlap can be measured simultaneously. In some embodiments, fluorescence emission wavelengths of fluorophores that do not substantially crosstalk or fluorescence emission wavelengths that do not substantially overlap are measured over a single passage of the reaction chambers through the plurality of heating elements or a single cycle of thermocycling.

In some embodiments, the fluorescence emission wavelengths are measured over more than one cycle of thermocycling. In some embodiments, the fluorescence emission wavelengths are measured over more than one passage of the reaction chambers through the plurality of heating elements. For example, fluorescence signals from FAM (e.g., at 520 nm) and TEX 615 (e.g., at 613 nm) can be measured during a first passage (e.g., cycle) of the reaction chambers through the plurality of heating elements, and fluorescence signals from Cy5 (e.g., at 667 nm) and SUN (e.g., at 554 nm) can be measured during a second (e.g., cycle) of the reaction chambers through the plurality of heating elements.

In another example, but not by way of limitation, all fluorescence emission wavelengths are measured simultaneously on the fluorescence detectors. In some embodiments, all fluorescence emission wavelengths are measured in a single pass during one cycle of thermocycling. In some embodiments, all wavelengths are measured in a single pass from when the one or more reaction chambers are transferred from the heating element maintained at the annealing temperature to when the one or more reaction chambers are transferred to the heating element maintained at the denaturing temperature.

In some embodiments, the channel comprises a thermoplastic material that seals the channel when heated to a target temperature. In some embodiments, the target temperature comprises 110 to 300 degrees C.

In some embodiments, the plurality of reaction chambers contains a PCR reaction mixture. In some embodiments, the PCR reaction mixture comprises at least one of the following: a primer, a polymerase, and a plurality of nucleotides.

In some embodiments, the plurality of reaction chambers is each aligned at the same radial distance from the center of the rotatable disc and are equally spaced from each other. In some embodiments, the plurality of reaction chambers occupies 360 degrees of arc on the rotatable disc. In some embodiments, the plurality of reaction chambers occupies a section from about 10 degrees to 100 degrees of arc on the rotatable disc. In some embodiments, the plurality of reaction chambers (e.g., cuvettes) comprises from 1 to 100 reaction chambers. In some embodiments, each of the plurality of reaction chambers comprises a volume of from about 10 μL to about 100 μL. In some embodiments, each of the plurality of reaction chambers (e.g., cuvettes) comprises a depth of from about 0.1 mm to about 1.0 mm. In some embodiments, the plurality of reaction chambers (e.g., cuvettes) comprises a depth of at most about 0.25 mm.

In one aspect, the present disclosure is directed to a method for real-time polymerase chain reaction (PCR), the method comprising:

(a) loading a sample comprising a target nucleic acid into a loading chamber on a rotatable disc, the rotatable disc further comprising a plurality of reaction chambers (e.g., cuvettes) and a channel connecting the loading chamber to the plurality of reaction chambers (e.g., cuvettes); wherein the sample flows to the plurality of reaction chambers (e.g., cuvettes) via the channel following loading of the sample;

(b) contacting the rotatable disc with a sealer, thereby sealing the channel and preventing fluid communication between the plurality of reaction chambers (e.g., cuvettes) after filling;

(c) rotating the rotatable disc to bring the plurality of reaction chambers (e.g., cuvettes) adjacent to a first heating element maintained at a first temperature, thereby denaturing the target nucleic acid in the sample;

(d) rotating the rotatable disc to bring the plurality of reaction chambers (e.g., cuvettes) adjacent to a second heating element maintained at a second temperature, thereby annealing the primer to the denatured target nucleic acid and replicating the denatured target nucleic acid;

(e) rotating the rotatable disc to bring the plurality of reaction chambers (e.g., cuvettes) adjacent to the first heating element while, doing so, exposing the plurality of reaction chambers (e.g., cuvettes) to excitation light of a first wavelength, a second wavelength, a third wavelength and a fourth wavelength simultaneously (f) measuring emitted light of the first, second, third and fourth wavelength from the plurality of reaction chambers (e.g., cuvettes); and (h) repeating steps (c) through (f) until the emitted light is measured at an intensity indicating the presence of the target nucleic acid.

In another aspect, the present disclosure is directed to a method for multiplexed real-time amplification and detection of a plurality of different target nucleic acids using a rotatable disc comprising a plurality of reaction chambers (e.g., cuvettes), the method comprising:

(a) loading a sample comprising the plurality of different target nucleic acids into the rotatable disc, thereby transferring the sample to the plurality of reaction chambers (e.g., cuvettes), wherein the sample is mixed with a plurality of primers and probes, wherein each of the plurality of primers and probes are complementary to a portion of a corresponding target nucleic acid of the plurality of different target nucleic acids;

(b) rotating the rotatable disc to bring the plurality of reaction chambers (e.g., cuvettes) adjacent to a first heating element maintained at a first temperature, thereby denaturing each of the plurality of target nucleic acids in the sample;

(c) rotating the rotatable disc to bring the plurality of chambers adjacent to a second heating element maintained at a second temperature, thereby annealing the plurality of primers to the corresponding target nucleic acids denatured in (b) and replicating the plurality of different target nucleic acids;

(d) exposing the plurality of reaction chambers (e.g., cuvettes) to an excitation light comprising a plurality of excitation wavelengths;

(e) measuring an emitted light comprising a plurality of emission wavelengths from the plurality of reaction chambers (e.g., cuvettes), wherein each of the plurality of emission wavelengths corresponds to the presence of each of the plurality of different target nucleic acids; and (f) repeating steps (b) through (e) until the emitted light is measured at an intensity indicating the presence of the plurality of different target nucleic acids.

The present disclosure provides a method for multiplexed real-time amplification and detection of a plurality of different target nucleic acids in a biological sample. In one aspect, the method comprises: (a) loading a sample into a loading chamber on a rotatable disc, the rotatable disc further comprising a plurality of reaction chambers and a channel fluidly connecting the loading chamber to the plurality of reaction chambers, wherein the reaction chambers are loaded with a PCR reagent mixture comprising a plurality of primers and a plurality of fluorescent probes, wherein the sample is mixed with the plurality of primers, wherein each of the plurality of primers is complementary to a portion of a corresponding target nucleic acid of the plurality of different target nucleic acids, wherein the sample flows to the plurality of reaction chambers via the channel thereby filling the reaction chambers following loading of the sample; (b) contacting the channel within the rotatable disc with a sealer, thereby sealing the channel and preventing fluid communication between the plurality of reaction chambers after filling; (c) rotating the rotatable disc to bring the plurality of reaction chambers adjacent to a first heating element maintained at a first temperature, thereby denaturing each of the plurality of target nucleic acids in the sample if present, thereby producing a plurality of denatured target nucleic acids; (d) rotating the rotatable disc to bring the plurality of chambers adjacent to a second heating element maintained at a second temperature, thereby annealing the plurality of primers to the corresponding plurality of denatured target nucleic acids and replicating the plurality of different target nucleic acids; (e) exposing the plurality of reaction chambers to an excitation light comprising a plurality of excitation wavelengths, thereby exciting the plurality of fluorescent probes; and (f) repeating steps (c) through (e) for multiple cycles and measuring a plurality of emitted lights of a plurality of emission wavelengths from the plurality of reaction chambers, wherein each of the plurality of emission wavelengths corresponds to the presence of each of the plurality of different target nucleic acids, wherein if emitted light of an emission wavelength is detected, the sample comprises the corresponding target nucleic acid.

Devices for Sample Preparation, Processing, or Analysis

Figure 7:
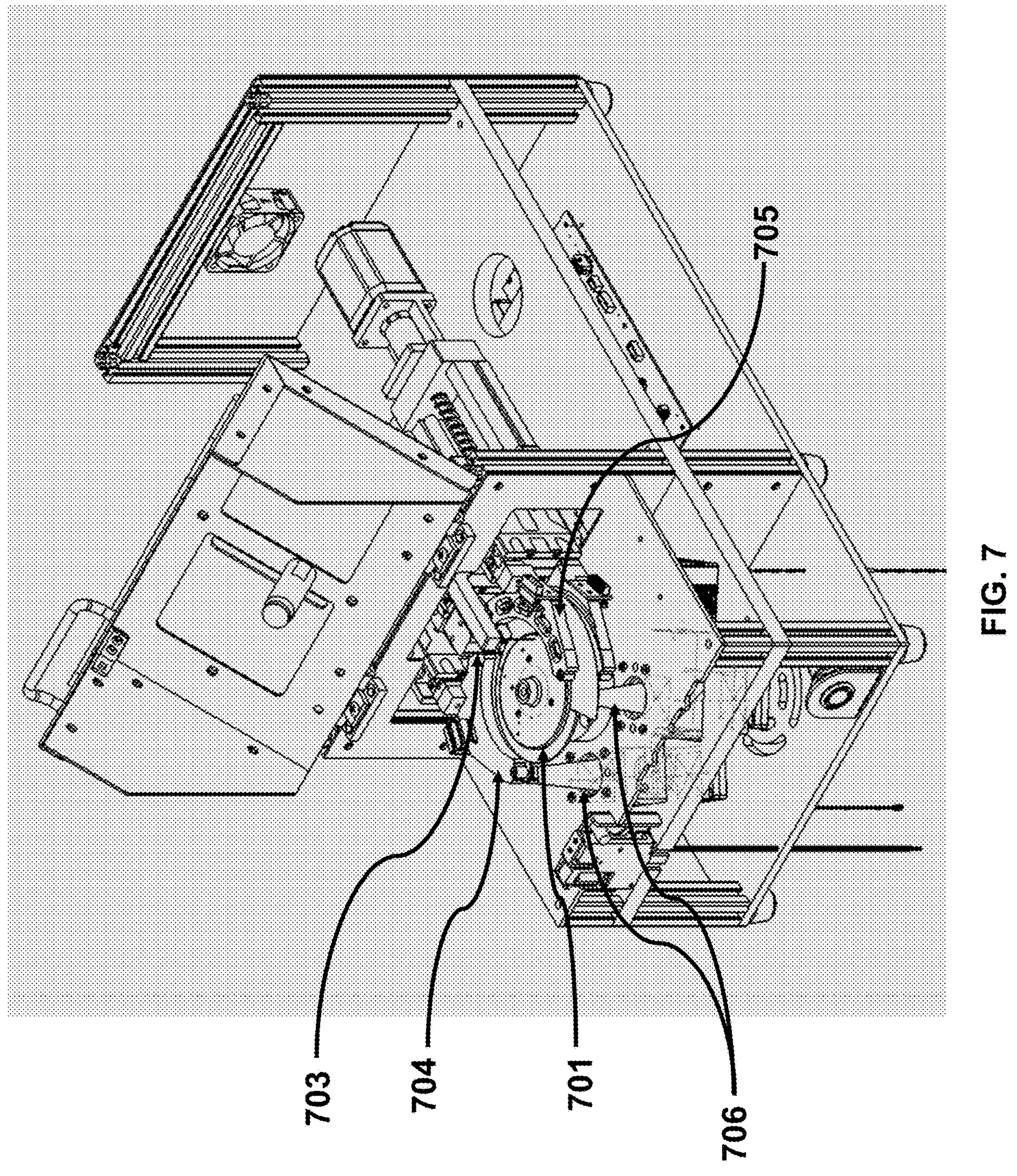
FIG. 7 illustrates a line drawing overview of an analytical device for processing a target nucleic acid.

The present disclosure provides analytical devices for preparing, processing, and/or analyzing a target nucleic acid (FIG. 7). In some embodiments, the analytical device comprises a heating chamber for sample preparation. In some embodiments, the heating chamber is connected to a downstream microfluidics network, wherein the heat-treated sample can be transferred after heating. In some embodiments, the analytical device comprises a metering chamber, a mixing chamber, one or more reaction chambers, or a combination thereof, wherein heat-treated samples undergo further processing and/or analysis. The analytical device can be or comprise a thermocycling device. For example, the analytical device can comprise one or more heating elements. In some embodiments, the one or more reaction chambers are in a rotatable disc that moves the reaction chambers from one heating element to a second heating element, thereby allowing thermocycling of the reaction chambers between different temperatures. In some embodiments, the analytical device comprises a heating element that heat seals the one or more reaction chambers after they are loaded with a reaction mixture, thereby substantially preventing evaporation or escape of the reaction mixture.

In some embodiments, the present disclosure provides a heating chamber for sample preparation. The heating chamber can be a closed heating chamber. A closed heating chamber may be used to heat a treatment sample as described elsewhere herein. A closed heating chamber may substantially prevent air and vapor from entering or leaving the chamber. In some cases, there is negligible air flow in and out of the closed heating chamber. The closed heating chamber may remain closed during hyperbaric heating. In some embodiments, the closed heating chamber is a chamber inside a heating vessel.

Figure 18:
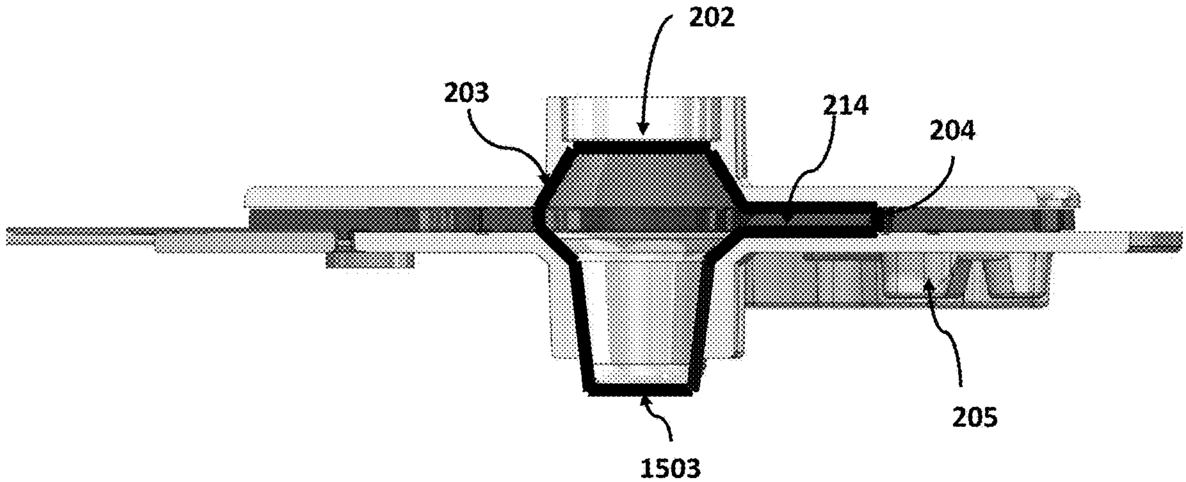
FIG. 18 illustrates a closed hyperbaric heating chamber comprising an outlet channel housed within a hyperbaric heating vessel.
Figure 19:
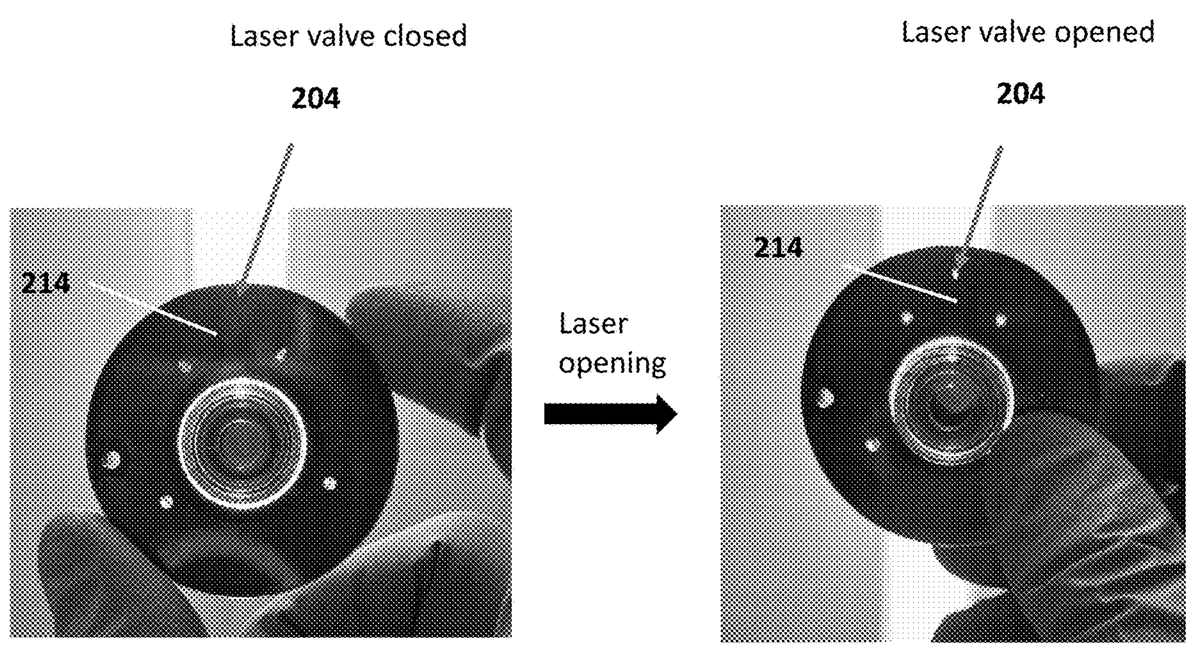
FIG. 19 provides photographs of a bottom view of a disclosed hyperbaric heating vessel illustrating a laser valve sealing the disclosed outlet channel.

In some embodiments, the closed chamber is opened at some time point to release the sample from the heating vessel. In some embodiments, the sample may be released from an outlet. The outlet may be part of an outlet channel 214 within the heating vessel (FIGS. 2, 18, 19). In some embodiments, the sample is released into a collection chamber (e.g., a metering chamber) 205 (FIGS. 2, 18). In some embodiments, the collection chamber is a part of the heating vessel. In some embodiments, the collection chamber and heating vessel are part of a fluidics network. In some cases, the metering chamber can be designed to meter multiple aliquots of sample for multiplexed sample analysis.

The heating vessel and/or closed heating chamber may be composed of different materials. In some embodiments, the heating vessel and/or closed heating chamber comprises glass. In some embodiments, the heating vessel and/or closed heating chamber comprises high temperature polycarbonate. In some embodiments, the heating vessel and/or closed heating chamber comprises a thermally conductive material. In some embodiments, the heating vessel and/or closed heating chamber comprises metal. In some embodiments, the heating vessel and/or closed heating chamber may comprise zinc, stainless steel, copper, copper alloys, gold, silver, aluminum, aluminum nitride, iron, nickel, nickel allows, cobalt, carbon fiber, platinum, brass, tungsten, silicon, silicon carbide, diamond, or graphite. In some embodiments, the heating vessel and/or closed heating chamber comprises an electrically conductive material. In some embodiments, the heating vessel and/or closed heating chamber comprises a ferromagnetic material, such as iron, nickel, cobalt. For example, the heating vessel and/or closed heating chamber may be or comprise a glass ampule, a plastic container, or a metal container. In some embodiments, the heating vessel and/or closed heating chamber comprises an induction susceptor 1503 (e.g., a metallic cup) (FIGS. 15A-15C, 16A-16B, 18) that can be used to heat the treatment sample by induction heating through contact with an induction platform 1701 (FIG. 17).

Figure 16A:
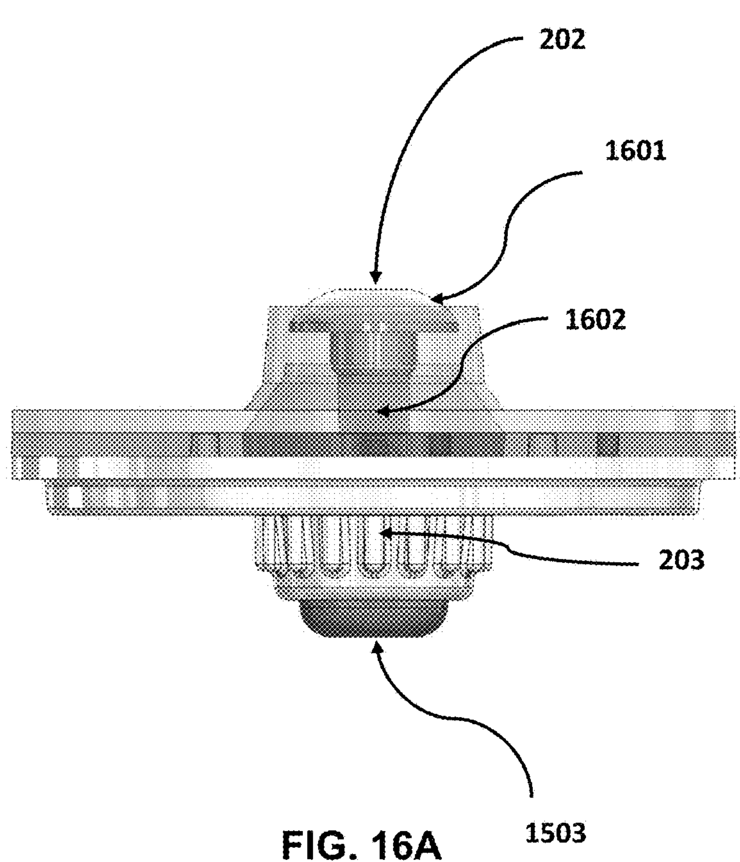
FIGS. 16A-16B illustrate a hyperbaric heating vessel, wherein the sample inlet is a duckbill valve.
Figure 16B:
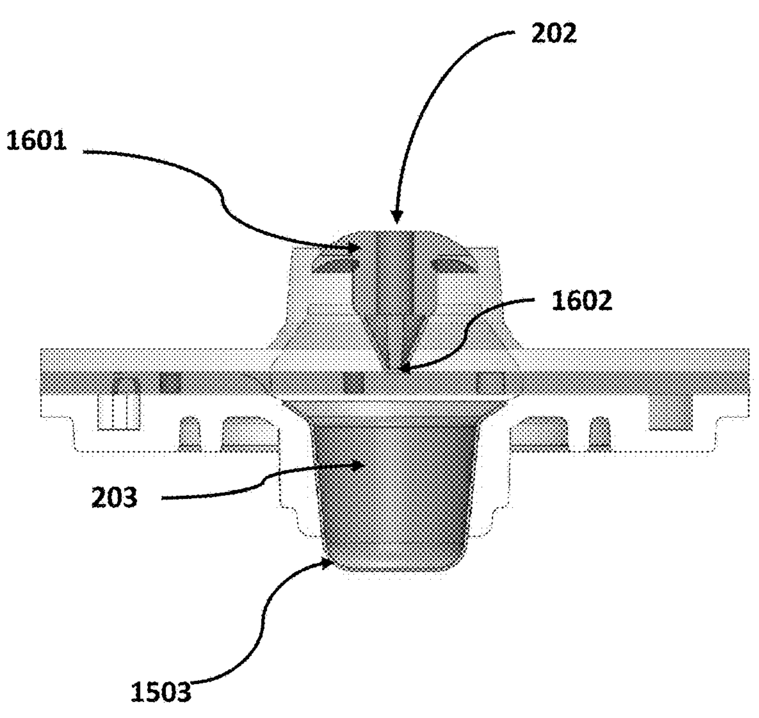
Figure 17:
FIG. 17 provides a photograph of an induction heating platform.

In some embodiments, the heating vessel comprises a heating chamber 203 that contains the treatment sample during hyperbaric heating (FIG. 16A-16B). The material of the vessel and/or heating chamber may be selected such that the heating chamber can have a temperature ramp rate of from 2 degrees Celsius per second to 50 degrees Celsius per second, from 2 degrees Celsius per second to 40 degrees Celsius per second, from 2 degrees Celsius per second to 35 degrees Celsius per second, from 2 degrees Celsius per second to 30 degrees Celsius per second, from 2 degrees Celsius per second to 25 degrees Celsius per second, from 2 degrees Celsius per second to 20 degrees Celsius per second, or from 2 degrees Celsius per second to 15 degrees Celsius per second. The material of the vessel and/or heating chamber may be selected such that the heating chamber can have a temperature ramp rate from 5 degrees Celsius per second to 60 degrees Celsius per second, from 5 degrees Celsius per second to 50 degrees Celsius per second, from 5 degrees Celsius per second to 40 degrees Celsius per second, from 5 degrees Celsius per second to 35 degrees Celsius per second, from 5 degrees Celsius per second to 30 degrees Celsius per second, from 5 degrees Celsius per second to 25 degrees Celsius per second, from 5 degrees Celsius per second to 20 degrees Celsius per second, or from 5 degrees Celsius per second to 15 degrees Celsius per second.

In some embodiments, the heating chamber is closed during hyperbaric heating and prevents air and vapor from entering or leaving the chamber. In some embodiments, the closed heating chamber remains closed in hyperbaric conditions, where the pressure inside the chamber is higher than the pressure outside the chamber. The material of the vessel or the material of the heating chamber may be selected such that the closed heating chamber can remain closed during hyperbaric heating, e.g., from room temperature to 160 degrees Celsius or when the pressure inside of the heating chamber is from 1 to 200 PSI over 1 atm.

In some embodiments, the closed heating chamber can be or comprise a glass ampule. The glass ampule may comprise a sample inlet that is fused. In other embodiments, the closed heating chamber can be or comprise a plastic container. The plastic container can comprise plastic resin or thermoresistant plastic comprising polycarbonate, high density polypropylene, PEEK, or PEI. For example, the plastic container may be a cryogenic tube or be part of a microfluidic cartridge. In further embodiments, the closed heating chamber can be or comprise a metal container. The metal container may comprise an induction susceptor (e.g., a metallic cup).

In some embodiments, the closed heating chamber is produced by sealing an open heating chamber. The sealing operation may comprise fusing an open sample inlet. The sealing operation may comprise using a cap, lid, plug, or valve. The manner of sealing the heating chamber may be selected such that the closed heating chamber may remain closed during hyperbaric heating.

In some embodiments, the heating vessel comprises a sample inlet 202 through which the sample may enter the heating chamber 203 as depicted in FIGS. 2, 15A-C, 16A-16B, 18, and 20A-20B. The sample inlet may be sealed to generate a closed heating chamber within the heating vessel. In some embodiments, the sample inlet is sealed using a cap, lid, plug, or valve. In some embodiments, the sample inlet may comprise a valve. The valve may be a one-way valve 1601 (e.g., a duckbill valve) (FIG. 16A, 16B) that allows the sample to enter the heating chamber and prevents air and/or sample from exiting the heating chamber. In some cases, the sample is introduced through the one-way valve 1601 (FIGS. 16A, 16B). The sample may be introduced manually using a pipette or injection needle. In other cases, the sample may be introduced through an automated system. The heating vessel may be part of a fluidics system and the one-way valve may be in contact with an upstream component of the fluidics system. In some embodiments, the one-way valve can further prevent air and vapor from exiting the heating chamber. The one-way valve provides a seal 1602 for the closed chamber during hyperbaric heating (FIGS. 16A, 16B).

Figure 20A:
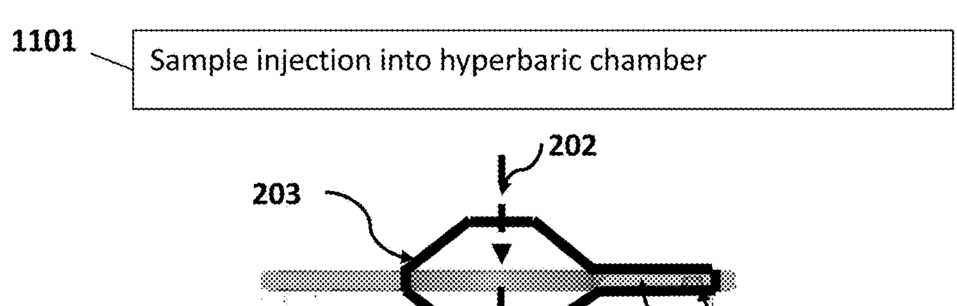
FIGS. 20A-20B illustrate the movement the sample during sample injection and sample release and zoom-in views of the laser valve.
Figure 20A:
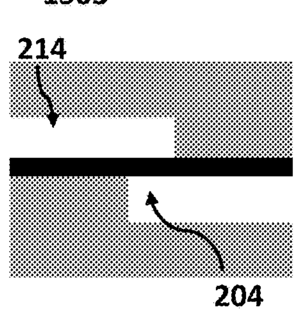
Figure 20B:
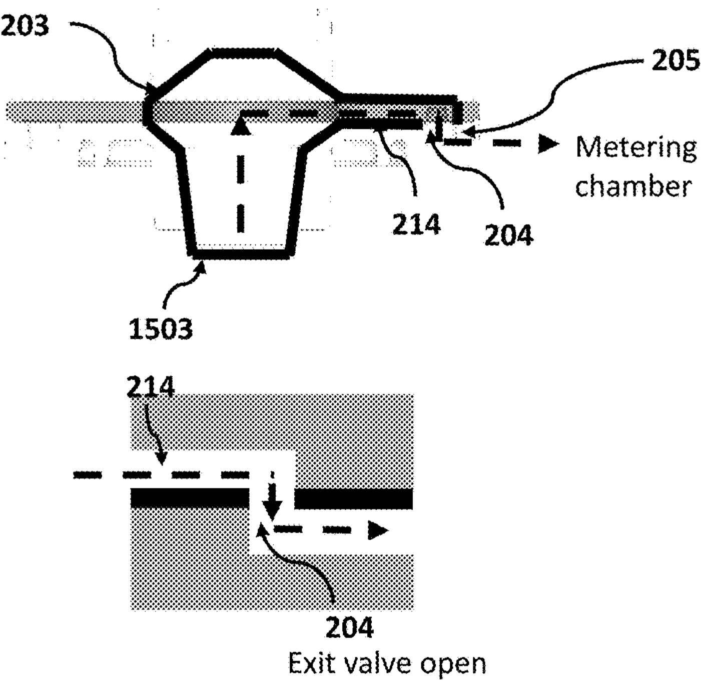

In some embodiments, the closed chamber is opened at some time point to release the sample from the heating vessel. The closed chamber may be opened after hyperbaric heating. In some embodiments, the heating chamber can be opened using mechanical forces. In some embodiments, the heating chamber is opened by removing a cap, lid, plug, or valve from an outlet. In some embodiments, heating chamber is opened by opening an exit valve 204 at the outlet. For example, the exit valve 204 may be a laser valve that is initially closed and can be opened by shining a laser beam on the valve (FIGS. 19,20A-20B). In some cases, the outlet can be the same as or in the same location as the sample inlet. In other cases, the outlet is in a separate location from the sample inlet.

In some embodiments, the sample may be released from an outlet. The outlet may be part of an outlet channel 214 within the heating vessel (FIGS. 2, 18, 19). The outlet channel 214 may comprise or be in contact with the exit valve 204 (FIGS. 2, 18, 19). The outlet channel 214 may be initially sealed by the exit valve 204, for example, during sample injection in operation 1101 in FIG. 20A and during hyperbaric heating. The outlet channel 214 may then be unsealed by opening the exit valve 204, for example, for sample release in operation 1102 in FIG. 20B. When the exit valve 204 is opened, sample may exit the heating chamber through the outlet channel 214. The sample may be propelled out of the heating chamber through the outlet channel 214 using a force, e.g., a centrifugal force. In some embodiments, the sample is released into a collection chamber (e.g., a metering chamber) 205 (FIGS. 2, 18). In some embodiments, the collection chamber is a part of the heating vessel. In some embodiments, the collection chamber and heating vessel are part of a fluidics network. The collection chamber may be a metering chamber 205 designed to meter an exact volume of sample depending on the requirements of the subsequent sample analysis. In some cases, the metering chamber is designed to meter different volumes for different sample analysis assays. In some cases, the metering chamber can be designed to meter multiple aliquots of sample for multiplexed sample analysis.

In some embodiments, the present disclosure provides analytical devices for processing and/or analyzing a target nucleic acid (FIG. 7). In some embodiments, the analytical device is a PCR device. In some embodiments, the analytical device comprises a rotatable disc (FIG. 2) that comprises a plurality of reaction chambers (e.g., cuvettes) (FIG. 2 2). The analytical device provided herein can comprise a housing. The housing can comprise: a sample holder configured to hold and rotate the rotatable disc (FIG. 7 701). The device provided herein can further comprise a sealer (FIG. 7 703) configured to seal the reaction chamber while the rotatable disc is on the sample holder. The device can further comprise a first heating element (FIG. 7 704) maintained at a first temperature configured to heat the rotatable disc to the first temperature. The device can further comprise a second heating element (FIG. 7 705) maintained at a second temperature configured to heat the rotatable disc to the second temperature.

In some embodiments, the analytical device further comprises a rotatable platform capable of spinning at a speed up to 15000 RPM. In some embodiments, the analytic device comprises the rotatable disc held within the sample holder. In some embodiments, the rotatable disc further comprises a loading chamber (e.g., a heating chamber) (FIG. 2 203) and a channel (FIG. 2 208) connecting the loading chamber to the plurality of reaction chambers (e.g., cuvettes) (FIG. 2 209). In some embodiments, the loading chamber is or comprises a heating chamber.

In some embodiments, the sealer is housed within an analytical device for real-time PCR, thereby enabling a full sample-answer system by integrating a microfluidic sample preparation system with a nucleic acid processing system. In some embodiments, each reaction chamber is sealed by contact or non-contact means to avoid evaporation and escape of the heated liquid. In some embodiments, sealing of the channel is achieved via heat and pressure, via LASER welding or via ultrasonic welding. In some embodiments, sealing of the channel is achieved via heat and pressure, such as, but not limited to, by a heat sealer. In some embodiments, the sealer is a heat sealer. In some embodiments, the sealer comprises a first element configured to provide a thermal energy and a pressure on the rotatable disc and a second element configured to provide a counter force to the pressure. In some embodiments, contacting the rotatable disc with the sealer comprises applying the pressure on the rotatable disc such that the channel deforms.

In some embodiments, the plurality of reaction chambers (e.g., cuvettes) comprises a first PCR reaction mixture comprising a primer and a fluorescent probe. In some embodiments, a mixing chamber comprises a second PCR reaction mixture comprising a polymerase, and a plurality of nucleotides.

In some embodiments, the plurality of reaction chambers (e.g., cuvettes) comprises a volume of from about 10 μL to about 100 μL and a depth of from about 0.1 mm to about 1.0 mm. In some embodiments, each of the plurality of reaction chambers (e.g., cuvettes) comprises a depth at most 0.25 mm. In some embodiments, the plurality of reaction chambers (e.g., cuvettes) comprises from one to 100 reaction chambers (e.g., cuvettes). In some embodiments, the channel comprises a z dimension from about 1 μm to about 1 mm and a width from about 1 mm to about 5 mm. In some embodiments, an aspect ratio of each of the plurality of reaction chambers (e.g., cuvettes) to the channel is at least 10 to 1.

In some embodiments, each of the plurality of reaction chambers (e.g., cuvettes) has an interior and an exterior. In some embodiments, each of the plurality of reaction chambers (e.g., cuvettes) is compatible with transmitting an excitation light of a plurality of wavelengths from the exterior of the plurality of reaction chambers (e.g., cuvettes) and the plurality of reaction chambers (e.g., cuvettes) is compatible with transmitting an emitted light of a plurality of wavelengths from the interior of the plurality of reaction chambers (e.g., cuvettes).

In some embodiments, the channel comprises a thermoplastic material that seals the channel when heated to a temperature of 110 to 300 degrees C. In some embodiments, the rotatable disc comprises a thermoformed film and a sealing film that come together to form the plurality of reaction chambers (e.g., cuvettes). In some embodiments, the thermoformed film forms a shape and a size for the plurality of reaction chambers (e.g., cuvettes). In some embodiments, the thermoformed film has a Tg higher than about 100 degrees C. In some embodiments, the sealing film and thermoformed film comprise a resin. In some embodiments, the resin comprises a single polymer. In some embodiments, the resin comprises an inner polymer and an outer polymer, and the inner polymer has a lower Tg than the outer polymer. In some embodiments, the single polymer, the inner polymer, and the outer polymer are each independently selected from polyolefin, polycarbonate, polystyrene, polymethyl methylacrylate, polyethylene, and polypropylene. In some embodiments, the resin for the sealing film and the resin for the thermoformed film is heat sealed together. In some embodiments, the resin for the sealing film and thermoformed films is the same.

In some embodiments, the first heating element comprises a first radial length and the second heating element has a second radial length and the second radial length is about 6 to about 9 times the radial length of the first radial length. In some embodiments, the analytical device further comprises a third heating element maintained at a third temperature configured to heat the rotatable disc to the third temperature. In some embodiments, the third radial length is about 2 to about 3 times the radial length of the first radial length. In some embodiments, the first heating element, the second heating element, and the third heating element, each independently comprise a pair of heating blocks designed to clamp the rotatable disc between them.

In some embodiments, the analytical device (FIG. 7) further comprises a plurality of optic heads (FIG. 7 706). In some embodiments, the plurality of optic heads provides an excitation light source of one or more wavelengths. In some embodiments, the excitation light source comprises one wavelength each. In some embodiments, the excitation light source comprises two or more wavelengths each. In some embodiments, the excitation light source comprises one to 10 wavelengths each. In some embodiments, the excitation light source comprises one to 6 wavelengths each. In some embodiments, the excitation light source comprises one to 4 wavelengths each. In some embodiments, the excitation light source is independently selected at each occurrence from about 400 nm to about 750 nm. In some embodiments, the excitation light source is associated with excitation for fluorescent probe. For example, and not by limitation, the excitation light source can be compatible with FAM (e.g., 495 nm/520 nm), SUN (e.g., 538 nm/554 nm), TEX 615 (e.g., 596 nm/613 nm), or Cy5 (e.g., 648 nm/667 nm) detection. For example, and not by way of limitation, the excitation light source can be independently selected from about 495 nm, about 538 nm, about 596 nm, and about 648 nm.

In some embodiments, the optic head further comprises a plurality of filters to add one or more wavelengths to the excitation light source. In some embodiments, the analytical device further comprises a fluorescence detector to measure an emission intensity for one or more wavelengths. In some embodiments, wherein the fluorescence detector can measure the emission intensity of more than one wavelength simultaneously.

In another aspect, the present disclosure is directed to an analytical device for processing a target nucleic acid comprising a housing, wherein the housing comprises:

- a sample holder configured to hold and rotate a rotatable disc comprising a plurality of reaction chambers (e.g., cuvettes);
- a sealer configured to seal the channel connecting the reaction chamber while the rotatable disc is on the sample holder;
- a first heating element maintained at a first temperature configured to heat the rotatable disc to the first temperature; and
- a second heating element maintained at a second temperature configured to heat the rotatable disc to the second temperature.

Rotatable Discs for Sample Processing or Analysis

The present disclosure also provides rotatable discs (FIG. 2) for sample processing or analysis. The rotatable disc can comprise a loading chamber 203 (e.g., hyperbaric heating chamber). The loading chamber can be a heating chamber (e.g., configured for hyperbaric heating of a sample), as described elsewhere herein. The rotatable disc can comprise one or more reaction chambers (e.g., cuvettes) 209. In some embodiments, each of the reaction chambers is aligned at the same radial distance from the center of the rotatable disc. In some embodiments, a plurality of reaction chambers are aligned at different radial distances from the center of the rotatable disc. The rotatable disc can further comprise a channel 208 connecting the loading chamber (e.g., hyperbaric heating chamber) to the plurality of reaction chambers (e.g., cuvettes). In some embodiments, the rotatable disc further comprises one or more intermediate chambers (e.g., a metering chamber or a mixing chamber) between the loading chamber and the one or more reaction chambers, wherein the one or more intermediate chambers are in fluid communication with the loading chamber and one or more reaction chambers. In some cases, the channel connects the loading chamber, the one or more intermediate chambers, and the one or more reaction chambers.

In some cases, the rotatable disc comprises a loading chamber configured to seal a sample in a hyperbaric condition to a temperature above 100 degrees Celsius, as described elsewhere herein. In some cases, the loading chamber is configured to seal a sample in a hyperbaric condition to a temperature from 101 degrees Celsius to 160 degrees Celsius. The loading chamber can be configured to be heated by induction heating, as described elsewhere herein. In some cases, the loading chamber comprises one or more additives, as described elsewhere herein (e.g., a chelating agent, a single stranded nucleic acid binding protein, a reducing agent, a stabilizer, or a combination thereof). In some cases, the loading chamber comprises a one-way valve (e.g., a duckbill valve), as described elsewhere herein. The loading chamber can be a closed chamber during hyperbaric heating and substantially prevent air from exiting the chamber. The loading chamber can comprise an exit valve (e.g., laser valve) that is configured to open after hyperbaric heating. In some cases, the loading chamber comprises or is connected to a channel, through which a sample can exit upon opening of the exit valve.

In some cases, the rotatable disc comprises a metering chamber 205 (FIG. 2). In some cases, the metering chamber is located downstream of the loading chamber (e.g., heating chamber). In some cases, the metering chamber is connected to the loading chamber via a channel. A valve can be located between the loading chamber and metering chamber to control the flow of the sample (e.g., heat treated sample) from the loading chamber to the metering chamber. The metering chamber can be configured to meter a specific volume of sample to one or more downstream chambers in fluid communication with the metering chamber. In some cases, the volume is configured depending on the requirements of a sample processing and/or analysis assay. In some cases, the metering chamber is connected to the one or more reaction chambers via a channel and is configured to meter a specific volume of sample to the one or more reaction chambers. In some cases, the metering chamber is connected to an intermediate chamber, such as a mixing chamber, and is configured to meter a specific volume of sample to the intermediate chamber. In some embodiments, the rotatable disc further comprises an overflow chamber 213 (FIG. 2) in fluid communication with the metering chamber, wherein the overflow chamber is configured to accept excess volume of sample that is not metered and is not transferred to a reaction chamber. In some embodiments, the rotatable disc comprises a mixing chamber 207 (FIG. 2) that is in fluid communication with the loading chamber and the one or more reaction chambers. In some cases, the mixing chamber is further in fluid communication with a metering chamber. In some cases, the mixing chamber is located downstream of the loading chamber and/or metering chamber and upstream of the one or more reaction chambers. In some cases, a channel connects the mixing chamber to loading chamber and the one or more reaction chambers. In some cases, the channel further connects the mixing chamber to the metering chamber.

In some embodiments, the one or more reaction chambers (e.g., cuvettes) comprises a volume of from about 5 μL to about 100 μL. In some embodiments, the one or more reaction chambers (e.g., cuvettes) comprises a depth of from about 0.1 mm to about 1.0 mm. In some embodiments, the one or more reaction chambers (e.g., cuvettes) comprises a depth from about 0.2 to about 0.7 mm. In some embodiments, the one or more reaction chambers (e.g., cuvettes) comprises a depth of at most 0.25 mm. In some embodiments, the one or more reaction chambers (e.g., cuvettes) are equally spaced from each other. In some embodiments, a plurality of reaction chambers (e.g., cuvettes) occupies 360 degrees of arc on the rotatable disc. In some embodiments, the plurality of reaction chambers (e.g., cuvettes) occupies a section from about 10 degrees to 100 degrees of arc on the rotatable disc. In some embodiments, the plurality of reaction chambers (e.g., cuvettes) comprises from one to 100 reaction chambers (e.g., cuvettes). In some embodiments, each of the plurality of reaction chambers (e.g., cuvettes) has an interior and an exterior. In some embodiments, each of the plurality of reaction chambers (e.g., cuvettes) is compatible with transmitting an excitation light of a plurality of wavelengths from the exterior of the plurality of reaction chambers (e.g., cuvettes) and the plurality of reaction chambers (e.g., cuvettes) is compatible with transmitting an emitted light of a plurality of wavelengths from the interior of the plurality of reaction chambers (e.g., cuvettes).

In some embodiments, the rotatable disc comprises a thermoformed film and a sealing film that are coupled together to form the plurality of reaction chambers (e.g., cuvettes). In some embodiments, the thermoformed film forms a shape and a size for the plurality of reaction chambers (e.g., cuvettes) and a shape and size for the channel. In some embodiments, the sealing film is sealed to the thermoformed film. In some embodiments, the sealing film is sealed to the thermoformed film via a skeleton 607 with two faces coextruded with heat sealed compliant material. In some embodiments, the thermoformed film comprises a thickness of from about 50 μm to about 500 μm. In some embodiments, a ratio of the width of the channel to the thickness of the thermoformed film is greater than two. In some embodiments, the sealing film comprises a thickness of from about 10 μm to about 500 μm. In some embodiments, the thermoformed film has a Tg higher than about 100 degrees C.

In some embodiments, the sealing film and thermoformed film comprise a resin. In some embodiments, the resin comprises a single polymer. In some embodiments, the resin comprises an inner polymer and an outer polymer, and the inner polymer has a lower Tg than the outer polymer. In some embodiments, the single polymer, the inner polymer, and the outer polymer are each independently selected from polyolefin, polycarbonate, polystyrene, polymethyl methylacrylate, polyethylene, and polypropylene. In some embodiments, the resin for the sealing film and the resin for the thermoformed film can be heat sealed together. In some embodiments, the resin for the sealing film and thermoformed films is the same.

In some embodiments, a channel connects the loading chamber, the metering chamber, the mixing chamber, or a combination thereof to the one or more reaction chambers. In some embodiments, the channel comprises a z dimension from about 1 μm to about 1 mm, a width from about 1 mm to about 5 mm, and a depth of at most about 200 μm. In some embodiments, the channel comprises a width from about 2 mm to about 4 mm and a depth of at most about 100 μm. In some cases, the channel has a depth from 10 μm to 500 μm, from 20 to 400 μm, from 30 to 300 μm, from 40 to 200 μm, or from 50 to 100 μm. In some embodiments, the rotatable disc further comprises an aspect ratio of each of the plurality of reaction chambers (e.g., cuvettes) to the channel wherein the aspect ratio is at least 10 to 1. In some embodiments, the rotatable disc further comprises an aspect ratio of each of the plurality of reaction chambers (e.g., cuvettes) to the channel wherein the aspect ratio is at least 20 to 1.

In some embodiments, the channel comprises a thermoplastic material. In some embodiments, the thermoplastic material has a thickness from about 10 μm to about 400 μm. In some cases, the thermoplastic material seals the channel when heated to a temperature of from 110 to 300 degrees Celsius, from 120 to 280 degrees Celsius, or from 130 to 260 degrees Celsius. In some embodiments, the thermoplastic material is selected from polycarbonate, polypropylene, polyethylene terephthalate, and cyclic olefin copolymer. In some cases, the channel comprises a thermoformed thermoplastic film sealed to a sealing thermoplastic film. In some cases, the channel is heat sealed by compressing a thermoformed film of a ceiling of the channel in contact with a sealing film of a floor of the channel. In some cases, the channel comprises coextrude thermoplastic film with an inner thermoplastic film layer having a lower Tg than an outer thermoplastic film layer. In some cases, the inner layer is configured to seal the channel when heated to a temperature of 110 to 300 degrees Celsius, from 120 to 280 degrees Celsius, or from 130 to 260 degrees Celsius. In some cases, the inner layer is configured to seal the channel by compression of the inner thermoplastic film layer and the outer layer.

Systems

The present disclosure also provides systems for sample processing or analysis. For example, the system can be used to subject a sample containing a target nucleic acid molecule for nucleic acid amplification. The nucleic acid amplification can comprise a real-time polymerase chain reaction (PCR). The system can comprise: (a) a rotatable disc comprising a loading chamber, a plurality of reaction chambers (e.g., cuvettes), and a channel connecting the loading chamber to the plurality of reaction chambers. The system can comprise (b) a sample holder for holding the rotatable disc in a substantially horizontal plane. The system can comprise a device configured to rotate the rotatable disc within the substantially horizontal plane. The system can further comprise (c) a sealer. The sealer can be coupled to an actuator that moves the sealer, thereby changing a distance between the sealer and the rotatable disc. The system can comprise (d) a first heating element maintained at a first temperature located in close proximity of a second portion of the rotatable disc. The system can comprise (e) a second heating element maintained at a second temperature located in close proximity of a second portion of the rotatable disc. The system can comprise (f) a light source oriented to generate an excitation light of a first wavelength into the horizontal plane occupied by the reaction chambers (e.g., cuvettes) of the rotatable disc. The system can comprise (g) a light detector oriented to detect emitted light of a second wavelength emitted from the reaction chambers (e.g., cuvettes) of the rotatable dis. In various embodiments, when a liquid sample comprising a nucleic acid is loaded into the loading chamber, the liquid sample can flow to the plurality of reaction chambers (e.g., cuvettes) via the channel. The liquid sample can be mixed with a PCR reagent mixture comprising a primer, a polymerase, and a plurality of nucleotides. The rotatable disc can be brought in contact with the heat sealer, thereby sealing the channel and preventing fluid communication between the plurality of reaction chambers (e.g., cuvettes). The rotatable disc can be rotated in the substantially horizontal plan to (i) bring the plurality of reaction chambers (e.g., cuvettes) adjacent to the first heating element, thereby denaturing the nucleic acid in the sample, (ii) bring the plurality of reaction chambers (e.g., cuvettes) adjacent to the second heating element, thereby annealing the primer to the denatured nucleic acid and replicating the nucleic acid; and/or (iii) orient the rotatable disc such that the excitation light generated by the light source enters the reaction chamber, thereby generating the emitted light that is emitted from the reaction chamber and detected by the light chamber.

In another aspect, the present disclosure is directed to a system for real-time polymerase chain reaction (PCR) comprising:

(a) a rotatable disc comprising a loading chamber, a plurality of reaction chambers (e.g., cuvettes), and a channel connecting the loading chamber to the plurality of reaction chambers;

(b) a sample holder for holding the rotatable disc in a substantially horizontal plane, the device configured to rotate the rotatable disc within the substantially horizontal plane;

(c) a sealer and coupled to an actuator that moves the sealer, thereby changing a distance between the sealer and the rotatable disc;

(d) a first heating element maintained at a first temperature located in close proximity of a second portion of the rotatable disc;

(e) a second heating element maintained at a second temperature located in close proximity of a second portion of the rotatable disc, (f) a light source oriented to generate an excitation light of a first wavelength into the horizontal plane occupied by the reaction chambers of the rotatable disc; and (g) a first light detector oriented to detect emitted light of a second wavelength emitted from the reaction chambers of the rotatable disc.

In another aspect, the present disclosure provides a system for real-time polymerase chain reaction (PCR) comprising: (a) a rotatable disc comprising a loading chamber, a plurality of reaction chambers, and a channel connecting the loading chamber to the plurality of reaction chambers, wherein the loading chamber is configured to be heated by induction heating; and (b) an analytical device, comprising: (i) a sample holder for receiving the rotatable disc in a substantially horizontal plane, the sample holder configured to rotate the rotatable disc within the substantially horizontal plane; (ii) a first heating element configured to contact the reaction chambers and heat the plurality of reaction chambers to a first temperature; and (iii) a second heating element configured to contact the reaction chambers and heat the plurality of reaction chambers to a second temperature.

In one aspect, the present disclosure provides a system for real-time polymerase chain reaction (PCR) comprising: (a) a rotatable disc comprising a loading chamber, a plurality of reaction chambers, and a channel connecting the loading chamber to the plurality of reaction chambers; and (b) an analytical device comprising: (i) a sample holder for receiving the rotatable disc in a substantially horizontal plane, the sample holder configured to rotate the rotatable disc within the substantially horizontal plane; (ii) a first heating element configured to heat the loading chamber to a first temperature above 100 degrees Celsius; (iii) a second heating element configured to contact the reaction chambers and heat the plurality of reaction chambers to a second temperature; and (iv) a third heating element configured to contact the reaction chambers and heat the plurality of reaction chambers to a third temperature.

In some cases, the system comprises a second light detector oriented to detect emitted light of a third wavelength emitted from the reaction chambers of the rotatable disc. In some cases, the system comprises a third light detector oriented to detect emitted light of a fourth wavelength emitted from the reaction chambers of the rotatable disc. In some cases, the first light detector, the second light detector, and the third light detector are different light detectors. In some cases, the first light detector, the second light detector, and the third light detector are the same light detector.

In some cases, when a liquid sample comprising a nucleic acid flows from the loading chamber to the plurality of reaction chambers via channel, the rotatable disc is brought in contact with the heat sealer, thereby sealing the channel and preventing fluid communication between the plurality of reaction chambers. In some cases, the rotatable disc is rotated in the substantially horizontal plane to (i) bring the plurality of reaction chambers adjacent to the first heating element, thereby denaturing the nucleic acid in the sample, (ii) bring the plurality of reaction chambers adjacent to the second heating element, thereby annealing the primer to the denatured nucleic acid and replicating the nucleic acid; and (iii) orient the rotatable disc such that the excitation light generated by the light source enters the reaction chamber, thereby generating the emitted light that is emitted from the reaction chamber and detected by the light detector.

In some cases, the system comprises one or more PCR reagents that mixes with the liquid sample. In some cases, the system comprises one or more PCR reagents in the loading chamber. In some cases, the system further comprises a mixing chamber situated in fluid communication between the loading chamber and the reaction chambers, wherein the liquid sample from the loading chamber mixes with one or more PCR reagents or a PCR reagent mixture. In some cases, the system further comprises one or more PCR reagents that are preloaded in a reaction chamber, wherein the one or more PCR reagents mixes with the sample. The one or more PCR reagents can comprise a polymerase or a plurality of nucleotides, a primers, a probe, or a combination thereof. In some embodiments, the loading chamber or mixing chamber comprises a first PCR reaction mixture, comprising a polymerase and a plurality of nucleotides, and the reaction chamber comprises a second PCR reaction mixture comprising a primer and a probe. In some embodiments, the loading chamber or mixing chamber comprises a PCR reaction mixture, comprising a primer, a polymerase, and a plurality of nucleotides, and the reaction chamber comprises a probe.

In some aspects, the present disclosure provides a system for real-time polymerase chain reaction (PCR) comprising a rotatable disc comprising a loading chamber, a plurality of reaction chambers, and a channel connecting the loading chamber to the plurality of reaction chambers. In some cases, the loading chamber is centrally located on the rotatable disc. In some cases, the plurality of reaction chambers is located on the periphery of the rotatable disc. In some cases, the loading chamber is configured to be heated by induction heating, as described elsewhere herein. In some cases, the loading chamber comprises a chelating agent, a single stranded nucleic acid binding protein, a reducing agent, a stabilizer, or a combination thereof, as described elsewhere herein.

In some cases, the system further comprises an analytical device, comprising a sample holder for receiving the rotatable disc in a substantially horizontal plane, the sample holder configured to rotate the rotatable disc within the substantially horizontal plane. In some cases, the analytical device comprises a first heating element configured to contact the reaction chambers and heat the plurality of reaction chambers to a first temperature, and a second heating element configured to contact the reaction chambers and heat the plurality of reaction chambers to a second temperature. In some cases, the analytical device further comprises a third heating element configured to heat the loading chamber to a temperature above 100 degrees Celsius. In some cases, the third heating element is configured to heat the loading chamber to a temperature from 101 degrees Celsius to 160 degrees Celsius. In some cases, the third heating element is configured to heat the loading chamber at temperature ramp rate of from 0.5 degrees Celsius per second to 50 degrees Celsius per second, from 0.5 degrees Celsius per second to 40 degrees Celsius per second, from 0.5 degrees Celsius per second to 35 degrees Celsius per second, from 0.5 degrees Celsius per second to 30 degrees Celsius per second, from 0.5 degrees Celsius per second to 25 degrees Celsius per second, from 0.5 degrees Celsius per second to 20 degrees Celsius per second, from 0.5 degrees Celsius per second to 15 degrees Celsius per second, from 2 degrees Celsius per second to 50 degrees Celsius per second, from 2 degrees Celsius per second to 40 degrees Celsius per second, from 2 degrees Celsius per second to 35 degrees Celsius per second, from 2 degrees Celsius per second to 30 degrees Celsius per second, from 2 degrees Celsius per second to 25 degrees Celsius per second, from 2 degrees Celsius per second to 20 degrees Celsius per second, from 2 degrees Celsius per second to 15 degrees Celsius per second, from 5 degrees Celsius per second to 50 degrees Celsius per second, from 5 degrees Celsius per second to 40 degrees Celsius per second, from 5 degrees Celsius per second to 35 degrees Celsius per second, from 5 degrees Celsius per second to 30 degrees Celsius per second, from 5 degrees Celsius per second to 25 degrees Celsius per second, from 5 degrees Celsius per second to 20 degrees Celsius per second, or from 5 degrees Celsius per second to 15 degrees Celsius per second. In some cases, the analytical device further comprises a light source oriented to generate an excitation light of a first wavelength into the horizontal plane occupied by the plurality of reaction chambers of the rotatable disc. In some cases, the analytical device further comprises a light detector oriented to detect emitted light of a second wavelength emitted from the plurality of reaction chambers of the rotatable disc.

Additional Methods and Devices

The present disclosure provides a method for multiplexed real-time amplification and detection of a plurality of target sequences in a rotatable disc comprising a reaction chamber, the method comprising: (a) loading a sample comprising the plurality of target sequences into the reaction chamber; wherein the sample is mixed with a primer and/or a probe stored within the reaction chamber; (b) thermal cycling the sample mixed with the PCR reaction mixture by rotating the rotatable disc, thereby sequentially bringing the reaction chamber in proximity of a plurality of heating elements positioned adjacent to the rotatable disc, wherein each of plurality of heating elements is maintained at a denaturing temperature, an annealing temperature, or an elongation temperature; and (c) detecting a plurality of fluorescence signals from the combined sample and first PCR reaction mixture.

In some embodiments, the reaction chamber comprises one or more reaction chambers. In some embodiments, thermal cycling the sample comprises sequentially maintaining the reaction chamber at the denaturing temperature for about 500 ms to about 2 s, at the annealing temperature for about 3 s to about 18 s, and at the elongation temperature for about 1 s to about 6 s. In some embodiments, the denaturing temperature is selected from about 90 degrees C. to about 99 degrees C., the annealing temperature is selected from about 50 degrees C. to about 74 degrees C., and the elongation temperature is selected from about 65 degrees C. to about 75 degrees C. In some embodiments, the rotatable disc further comprises a loading chamber in fluid communication with the reaction chambers through a channel. In some embodiments, the method further comprises, prior to (a), loading the sample into the loading chamber. In some embodiments, loading the sample into the reaction chamber in (a) comprises rotating the rotatable disc, thereby generating a sufficient centripetal force on the sample to cause the sample to flow through the channel and into the reaction chamber. In some embodiments, the sufficient centripetal force is generated by spinning the rotatable disc from about 500 RPM to about 15000 RPM. In some embodiments, the channel is defined by two plastic sheets welded together by two parallel lines. In some embodiments, the channel comprises a thin plastic film with a z dimension from about 1 μm to about 1 mm. In some embodiments, the method further comprises, prior to (b), contacting the rotatable disc with a sealer, thereby sealing the channel and preventing fluid communication the reaction chamber. In some embodiments, the sealer is a heat sealer. In some embodiments, each of the reaction chambers comprise a volume of from about 5 μL to about 100 μL and further comprises a depth from about 0.1 mm to about 1.0 mm. In some embodiments, the reaction chamber comprises a depth of at most about 0.25 mm. In some embodiments, the method further comprises, prior to (c), exposing the reaction chamber to a plurality of excitation wavelengths. In some embodiments, each of the plurality of excitation wavelengths and the plurality of fluorescence signals has a wavelength each independently selected at each occurrence from about 400 nm to about 750 nm. In some embodiments, the plurality of fluorescence signals each corresponds to one target sequence of the plurality of target sequences. In some embodiments, the first PCR reagent mixture comprises a plurality of primers complimentary to at least a portion of the plurality of target sequences and a plurality of fluorescence probes complimentary to each of the plurality of target sequences. In some embodiments, the primer or the probe is provided as a lyophilized powder. In some embodiments, the method further comprises, prior to loading the sample into the reaction chamber, contacting the sample with a PCR reagent mixture. In some embodiments, the PCR reaction mixture comprises a polymerase and a plurality of nucleotides. In some embodiments, the PCR reagent mixture is provided in a mixing chamber of the rotatable disc and the sample is mixed with the PCR reagent mixture in the mixing chamber. In some embodiments, the PCR reagent mixture is provided as a lyophilized powder in the mixing chamber.

The present disclosure provides a method for amplifying a target nucleic acid, the method comprising: (a) providing a sample comprising the target nucleic acid in a loading chamber on a rotatable disc, wherein the rotatable disc further comprises a plurality of reaction chambers in fluid communication with the loading chamber through a channel; (b) contacting the rotatable disc with a sealer within a housing of an analytic device to seal the channel, thereby preventing fluid communication between the plurality of reaction chambers; and (c) subjecting the rotatable disc to thermocycling within the housing of the analytic device, thereby amplifying the target nucleic acid.

In some embodiments, thermocycling in (c) comprises rotating the rotatable disc to bring the reaction chamber adjacent to a first heating element maintained at a first temperature, thereby denaturing the target nucleic acid in the sample. In some embodiments, thermocycling in (c) comprises rotating the rotatable disc to bring the reaction chamber adjacent to a second heating element maintained at a second temperature, thereby annealing the primer to the denatured nucleic acid and replicating the target nucleic acid. In some embodiments, thermocycling in (c) further comprises rotating the rotatable disc to bring the plurality of reaction chambers adjacent to a third heating element maintained at a third temperature, thereby replicating the target nucleic acid. In some embodiments, the method further comprises, subsequent to (c), exposing the reaction chamber to an excitation light of a first wavelength. In some embodiments, the method further comprises measuring an emitted light of a second wavelength from the reaction chamber. In some embodiments, the target nucleic acid comprises a plurality of different target nucleic acids. In some embodiments, the method further comprises exposing the plurality of different target nucleic acids within the reaction chamber to an excitation light of a plurality of wavelengths. In some embodiments, the excitation light of the plurality of wavelengths comprises about 400 nm to about 750 nm. In some embodiments, the method further comprises detecting an emission light of a plurality of wavelengths from the plurality of different target nucleic acids. In some embodiments, the emission light of the plurality of wavelengths comprises from about 400 nm to about 750 nm. In some embodiments, the channel comprises a thermoplastic material that seals the channel when heated to a target temperature. In some embodiments, the target temperature is from 110 to 300 degrees C. In some embodiments, the plurality of reaction chambers contains a PCR reaction mixture. In some embodiments, the PCR reaction mixture comprises a PCR reagent selected from the group consisting of: a primer, a polymerase, and a plurality of nucleotides. In some embodiments, the plurality of reaction chambers are each aligned at the same radial distance from the center of the rotatable disc and are equally spaced from each other. In some embodiments, the plurality of reaction chambers occupies 360 degrees of arc on the rotatable disc. In some embodiments, the plurality of reaction chambers occupies a section from about 10 degrees to 100 degrees of arc on the rotatable disc. In some embodiments, the plurality of reaction chambers comprises from 1 to 100 reaction chambers. In some embodiments, each of the plurality of reaction chambers comprises a volume of from about 10 μL to about 100 μL. In some embodiments, each of the plurality of reaction chambers comprises a depth of from about 0.1 mm to about 1.0 mm. In some embodiments, the plurality of reaction chambers comprises a depth of at most about 0.25 mm. In some embodiments, the first temperature is maintained for a first period of time. the second temperature is maintained for a second period of time, and the third temperature is maintained for a third period of time. In some embodiments, the first temperature is selected from about 90 degrees C. to about 99 degrees C., the second temperature is selected from about 50 degrees C. to about 74 degrees C., and the third temperature is selected from about 65 degrees C. to about 75 degrees C. In some embodiments, the first period of time is selected from about 500 ms to about 2 s, the second period of time is selected from about 3 s to about 18 s and, the third period of time is selected from about 1 s to about 6 s. In some embodiments, the first heating element comprises a first radial length, and the second heating element comprises a second radial length, and the third heating element comprises a third radial length. In some embodiments, the second radial length is about 6 to about 9 times the first radial length and the third radial length is about 2 to about 3 times the radial length of the first radial length. In some embodiments, the method further comprises independently stabilizing the rotatable disc at the first temperature for the first period of time and the second temperature for the second period of time and the third temperature for the third period of time. In some embodiments, stabilizing comprises clamping the rotatable disc between a first heating block and a second heating block of the first heating element, the second heating element, or the third heating element. In some embodiments, the method further comprises subsequent to stabilizing the rotatable disc, unclamping the rotatable disc from the first, second, or third heating element. In some embodiments, wherein the excitation light is supplied by a plurality of optic heads. In some embodiments, the plurality of optic heads further comprises a plurality of filters to change the excitation light of a plurality of wavelengths. In some embodiments, the emission light is measured on a first detector. In some embodiments, the first detector comprises one or more fluorescence detectors to measure an emission intensity for the emission light of plurality of wavelengths. In some embodiments, the sealer is a heat sealer.

The present disclosure provides an analytical device for processing a target nucleic acid comprising a housing, wherein the housing comprises: a sample holder configured to hold and rotate a rotatable disc comprising a plurality of reaction chambers; a sealer configured to seal the reaction chamber while the rotatable disc is on the sample holder; a first heating element maintained at a first temperature configured to heat the rotatable disc to the first temperature; and a second heating element maintained at a second temperature configured to heat the rotatable disc to the second temperature.

In some embodiments, the analytical device further comprises a rotatable platform capable of spinning at a speed of at least 15000 RPM. In some embodiments, the analytical device comprises the rotatable disc held within the sample holder. In some embodiments, the sealer is a heat sealer. In some embodiments, the rotatable disc further comprises a loading chamber and a channel connecting the loading chamber to the plurality of reaction chambers. In some embodiments, the channel comprises a thermoplastic material that seals the channel when heated to a temperature of 110 to 300 degrees C. In some embodiments, the plurality of reaction chambers comprises a first PCR reaction mixture comprising a primer and a fluorescent probe. In some embodiments, the rotatable disc further comprises a mixing chamber, wherein the mixing chamber comprises a second PCR reaction mixture comprising a polymerase, and a plurality of nucleotides. In some embodiments, the plurality of reaction chambers comprises a volume of from about 10 μL to about 100 μL and a depth of from about 0.1 mm to about 1.0 mm. In some embodiments, each of the plurality of reaction chambers comprises a depth at most 0.25 mm. In some embodiments, the plurality of reaction chambers comprises from one to 100 reaction chambers. In some embodiments, the channel comprises a z dimension from about 1 μm to about 1 mm and a width from about 1 mm to about 5 mm. In some embodiments, an aspect ratio of each of the plurality of reaction chambers to the channel is at least 10 to 1. In some embodiments, each of the plurality of reaction chambers has an interior and an exterior. In some embodiments, each of the plurality of reaction chambers is compatible with transmitting an excitation light of a plurality of wavelengths from the exterior of the plurality of reaction chambers and the plurality of reaction chambers is compatible with transmitting an emitted light of a plurality of wavelengths from the interior of the plurality of reaction chambers. In some embodiments, the rotatable disc comprises a thermoformed film and a sealing film that come together to form the plurality of reaction chambers. In some embodiments, the thermoformed film forms a shape and a size for the plurality of reaction chambers. In some embodiments, the thermoformed film has a Tg higher than about 100 degrees C. In some embodiments, the sealing film and thermoformed film comprise a resin. In some embodiments, the resin comprises a single polymer. In some embodiments, the resin comprises an inner polymer and an outer polymer, and the inner polymer has a lower Tg than the outer polymer. In some embodiments, the single polymer, the inner polymer, and the outer polymer are each independently selected from polyolefin, polycarbonate, polystyrene, polymethyl methylacrylate, polyethylene, and polypropylene. In some embodiments, the resin for the sealing film and the resin for the thermoformed film is heat sealed together. In some embodiments, the resin for the sealing film and thermoformed films is the same. In some embodiments, the sealer is designed to heat seal the reaction chamber and thereby apply pressure and heat to the rotatable disc. In some embodiments, the first heating element comprises a first radial length and the second heating element has a second radial length and the second radial length is about 6 to about 9 times the radial length of the first radial length. In some embodiments, the analytical device further comprises a third heating element maintained at a third temperature configured to heat the rotatable disc to the third temperature. In some embodiments, the third radial length is about 2 to about 3 times the radial length of the first radial length. In some embodiments, the first heating element, the second heating element, and the third heating element, each independently comprise a pair of heating blocks designed to clamp the rotatable disc between them. In some embodiments, the analytical device further comprises a plurality of optic heads. In some embodiments, wherein the plurality of optic heads provides an excitation light source of one or more wavelengths. In some embodiments, the excitation light source wavelength is selected from 400 nm to 750 nm. In some embodiments, the optic head further comprises a plurality of filters to add one or more wavelengths to the excitation light source. In some embodiments, the analytical device further comprises a fluorescence detector to measure an emission intensity for one or more wavelengths. In some embodiments, the fluorescence detector can measure the emission intensity of more than one wavelength simultaneously. In some embodiments, the heat sealer comprises a first element configured to provide a thermal energy and a pressure on the rotatable disc and a second element configured to provide a counter force to the pressure.

Detailed Figure Descriptions

FIG. 1 illustrates a line drawing of a top view of a rotatable disc described herein. The rotatable disc (101) comprises a set of fluidic canals (102) that connects different chambers (e.g., cuvettes) comprising, for example, PCR reagents and a nucleic acid sample, to the reaction chambers or plurality of reaction chambers (103) via a channel (108). Additionally, provided herein, are elements of the analytical device for thermocycling. For example, these elements include a heating block for denaturation during PCR (104), a heating block for annealing primers to a target nucleic acid (105), and a heating block for elongation of the target nucleic acid sequence by a polymerase (106). The device further comprises an optic device or optic head (107) designed to excite one or more target fluorophores and detect the resulting fluorescence intensity.

FIG. 2 illustrates a top view of a rotatable disc described herein in the context of an analytical device described herein. The rotatable disc (201) is inserted onto an analytical device designed for processing nucleic acid samples, for example by RT-PCR. For example, but not by way of limitation, the sample (e.g., a liquid sample containing a target nucleic acid) is inserted into the inlet motif on the device (202). The sample then flows into a loading chamber (e.g., heating chamber) (203) for sample processing to extract the target nucleic acid. Following, a metering chamber laser valve (204) is activated to open a flow from the loading chamber (e.g., heating chamber) (203) to a metering chamber (205) with metering holes that controls the sample flow before mixing with a PCR reagent mixture (e.g., buffer, polymerase, and dNTPs). The metered volume of sample is then mixed with a PCR reagent mixture (e.g., buffer, polymerase, or dNTPs) in a mixing chamber (207). The sample mixed with the reconstituted reagents then flows from the mixing chamber on the disc body (210) through the channel (208) on the rotatable disc reaction chamber insert (e.g., cuvette insert) (211) to the plurality of reaction chambers (209). An additional PCR reagent mixture (e.g., primers and fluorophore) are stored in the plurality of reaction chambers and are mixed with the sample flows from the channel (208) into the reaction chambers (209). As shown herein, in one nonlimiting example, the reaction chamber insert and disc body are connected on the analytical device via a connection chamber (212).

Figure 3:
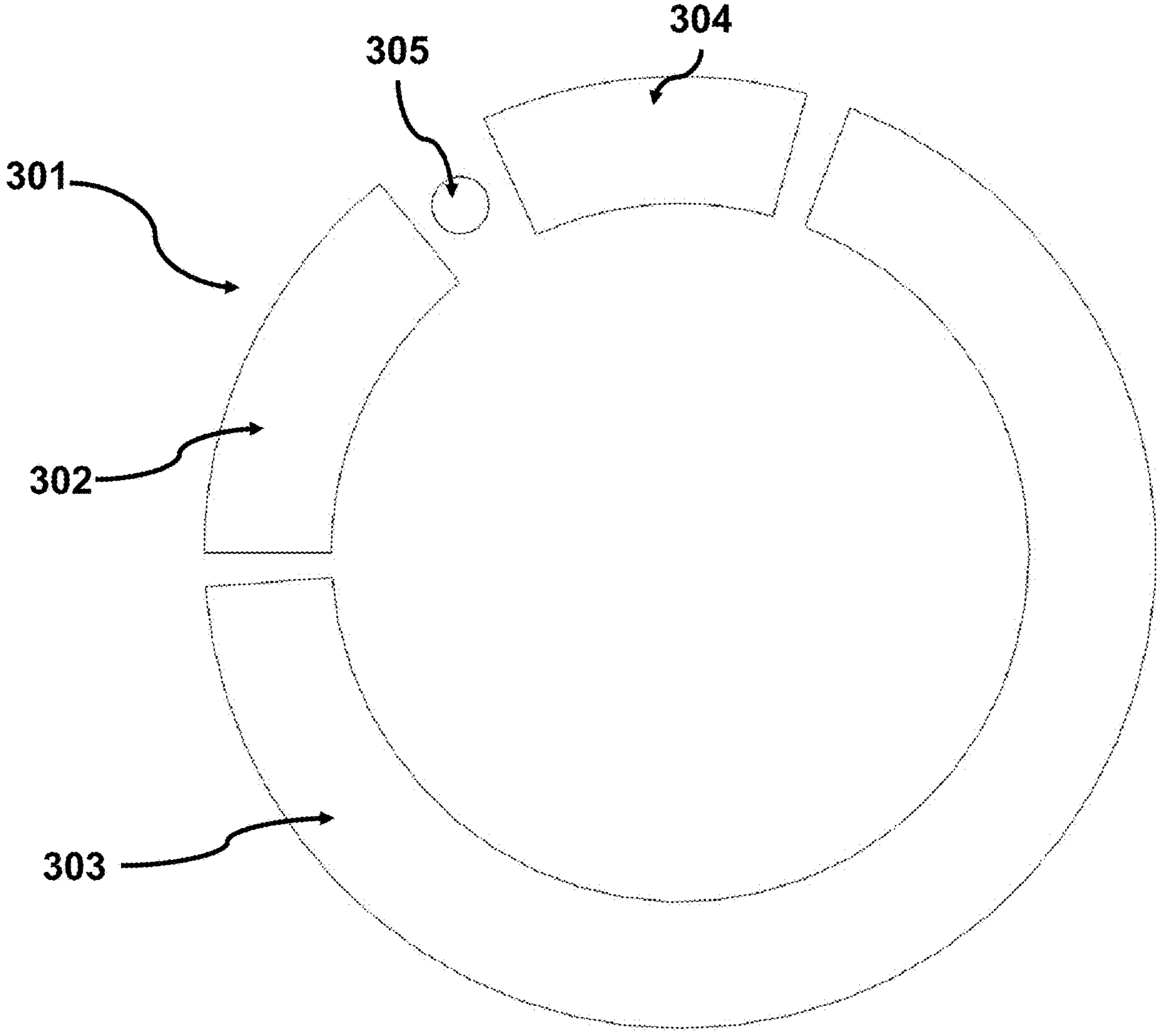
FIG. 3 illustrates a line drawing representative of the major elements required for thermocycling on an analytical device described herein.

FIG. 3 illustrates a line drawing representative of the major elements required for thermocycling on an analytical device described herein. For example, these elements of the analytical device (301) include a heating block for denaturation during PCR (304), a heating block for annealing primers to a target nucleic acid (302), and a heating block for elongation of the target nucleic acid sequence by a polymerase (303). The device further comprises an optic device or optic head (305) designed to excite one or more target fluorophores and detect the resulting fluorescence intensity.

Figure 4:
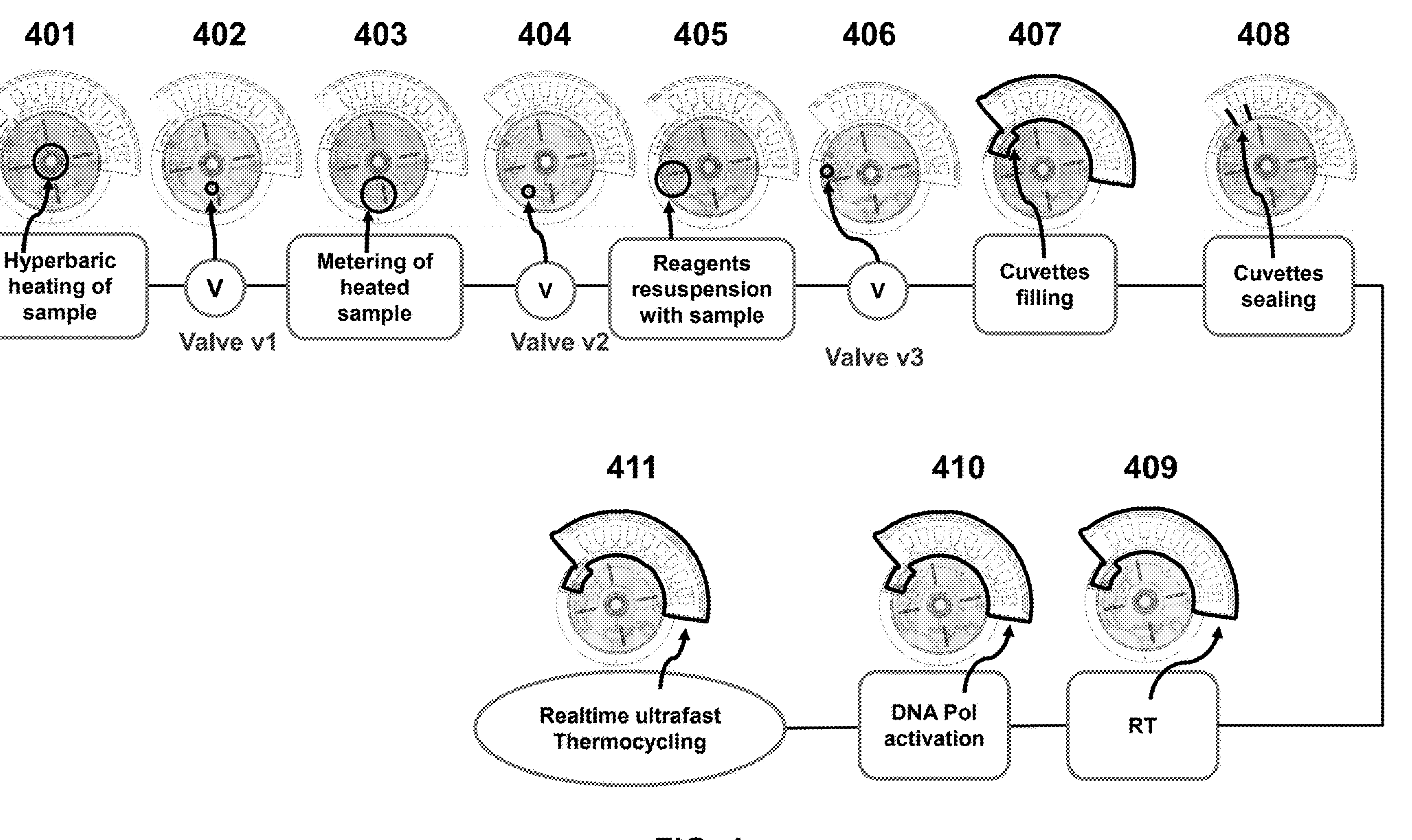
FIG. 4 illustrates a top view of a rotatable disc described herein during the steps of a method for RT-PCR described herein.

FIG. 4 illustrates a top view of a rotatable disc described herein during the steps of a method for RT-PCR described herein. The sample inside the loading chamber is heated at a temperature above 100° C., for a period of 15 seconds (FIG. 4, 401). After heating completion, valve (V1, FIG. 4 402), for example, comprised of a PMMA membrane, is pierced using an electromagnetic means (e.g., LASER). Piercing of V1 flows liquid from inside the loading chamber (FIG. 2 202) to the metering chamber (FIG. 2 205) via a canal. The sample is transferred into metering chamber via centrifugation at a speed comprise between 3000 to 6000 RPM. The metering chamber is designed to meter different volumes depending on the multiplexing number targeted. Metering holes (FIG. 2 206) are pierced before or during instrument use to meter the exact volume require for the assay (FIG. 4 403). For example, but not by way of limitation, if the assay requires only one reaction chamber, metering hole 1 will be pierced. If the assay required 3 reaction chambers, metering hole 3 will be pierced. During metering, the extra volume of sample will flow to an overflow chamber (FIG. 2 213). The metered volume is then sent toward the mixing chamber after opening laser valve V2 (FIG. 4 404). Inside reagent mixing chamber, RT-PCR reagent are stored, for example in a lyophilized form. RT-PCR reagents are mixed with metered sample by Euler forces (FIG. 4 405). After opening laser valve V3 (FIG. 4 406), resuspended RT_PCR reagent mixed with sample are sent to the reaction chamber insert, for example at 1000 to 3000 RPM, for filling the reaction chambers (FIG. 4 407). After filling, reaction chambers are sealed from each other, for example, via a heat sealer mounted inside the instrument. In some examples, the heat sealer compresses the channel (FIG. 4 408). In some embodiments, the heat seal is performed using a temperature comprised between 200 to 300° C. For example, after sealing the RT step is performed by pressing the rotatable disc between the annealing block at 65° C. for 15 to 60 sec (FIG. 4 409). A short (e.g., 5 to 30 sec) activation step of the hot start polymerase is achieved by rotatable disc insert between the 95° C. block (FIG. 4 410). After DNA pol activation, the thermocycling begins (FIG. 4 411).

Figure 5C:
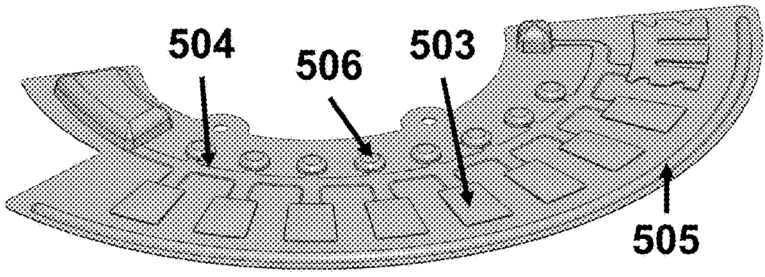

FIG. 5 illustrates multiple views of a rotatable disc described herein. FIG. 5A illustrates two components used to manufacture some embodiments of a rotatable disc described herein. For example, the rotatable disc is manufactured by a thermoforming film (501) (e.g., with a thickness from about 140 um to about 300 um). The thermoforming film is thermoformed to define the size and shape of the plurality of reaction chambers (503) and the channel (504). The thermoformed film (501) is sealed to a thin plastic sealing film (502) (e.g., with a thickness from about 50 um to about 150 um). The rotatable disc further comprises a reinforcement bar (505) on the rotatable disc to support the stability of the rotatable disc due to the design and manufacturing of the disc by two films. FIG. 5B illustrates a close-up example of a reaction chamber comprised on a rotatable disc described herein. In some examples, as shown herein, the reaction chambers (503), comprise a slight dome shape created by the thermoformed film (501) and sealing film (502). Additional elements portrayed, for example, are a reinforcement bar (505) to support the stability of the rotatable disc, and the channel (504) that carries the sample to the reaction chamber or plurality of reaction chambers (503). FIG. 5C illustrates an additional view of a manufactured rotatable disc comprising a plurality of reaction chambers designed for RT-PCR. In some examples, as shown herein, the rotatable disc comprises a plurality of reaction chambers (e.g., cuvettes) (503), a channel (504), and a reinforcement bar (505), and the rotatable disc further comprises additional domes (506) comprising a z dimension found on the other side of the channel (504) from each reaction chamber (e.g., cuvette) (503).

FIG. 6 illustrates the components used to manufacture some embodiments of a rotatable disc described herein. The elements provided herein are one example of the reaction chamber insert for the rotatable disc and comprises a thermoforming film (601), sealing film (602), a plurality of reaction chambers (603), a channel (604), reinforcement (605) for stability of the thermoformed films, an inlet for the rotatable disc insert (606), and a coextruded material (607) or skeleton for manufacturing the disc with the thermoforming film and sealing film.

FIG. 7 illustrates a line drawing overview of an analytical device for processing a target nucleic acid. For example, the rotatable disc (701) is inserted into the analytical device for processing nucleic acid samples (e.g., RT-PCR). An example of the analytical device shown herein comprises a first heating block set at a denaturing temperature (704) and a second heating block set at a temperature compatible with both annealing and elongation during PCR (705). The device in this example further comprises two optic heads (706) designed to excite a plurality of target fluorophores and detect their fluorescence emission intensity. Finally, the analytical device in this example comprises a heat sealer (703) designed to seal across the channel of the rotatable disc to seal off the plurality of reaction chambers from one another.

Figure 8A:
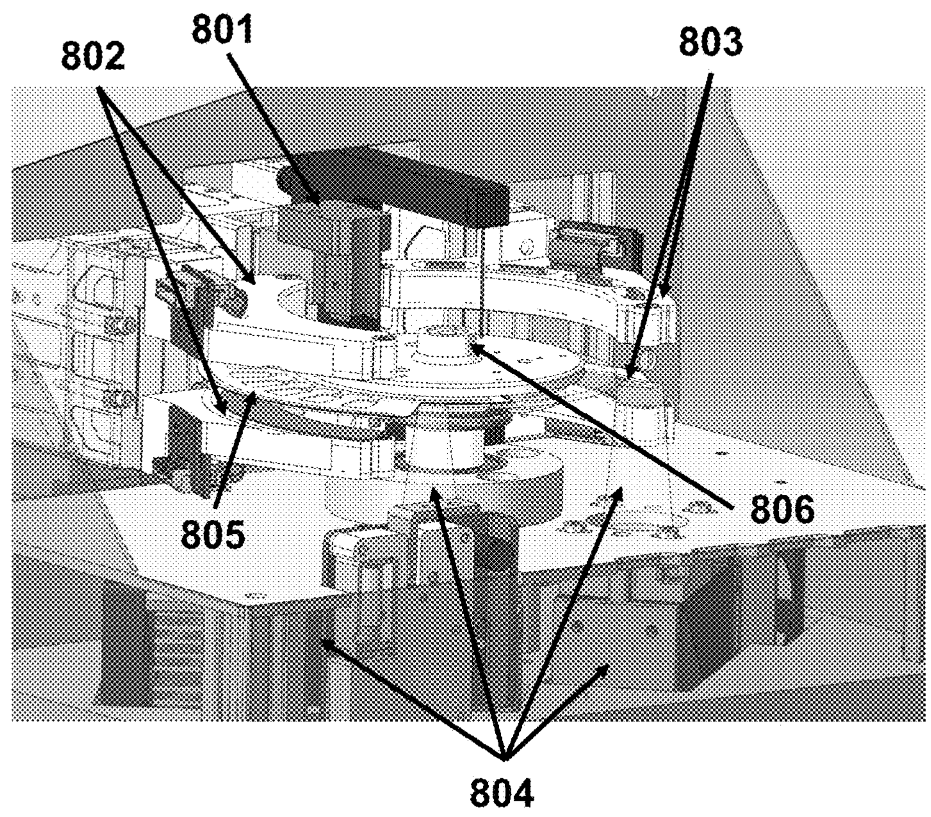
FIGS. 8A-8B illustrate a cartoon schematic of an analytical device for processing a target nucleic acid.
Figure 8B:
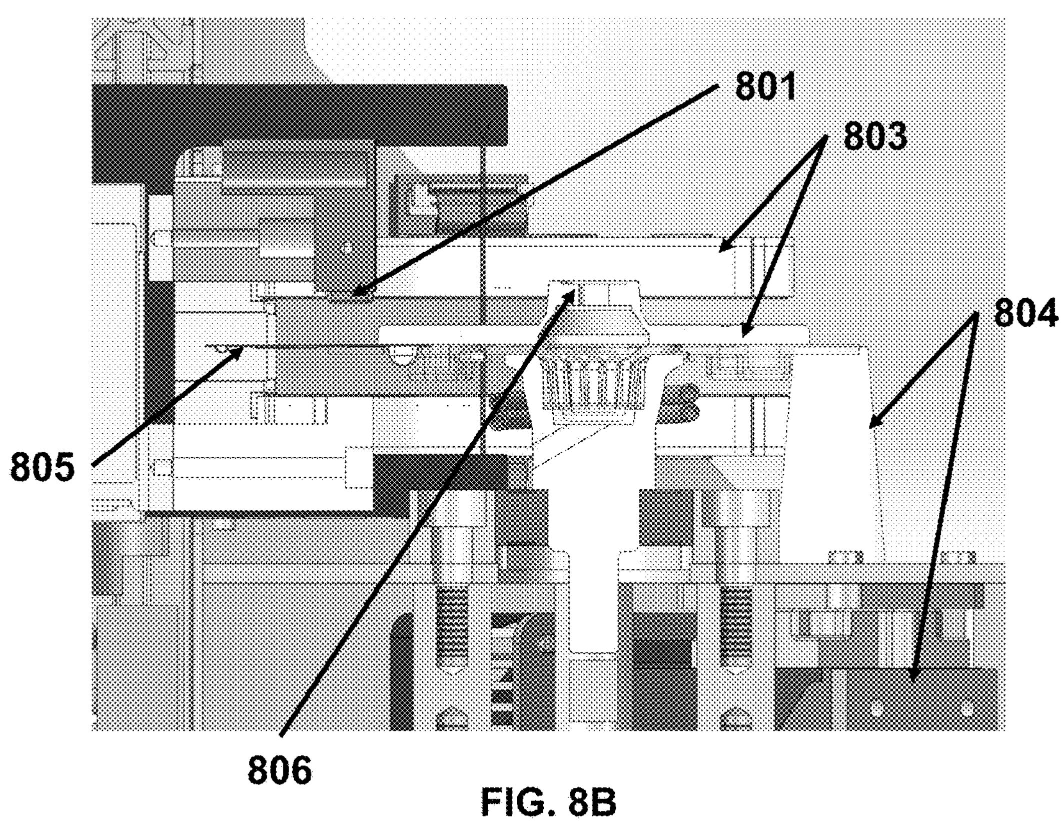

FIG. 8 illustrates a cartoon schematic of an analytical device for processing a target nucleic acid. FIG. 8A illustrates a front view of the analytical device. comprises a first heating block set at a denaturing temperature (802) and a second heating block set at a temperature compatible with both annealing and elongation during PCR (803). These heating blocks are shown to sandwich the rotatable disc (805) that ultimately contains the sample to be processed after sample injection through the inlet and loading chamber on the device (806) The device in this example further comprises two optic heads (804) designed to excite a plurality of target fluorophores and detect their fluorescence emission intensity. Finally, the analytical device in this example comprises a heat sealer (801) designed to seal across the channel of the rotatable disc to seal off the plurality of reaction chambers from one another. In one example, the analytical device shown herein FIG. 8B illustrates a side view of the analytical device. The elements shown in this view of the analytical device comprise the heat sealer (801), the second heating block (803), an optical device (804), the rotatable disc (805), and the inlet/loading chamber (806) for sample insertion.

FIG. 9 illustrates a cartoon schematic of an analytical device for processing a target nucleic acid showing a heat sealer element for sealing a channel on a rotatable disc. FIG. 9A illustrates an overview of the heat sealer housed within an analytical above the channel on the rotatable disc. FIG. 9B illustrators a close view of the heat sealer housed within an analytical above the channel on the rotatable disc. FIG. 9C illustrates an overview of the heat sealer housed within an analytical device contact with the channel on the rotatable disc. FIG. 9D illustrators a close view of the heat sealer housed within an analytical device contact with the channel on the rotatable disc. In one example of the rotatable disc and analytical device, the elements shown herein by FIG. 9A-D include a heat sealer (901), two heating blocks for thermocycling (902), a rotatable disc (903) comprising a plurality of reaction chambers (904) and a channel (905), and a loading chamber/inlet (906) for sample insertion into the device. Comparison of FIG. 9A/B to FIG. 9C/D, respectively, illustrate an example of the method of using a device for processing nucleic acid samples that comprises contacting the heat sealer (901) with the rotatable disc (903) over the entire width of the channel (905) connecting the plurality of reaction chambers (904), thereby heat sealing the channel and reaction chambers from one another and from the rest of the disc.

FIG. 10 illustrates a front-view cartoon schematic of an analytical device wherein the disclosed heating block elements clamp and unclamp the disclosed rotatable disc. A comparison of FIG. 10A to FIG. 10B illustrates the first pair of heating blocks clamping, or coming into contact with, the rotatable disc. In one example of a method performed on the analytical device, the first heating block (1002) (e.g., set at a temperature compatible with the denaturing step in PCR) clamps down on the rotatable disc (1005) as shown by comparing element 1002 in FIGS. 10A and 10B, thereby allowing heat transfer to the reaction chambers comprising the sample for PCR amplification. A comparison of FIG. 10B to FIG. 10C shows the heating block unclamping from the rotatable disc and the rotatable disc rotating to the second pair of heating blocks. In a further example of the method performed on the analytical device, the first heating block (1002) unclamps from the rotatable disc (1005), and the rotatable disc rotates to the side of the analytical device comprising the second heating block (1003) (e.g., set at a temperature compatible with the annealing/elongation steps in PCR). This process is shown by a comparison of elements 1002 and 1005 in FIGS. 10B and 10C. A comparison of FIG. 10C to FIG. 10D illustrates the second pair of heating blocks clamping, or coming into contact with, the rotatable disc. In a further example of a method performed on the analytical device, the second heating block (1003) (e.g., set at a temperature compatible with the annealing/elongation steps in PCR) clamps down on the rotatable disc (1005) as shown by comparing element 1003 in FIGS. 10C and 10D, thereby allowing heat transfer to the reaction chambers comprising the sample for PCR amplification.

Figure 12A:
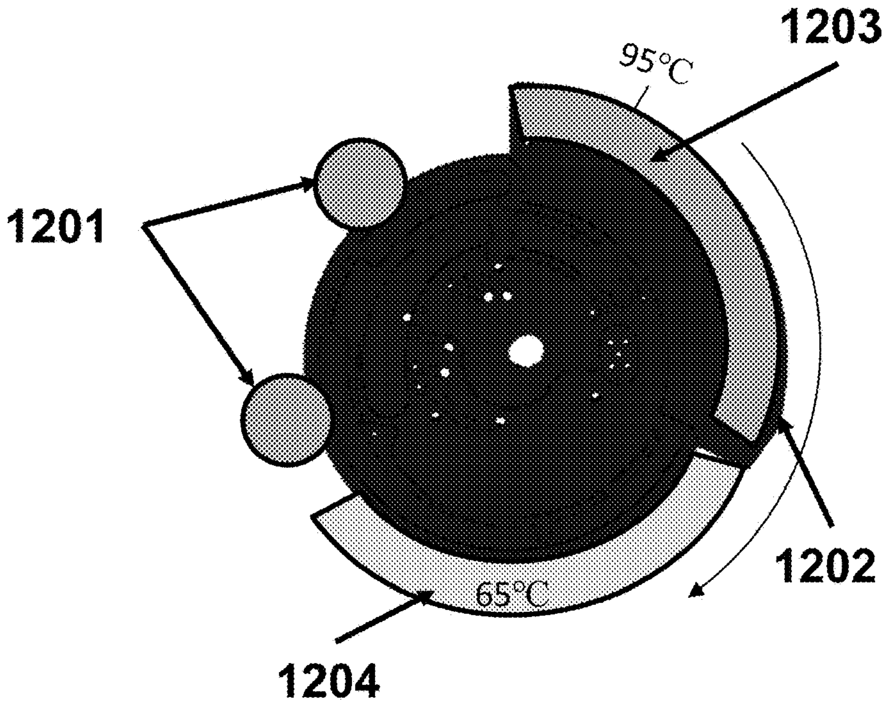
FIG. 12A-12B illustrate cartoon illustrations of the rotatable disc rotating from one heating block (FIG. 12A) to a second heating block (FIG. 12B).
Figure 12B:
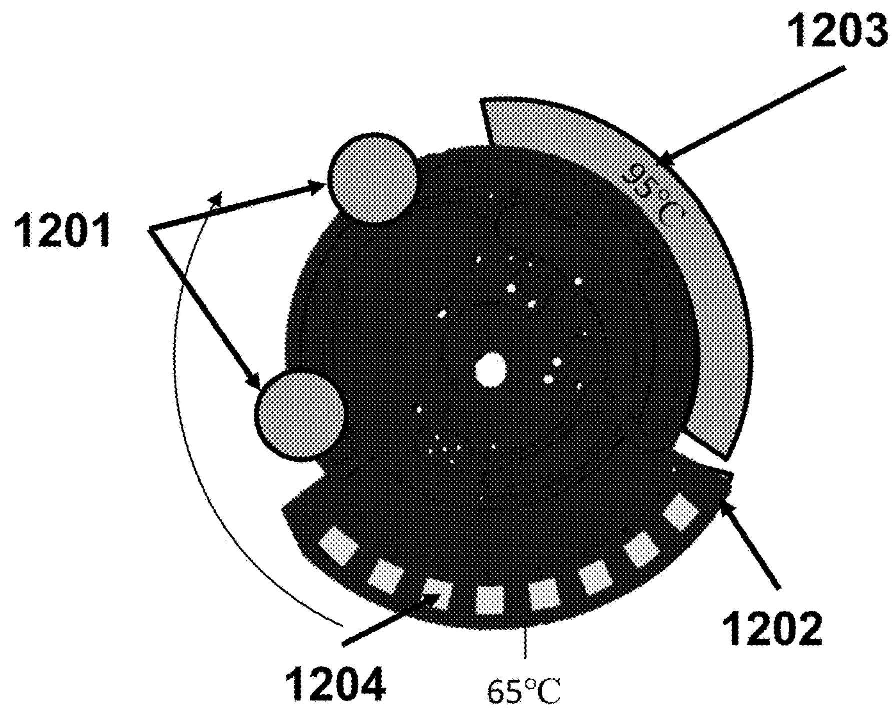

FIG. 12 illustrates a cartoon illustration of the rotatable disc rotating from one heating block (FIG. 12A) to a second heating block (FIG. 12B). For example, the rotatable disc (1202) is rotated from a first heating block (1203) (e.g., set at a denaturation temperature of about 95 degrees Celsius) to a second heating block (1204) (e.g., set at an annealing/elongation temperature of 65 degrees Celsius). Additional elements shown in this example include two optic devices or two optic heads (1201) for exciting and measuring the emission for a plurality of target fluorophores.

Figure 13A:
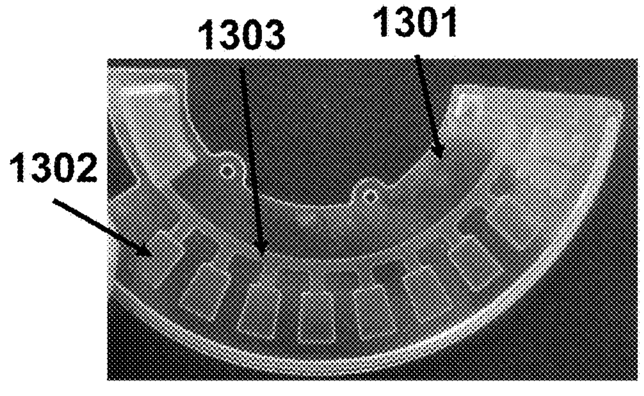
FIGS. 13A-13C provide photographs of examples of the disclosed rotatable disc and disclosed analytical device.
Figure 13B:
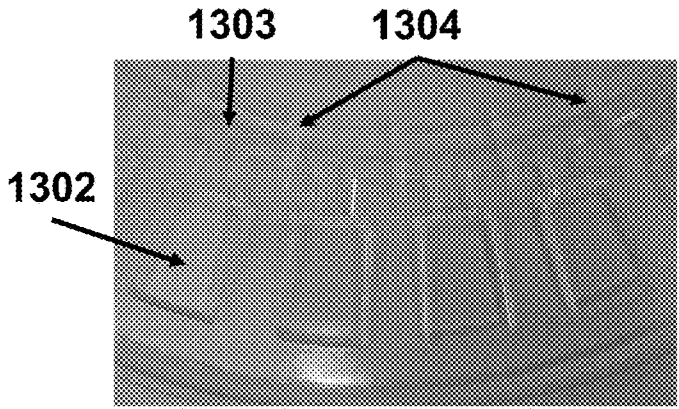
Figure 13C:
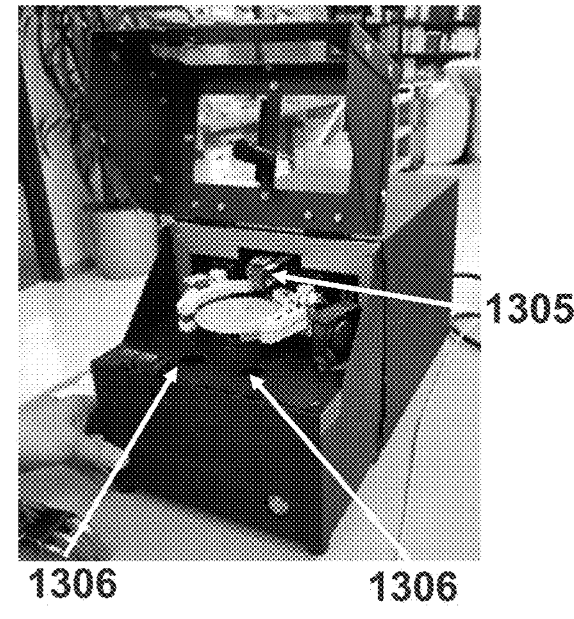

FIG. 13 provides photographs of examples of the disclosed rotatable disc and disclosed analytical device. FIG. 13A shows an example of a manufactured rotatable disc. FIG. 13B shows an example of a close-up view of the sealed channels on the rotatable disc. FIG. 13C shows an example of the analytical device used for processing a target nucleic acid (e.g., RT-PCR). The elements shown in FIG. 13A/B include a rotatable disc (1301) comprising a plurality of reaction chambers (1302) connected to a channel (1303) wherein the channel (1303) can be sealed (1304) by a heat sealer. FIG. 13D shows elements of the analytical device comprises the heat sealer (1305) used to seal the channel in FIG. 13B and two optic heads (1306).

Figure 14A:
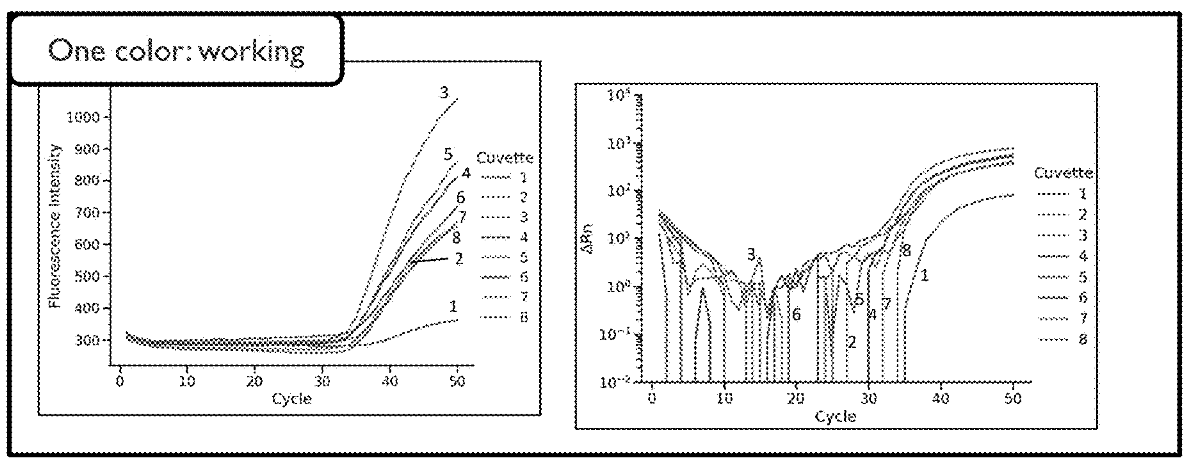
FIGS. 14A-14B illustrate data showing fluorescence readout of the device provided herein.
Figure 14B:
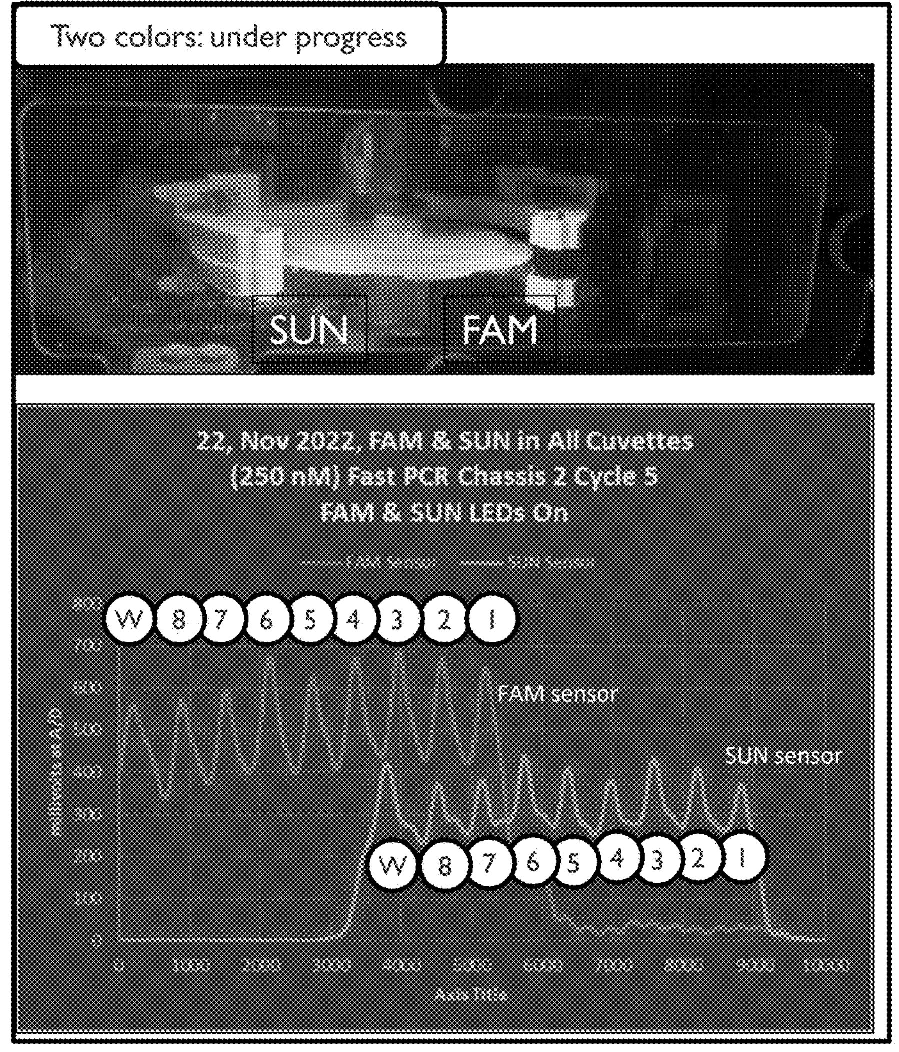
Figure 15A:
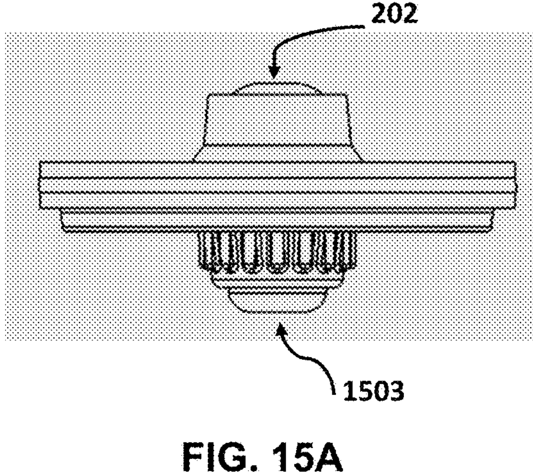
FIGS. 15A-15C illustrate multiple views of a hyperbaric heating vessel.
Figure 15B:
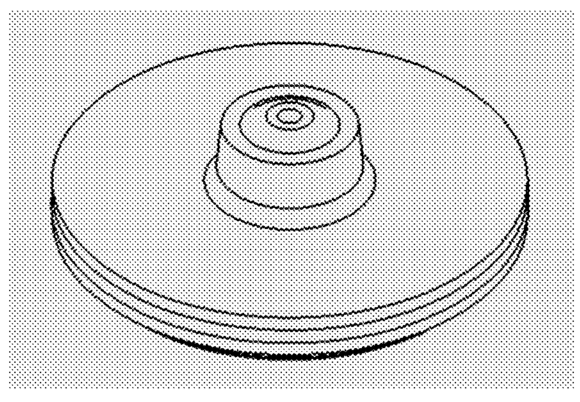
Figure 15C:
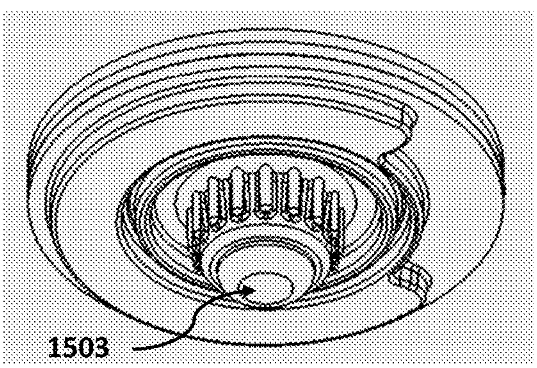

FIGS. 14A and 14B illustrate data showing fluorescence readout of the device provided herein. FIG. 14A illustrates signal detection by one color channel implemented within the device. FIG. 14B illustrates signal detection by two color channels implemented within the device.

Figure 29:
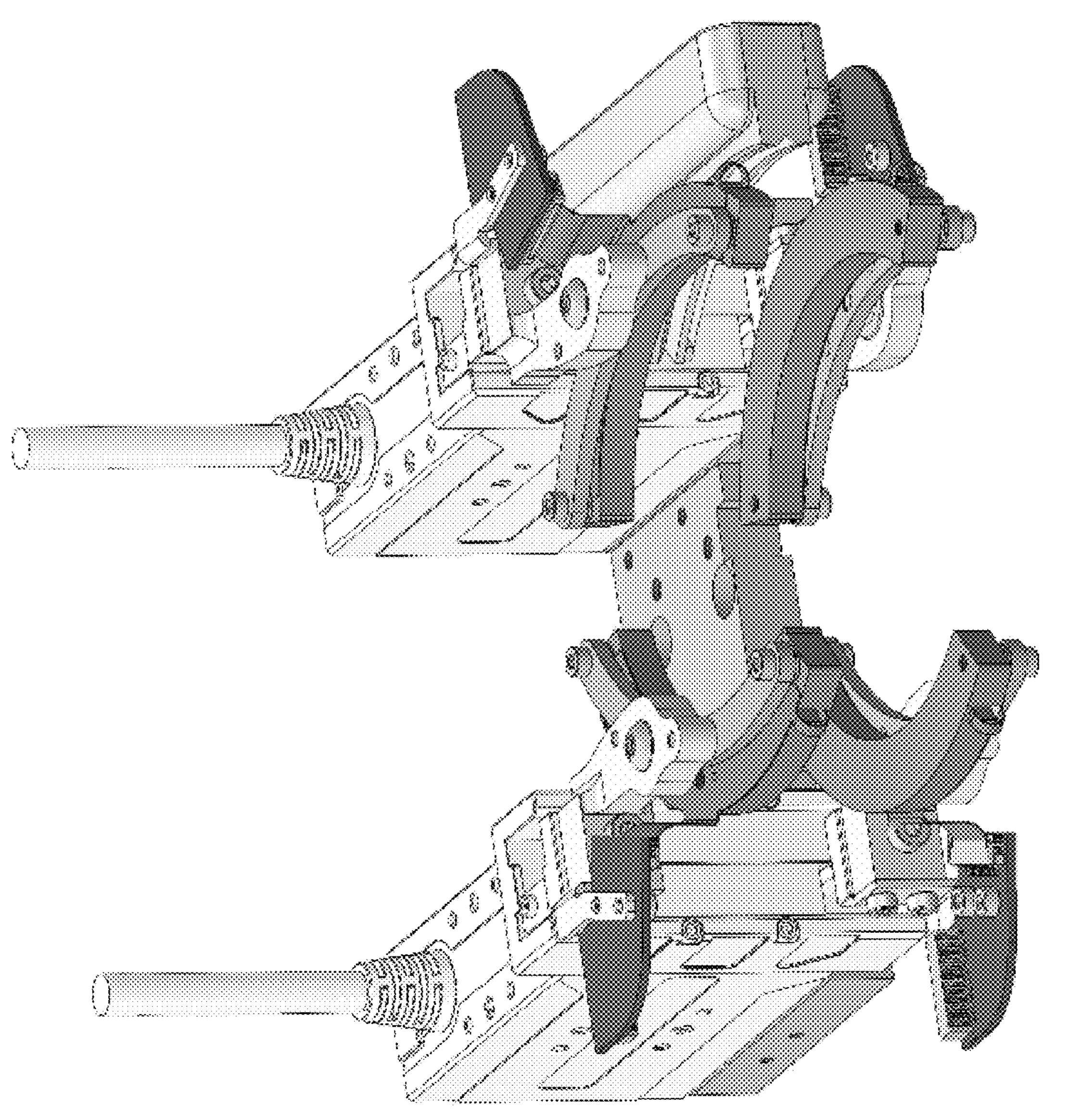
FIG. 29 shows a diagram of an embodiment with two heating blocks.

FIG. 29 shows a diagram of the structure of an embodiment with one block pair set at about 95 C and the other pair at about 65 C (annealing/elongation temperature). With two blocks, the cooling step is the longest step, taking about 7 seconds.

Figure 30:
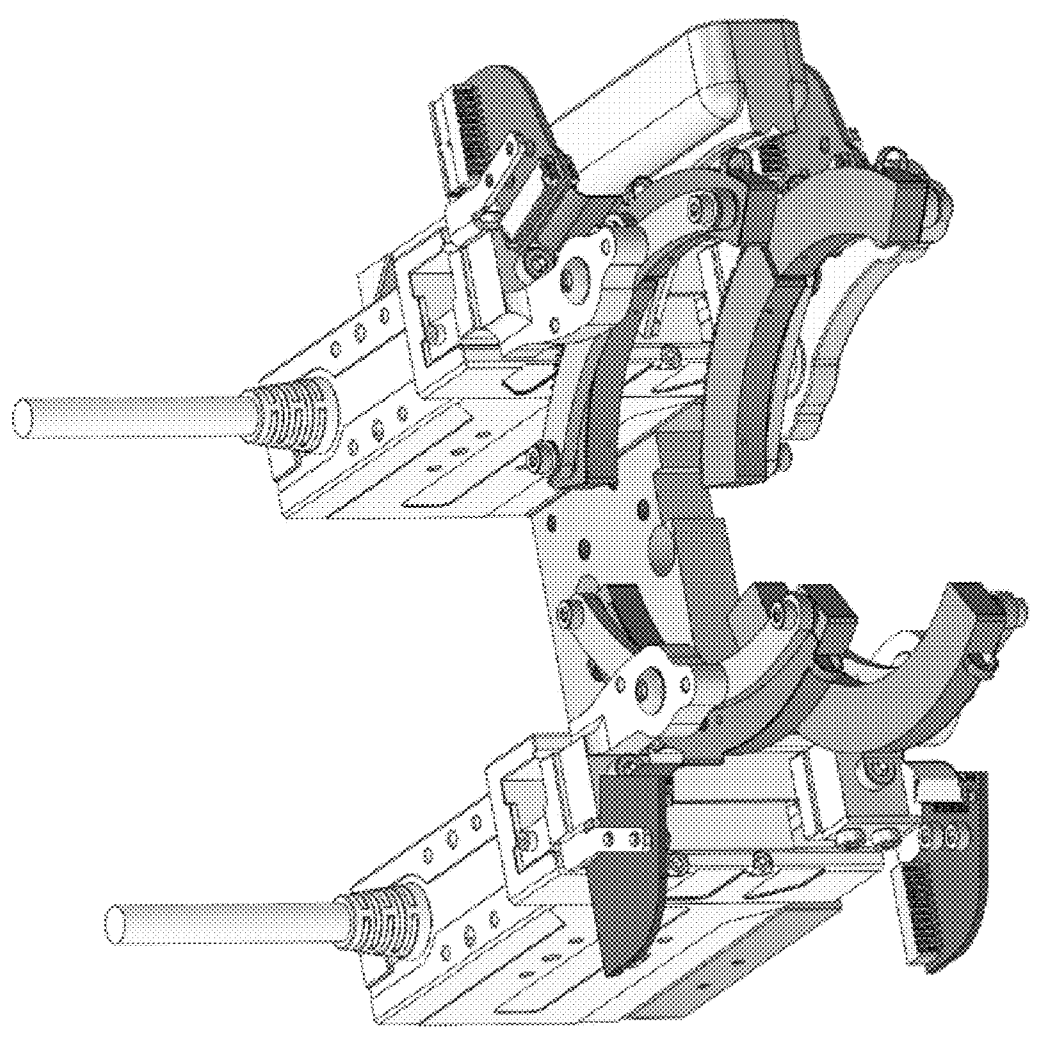
FIG. 30 shows a diagram of the structure of an embodiment with three blocks instead of two.

FIG. 30 shows a diagram of the structure of an embodiment with three blocks instead of two. In this embodiment, the annealing pair of blocks is divided into two distinct temperature zones that can be set at two different temperatures independently from each other. In the case of an assay that requires 4 cuvettes or less, the two distinct blocks may be set at two different temperatures, where the half block closer to the 95 C block is used as a heat sink and set at a temperature well below the annealing temperature. For example, the half block closer to the 95 C block may be set at 40 C. The second half block may be set at the annealing/elongation temperature (e.g. 65 C).

The disc rotates from the 95 C block and is first clamped by the heat sink half block to cool the PCR insert as fast as possible. This allows the disc to cool more quickly than if moved straight to the annealing temperature block. After the disc comes to annealing temperature, the disc is moved on to the annealing temperature half block. The time the disc takes to come from 95 C to annealing temperature when in contact with the heat sink half block can be calculated.

Figure 31:
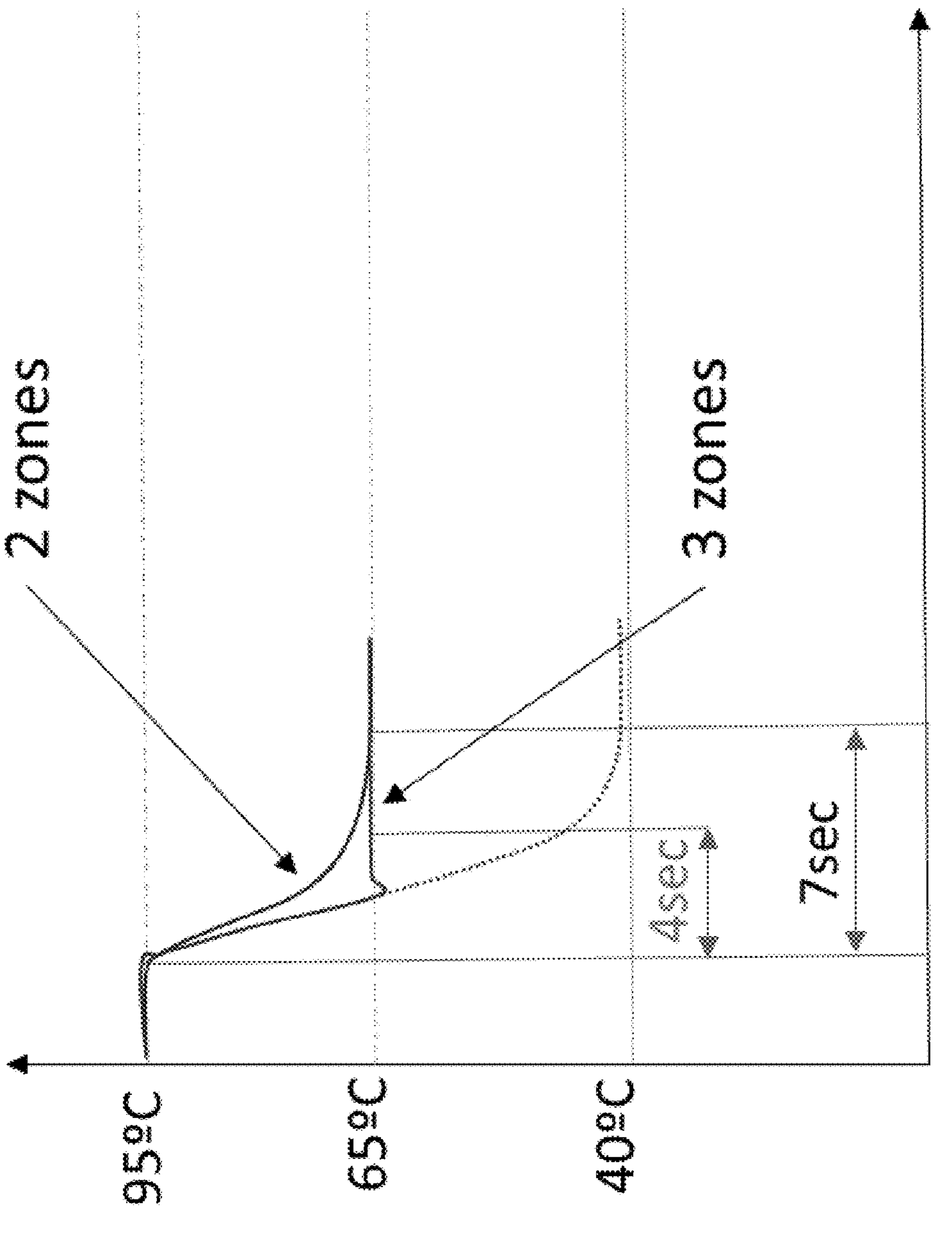
FIG. 31 shows a graph demonstrating that the cooling rate of the PCR disc is accelerated using the heat sink block.

FIG. 31 demonstrates that the cooling rate of the PCR disc is accelerated using the heat sink block. Without the heat sink block, the disc will more slowly approach the annealing temperature in an asymptotic manner when the disc temperature is close to the annealing temperature. This extends the time taken to get to the annealing temperature. In this example, using the heat sink half block shortens the time taken compared to the two block embodiment from 7 seconds to 4 seconds.

To implement the three-block embodiment, the half block that acts as a heat sink needs to evacuate heat very quickly in order to stay at the same temperature after multiple cycles. To be efficient, the half block acting as the heat sink needs to come back to its target temperature in less time than the dwelling time required at the annealing/elongation temperature plus the time under the denaturation block plus the time it takes to move the insert to complete a cycle, or around a time comprising about 3 seconds to about 6 seconds. The block must therefore be able to cool very quickly.

Figure 32:
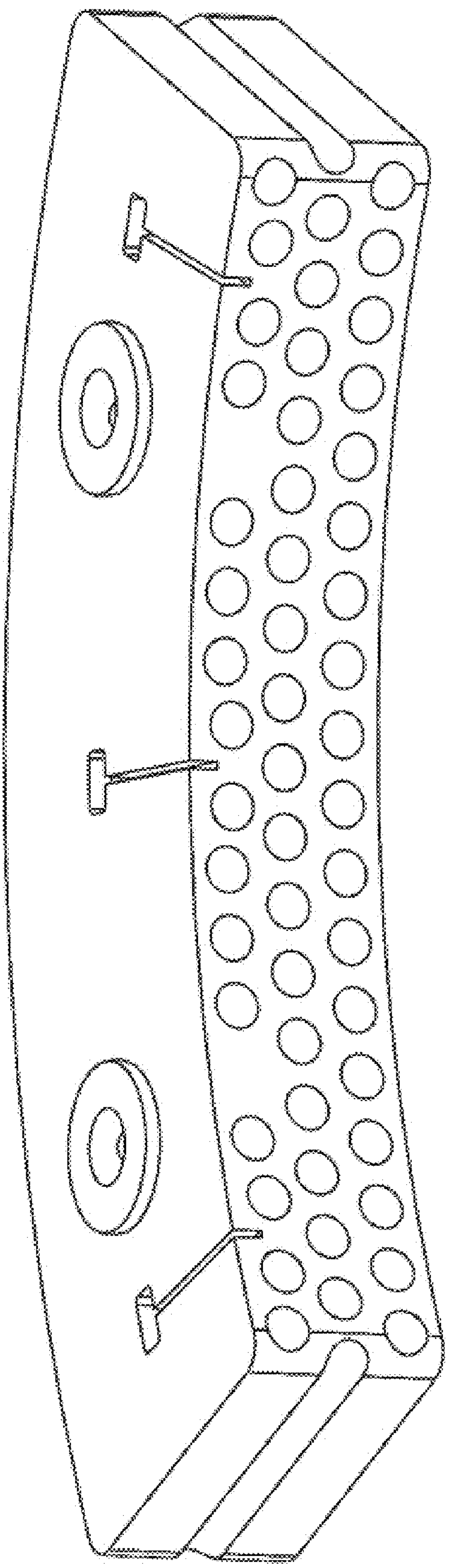
FIG. 32 shows an embodiment in which holes are pierced in the heating block to allow it to cool more rapidly.

Regular heating blocks frequently cool too slowly to come to temperature in this time range. FIG. 32 shows an embodiment in which holes are pierced in the heating block to allow it to cool more rapidly (e.g. Swiss cheese configuration).

Figure 33:
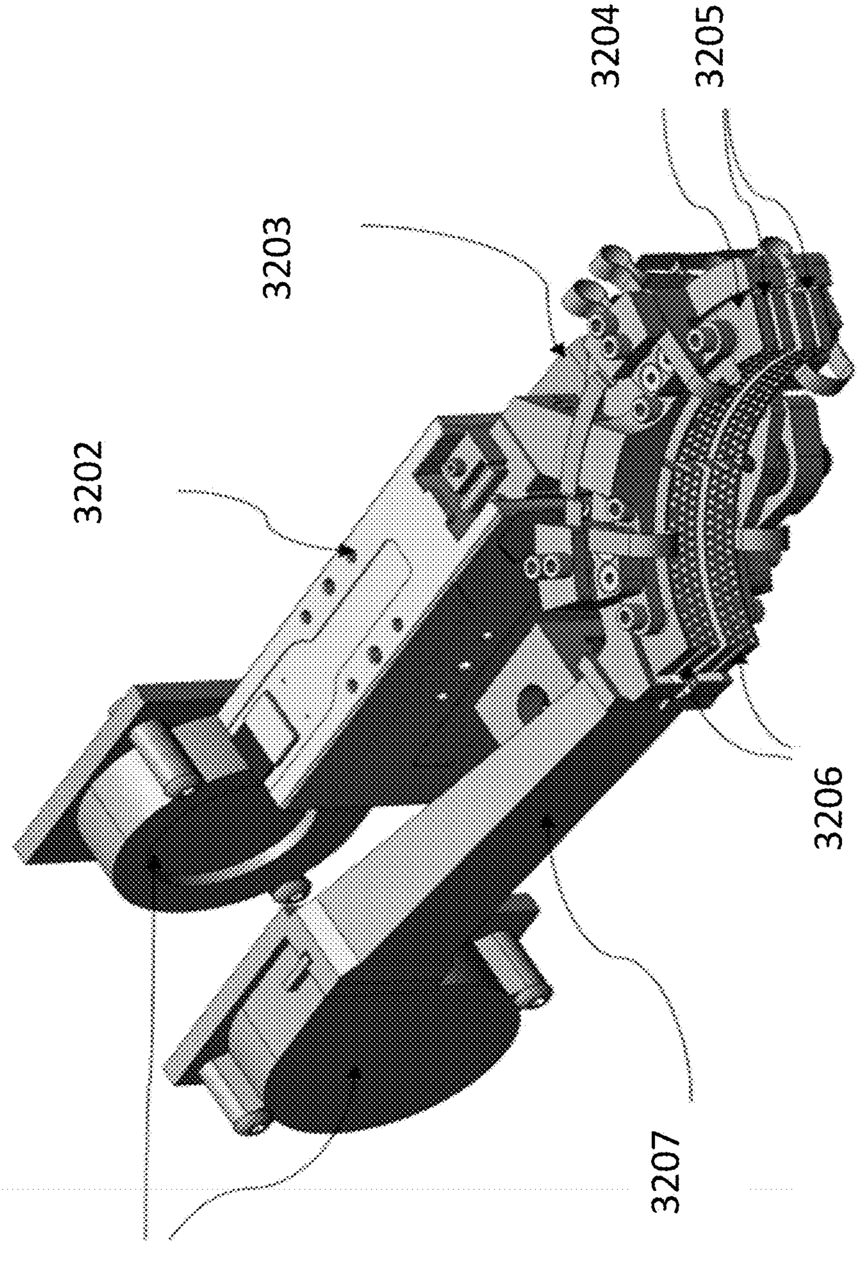
FIG. 33 shows how air flow can be directed via an air duct in one embodiment.

FIG. 33 shows how air flow can be directed via an air duct in one embodiment. In this embodiment, two fans, connected to air at room temperature outside the box, blow air via two air ducts both directed to their respective half blocks. 3201 shows a fan in this embodiment. 3202 shows a gripper. 3203 shows an air duct annealing half block. 3204 shows a flex heater. 3205 shows an annealing half block. 3206 shows a heat sink half block. 3207 shows an air duct heat sink half block.

Figure 34:
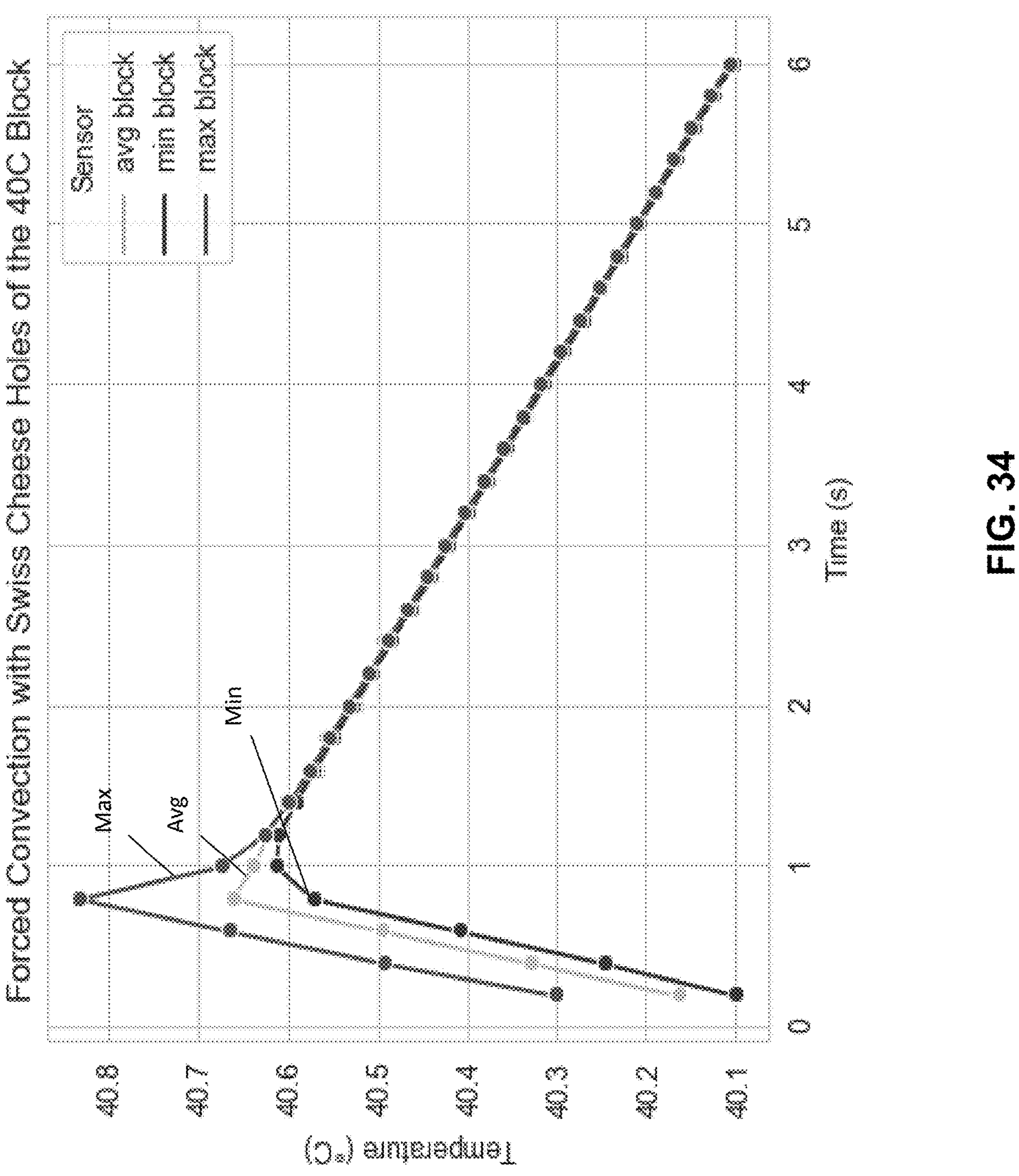
FIG. 34 displays a graph of simulations that demonstrate that the air duct instrument shown in FIG. 33 allows a Swiss cheese half heating block to come back to temperature in 5 seconds when set at 40° C. and when room temperature is 30° C.

FIG. 34 displays a graph of simulations that demonstrate that the air duct instrument shown in FIG. 33 allows a Swiss cheese half heating block to come back to temperature in about 5 seconds when set at about 40° C. and when room temperature is about 30° C. When tested, the system showed that the cooling ramp rate is at least 2.5 times faster than in simulations. This shows that the heat sink half block could potentially come back to temperature in about 2 seconds.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following examples are included for illustrative purposes only and are not intended to limit the scope of the invention.

Example 1: Ultra-Fast Polymerase Chain Reaction with Human Genomic DNA

In this example, ultra-fast PCR reactions amplifying human genomic DNA were run on a PCR device comprising a rotatable disc and heating blocks at 98° C. and 65° C. as described herein. In this example, 45 cycles of PCR were conducted in 7 minutes. PCR products after 45 cycles of ultra-fast PCR were subsequently analyzed via gel electrophoresis.

A target nucleic acid sample was first prepared using 620 copies of HeLa Genomic DNA in Tris-EDTA buffer. A custom assay targeting a 158 base pair region of the HPV-18 gene was used to detect the HeLa DNA in the sample. Two ultra-fast PCR reagent kits, Promega 2× GoTaq Rapid Master Mix and KAPA3G, were tested. The PCR reagents, comprising buffer/salts, polymerase, nucleotides, reverse transcriptase, primers, probes, and the target nucleic acid sample were combined in appropriate ratios to the desired PCR reaction volume. For the readout; a final concentration of 250 nM TaqMan Probe was used. The full PCR reaction was loaded into a custom PCR reaction vessel. Each reaction chamber was filled completely and segregated into independent reactions. For thermocycling, a heating apparatus comprising gripper heating blocks at annealing (65° C.) and denaturation temperatures (98° C.) was used to transfer heat to the PCR reaction vessel. During thermocycling, the reaction vessel was moved between the heating blocks via a motor. The following thermocycling conditions were used: 60 seconds of polymerase activation (98° C.), followed by 45 cycles of 2 seconds of denaturation (98° C.), and 7 seconds of annealing/extension (65° C.). The shunting between different blocks was repeated for 45 cycles.

Figure 21:
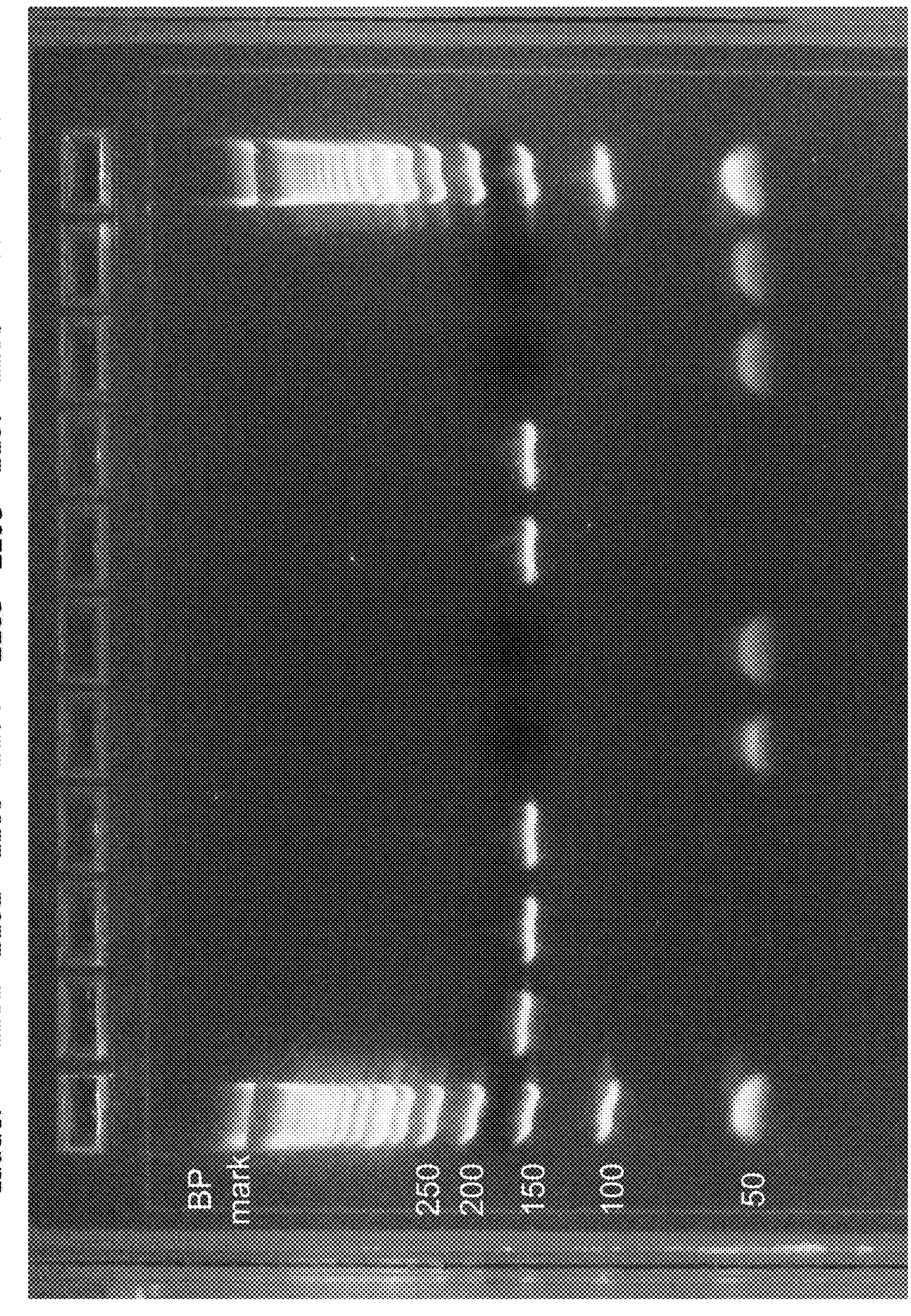
FIG. 21 provides a gel image showing the PCR products from PCR reactions with HeLa genomic DNA samples carried out on an analytical device provided herein.

The post PCR samples were analyzed via endpoint gel electrophoresis. Post PCR samples were extracted with a syringe, and each replicate of PCR product along with a 50 base pair PCR ladder were loaded into individual electrophoresis lanes on a 1% agarose gel. A voltage of 120 V was applied for 15 minutes on the gel, and the gel was imaged using a transilluminator to view the PCR product DNA. No template controls were tested to ensure no off-target amplification. FIG. 21 shows the imaged gel. Lane 2101 shows the PCR reaction with HeLa Genomic DNA sample and the Promega kit. Lanes 2102, 2103, 2106, and 2107 show PCR reactions with HeLa Genomic DNA sample and the KAPA3G kit. Lanes 2104, 2105, 2108, and 2109 show PCR reactions with a no template control and the KAPA3G kit. The gel showed the correct PCR product size for the targeted 158 base pair region of the HPV-18 gene for both ultra-fast PCR reagent kits tested. No off-target amplification was observed.

Example 2: Ultra-Fast Polymerase Chain Reaction with Respiratory Infectious Pathogens In this example, ultra-fast PCR reactions amplifying respiratory infectious pathogens Flu B and RSV were run on a PCR device comprising a rotatable disc and heating blocks at 55° C., 98° C., and 65° C. as described herein. In this example, 50 cycles of ultra-fast PCR were run, and real-time optical data were collected at the end of each PCR cycle.

A target nucleic acid sample was first prepared using a co-infected sample of Influenza B and Respiratory Syncytial Virus, both at 5000 copies/mL, in 1× Tris EDTA Buffer with 2 mg/mL Bovine Serum Albumin and 0.02% Sodium Azide. The sample was heated according to the hyperbaric PCR sample preparation method and then loaded with PCR reagents in a custom reaction vessel. A duplex Taqman probe assay was utilized, targeting a 94 base pair region of the Matrix gene in Flu B (FAM Taqman probe) and an 83 base pair region of the Matrix gene in RSV (TEX615 Taqman probe). PCR reagents comprising buffer/salts, polymerase, nucleotides, reverse transcriptase, primers, and probes were prepared at a 5× concentrate to be diluted 0.2× when combined with the target nucleic acid sample to produce the final PCR reaction mixture. The PCR reagents and the target nucleic acid sample were combined in appropriate ratio to the desired PCR reaction volume. The full PCR reaction was loaded into a custom PCR reaction vessel. Each reaction chamber was filled completely and segregated into independent reactions. For thermocycling, a heating apparatus comprising gripper heating blocks at reverse transcription (55° C.), annealing (65° C.), and denaturation temperatures (98° C.) was used to transfer heat to the PCR reaction vessel. During thermocycling, the reaction vessel was moved between the temperature blocks via a motor. PCR was run in the custom reaction vessel with the following cycling conditions: 60 seconds of reverse transcription (55° C.), 30 seconds of polymerase activation (98° C.), followed by 50 cycles of 2 seconds of denaturation (98° C.), and 7 seconds of annealing/extension (65° C.). The shunting between different blocks was repeated for 50 cycles, and real-time optical data were collected at the end of each PCR cycle.

Figure 22:
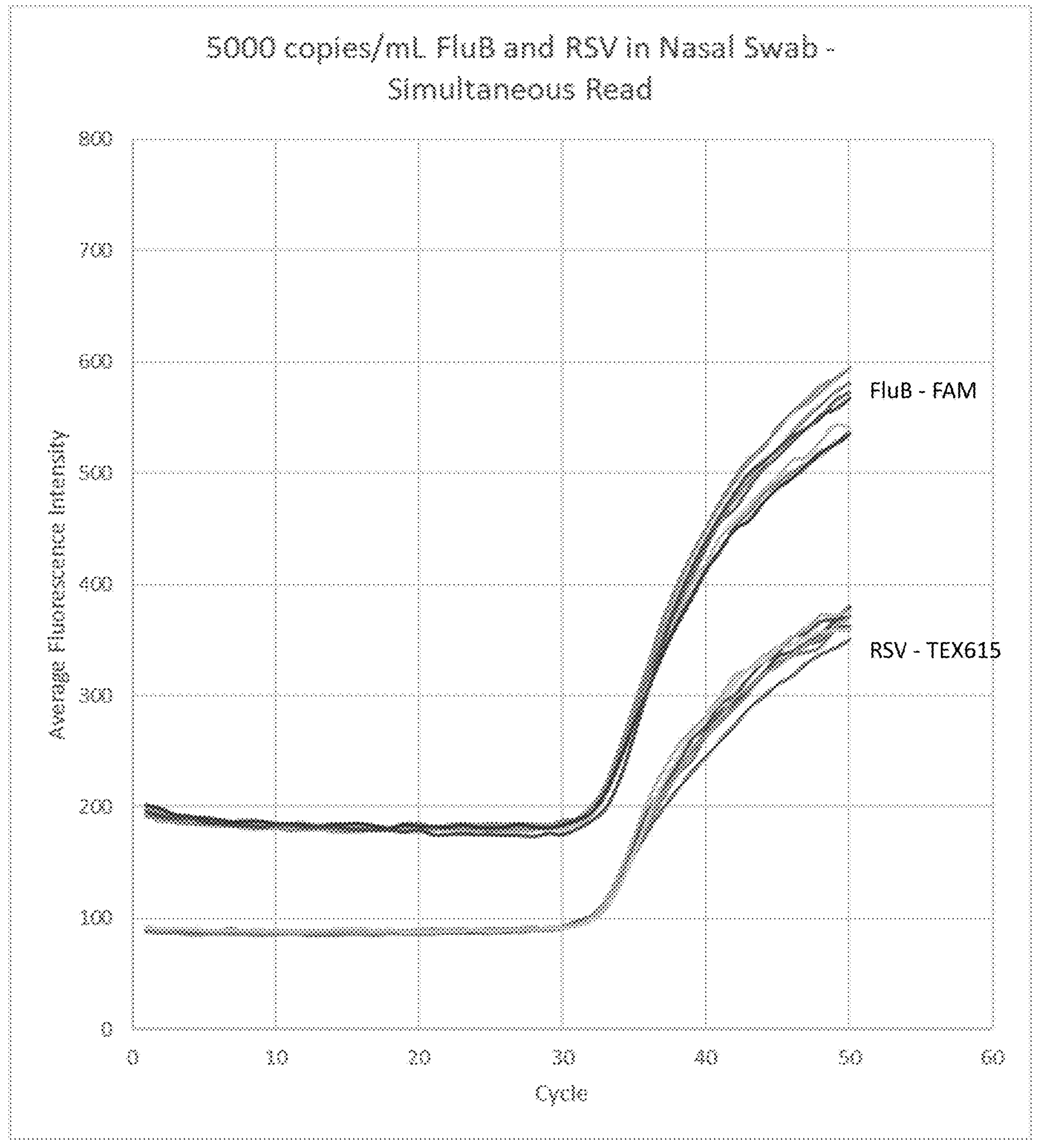
FIG. 22 shows the individual fluorescence traces collected from the RT-PCR experiments with two respiratory infectious pathogens carried out on an analytical device provided herein.
Figure 23A:
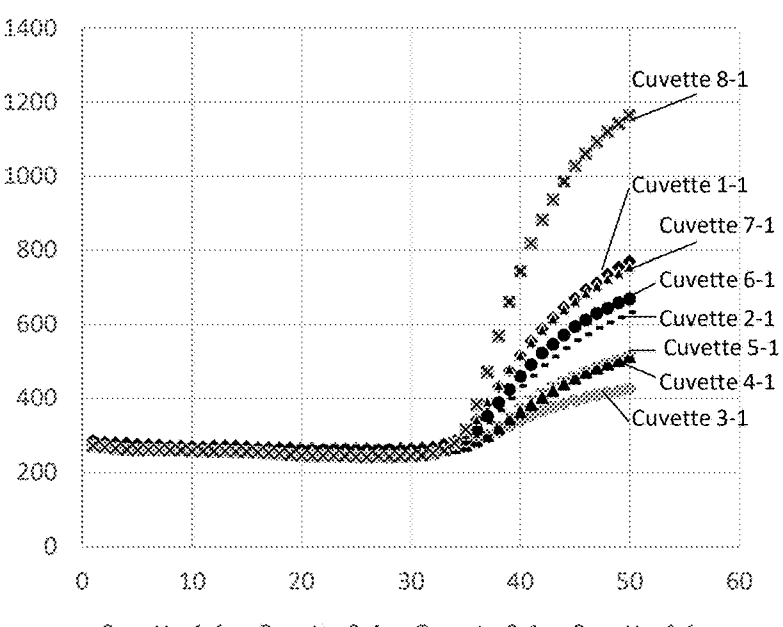
FIGS. 23A-23D show the individual fluorescence traces collected from the RT-PCR experiments with a respiratory infectious pathogen treated with a hyperbaric heating method described herein and carried out on an analytical device provided herein, indicating that PCR products were detectable between 35 and 50 cycles for the PCR reactions.
Figure 23B:
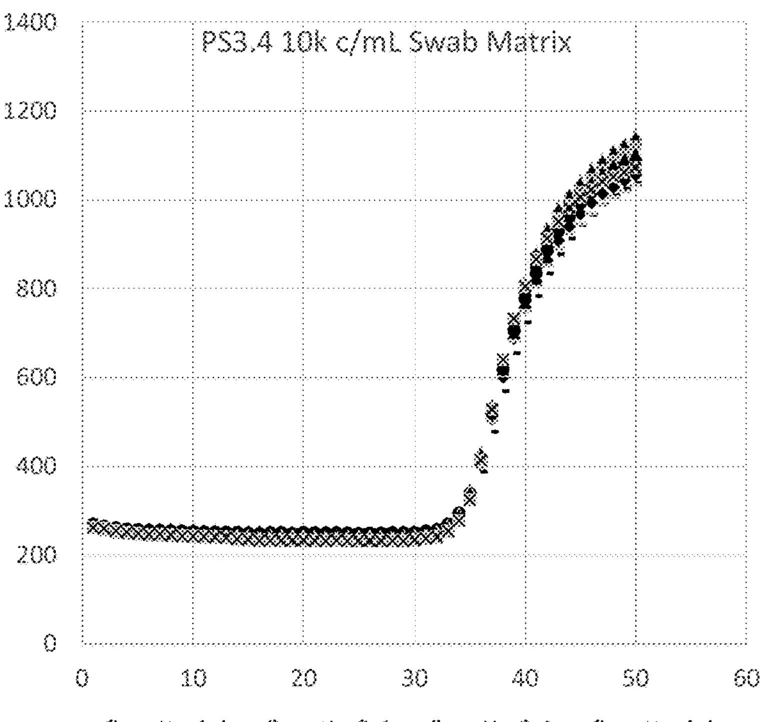
Figure 23C:
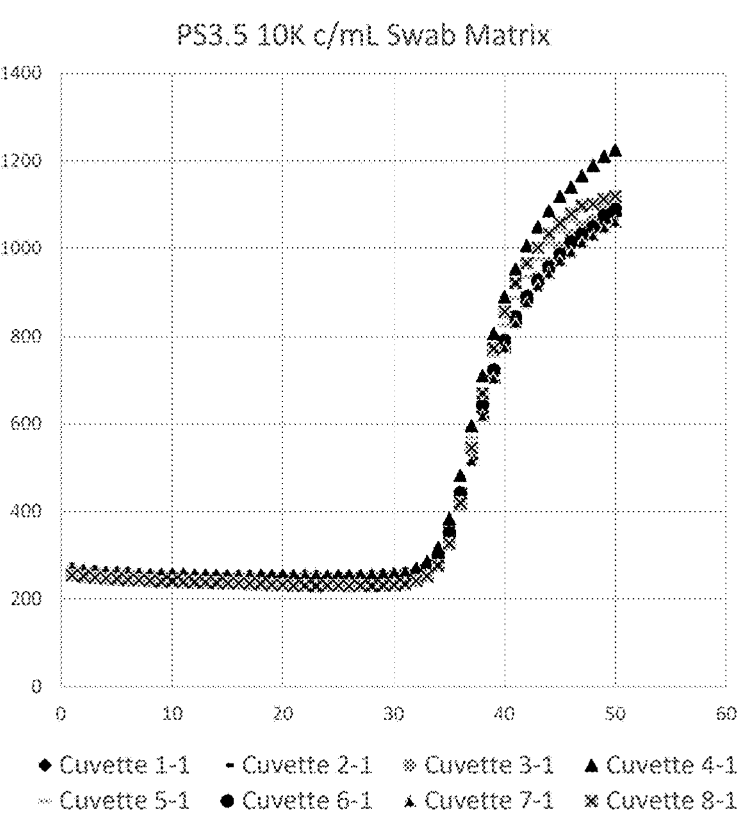
Figure 23D:
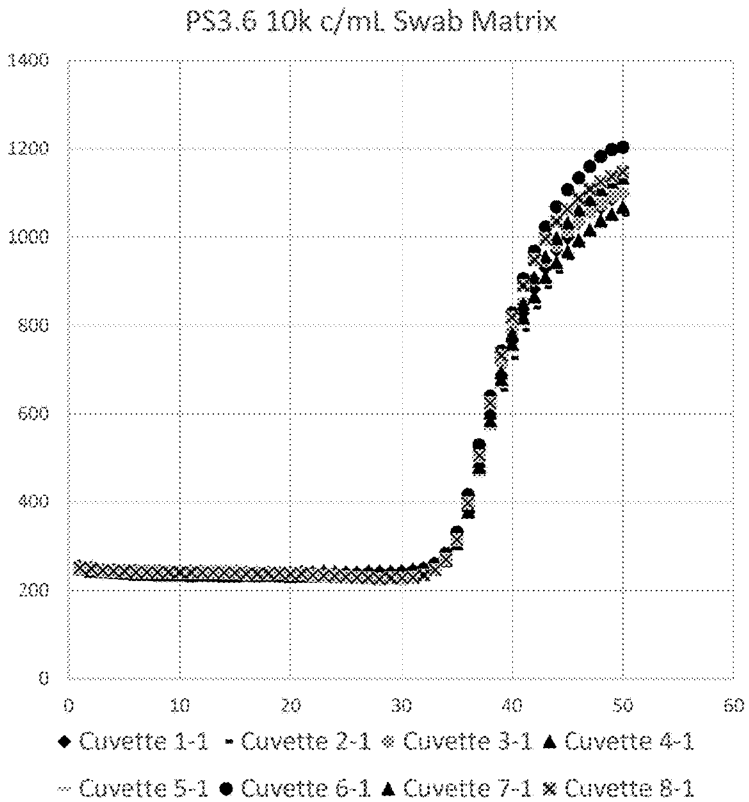

Individual fluorescence traces were collected for each simultaneous reaction replicate, as shown in FIG. 22. The fluorescence traces showed that both Flu B and RSV PCR products were detectable between 33 and 50 cycles.

Example 3: Sample Preparation by Hyperbaric Heating and Ultra-Fast Polymerase Chain Reaction with Flu B In this example, samples comprising Flu B in a nasal swab matrix were prepared via treatment by hyperbaric heating and processed and analyzed by ultra-fast polymerase chain reaction on a PCR device as described herein (FIGS. 7, 8A-8B, 9). The PCR device comprised a rotatable disc with a cuvette insert comprising 8 reaction chambers and heating elements set at 55° C., 98° C., and 65° C. In this example, 50 cycles of ultra-fast PCR were run, and real-time optical data were collected at the end of each PCR cycle. Different primer sets and probes were tested to amplify and detect Flu B.

A treatment sample comprising Flu B at a concentration of 10,000 copies/mL, 500 nM of thermostable *Thermococcus kodakarensis* (KOD), 1 mM DTT, and 10% Chelex was first prepared and heated within a closed heating chamber comprising an induction susceptor in hyperbaric heating conditions. The heating chamber was heated via induction heating at a frequency of 103.5 kHz for 15 s. During the 15 s of induction heating, the sample was heated from room temperature to a temperature between 120 degrees Celsius and 130 degrees Celsius. Following hyperbaric heating, 19 μL of the treated sample was mixed with 6 μL of a PCR reaction mix comprising 10× KAPA Buffer, 0.2 mM dNTPs, Superscript IV (10 Units), RNAsin Inhibitor (5 Units), KAPA3G DNA Polymerase (2 Units), and 4.5 mM MgSO4 for each PCR reaction mixture. A primer set and probes were added to the PCR reaction mixture at final concentrations of 1000 nM primer and 350 nM probe. In this example, 4 sets of primers and robes were tested as shown in Table 1.

TABLE 1

Primer Set and Probe Sequences used for PCR Amplification and Analysis of Flu B samples

| Primer Set | Probe | Probe Sequence |
|---|---|---|
| PS3.3 | IBMP3 A | CGCACAAAGCACAGAGCGTTCCT (SEQ ID NO: 1) |
| PS3.4 | IBMP3 AW | CGCAYAAAGCACAGAGYGTTCCT (SEQ ID NO: 2) |
| PS3.5 | IBMP3 A3W | CGCACAAAGCACAGAGYGTTCCT (SEQ ID NO: 3) |
| PS3.6 | IBMP3 A5W | CGCAYAAAGCACAGAGCGTTCCT (SEQ ID NO: 4) |

A total of 8 PCR reaction mixtures were transferred to separate chambers (e.g., cuvette) in the cuvette insert on the rotatable disc as described herein (FIG. 2). The separate chambers were heat sealed and the PCR reactions were performed with the following cycling conditions: 60 seconds of reverse transcription (55° C.), 30 seconds of polymerase activation (98° C.), followed by 50 cycles of 2 seconds of denaturation (98° C.), and 7 seconds of annealing/extension (65° C.). For thermocycling, a heating apparatus comprising gripper heating blocks at reverse transcription (55° C.), annealing (65° C.), and denaturation temperatures (98° C.) was used to transfer heat to the PCR reaction vessel. During thermocycling, the reaction vessel was moved between the heating blocks via a motor. Real-time optical data were collected at the end of each PCR cycle.

Individual fluorescence traces were collected for each cuvette, as shown in FIGS. 23A-23D. The results showed that for each of the primer sets and probes tested, the Flu B PCR products were detectable between 35 and 50 cycles for the PCR reactions in all 8 cuvettes. The results indicate that nasal swab samples treated by hyperbaric heating and processed and analyzed by ultra-fast polymerase chain reaction on a PCR device described herein maintains high sensitivity.

Example 4: Limit of Detection of Flu a and Flu B in Pooled Nasal Swab Following Sample Processing by Hyperbaric Heating and PCR Thermocycling In this example, samples comprising Flu A and Flu B in pooled nasal swab matrices were prepared via treatment by hyperbaric heating and processed and analyzed by ultra-fast polymerase chain reaction on a PCR device as described herein (FIGS. 7, 8A-8B, 9). In this example, different concentrations of Flu A and Flu B were tested to determine the limit of detection of Flu A and Flu B in pooled nasal swab matrices.

To determine the limit of detection, Flu A samples with the following concentrations were processed and analyzed by ultra-fast polymerase chain reaction: 0, 25, 60, 125, 250, 500, 1000, and 5000 copies/mL. Flu B samples with the following concentrations were processed and analyzed by ultra-fast polymerase chain reaction: 25, 60, 125, 250, 500, and 5000 copies/mL.

The Flu A and Flu B samples were processed by hyperbaric heating in treatment samples comprising 500 nM of thermostable *Thermococcus kodakarensis* (KOD), 1 mM DTT, and 10% Chelex. The samples were heated within a closed heating chamber comprising an induction susceptor in hyperbaric heating conditions. The heating chamber was heated via induction heating at a frequency of 103.5 kHz for 15 s. During the 15 s of induction heating, the sample was heated from room temperature to a temperature between 120 degrees Celsius and 130 degrees Celsius.

PCR reactions with the treated samples were then run on a PCR device as described herein (FIGS. 7, 8A-8B, 9). The treated samples were mixed with PCR reagents, primers, and probes, and the PCR reactions were carried out in separate reaction chambers that were heat sealed prior to thermocycling. During thermocycling, the reaction chambers was moved between the heating blocks via a motor. The thermocycling time was about 7.5 minutes.

Figure 24A:
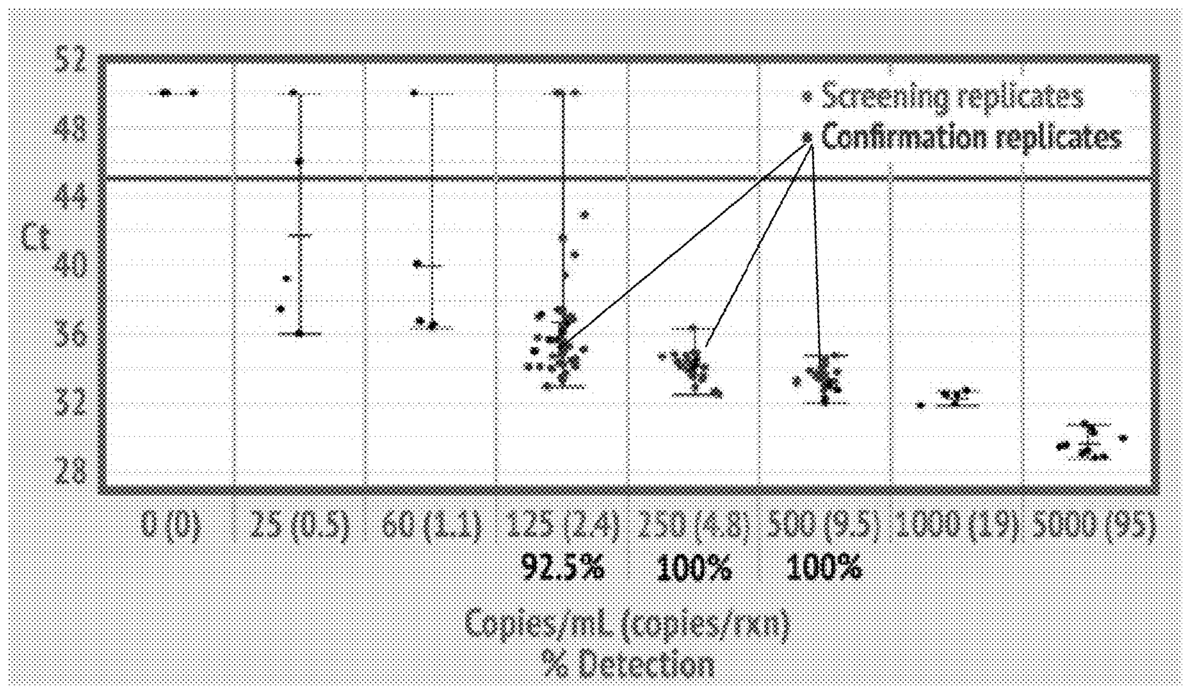
FIGS. 24A-24B show the results from RT-PCR experiments with two respiratory infectious pathogen carried out on an analytical device provided herein, indicating that nasal swab flu samples treated with hyperbaric heating and processed via fast PCR thermocycling conditions (about 7.5 min) maintains high sensitivity with average cycle threshold values of about 33-36.

The PCR results for Flu A, shown in FIG. 24A show the cycle threshold values for Flu A samples at different concentrations and indicate a limit of detection of 250 copies/mL, which yielded 100% detection across screening replicates and confirmation replicates with an average cycle threshold value of about 34. Flu A samples with a concentration of 125 copies/mL yielded 92.5% detection across screening replicates and confirmation replicates.

Figure 24B:
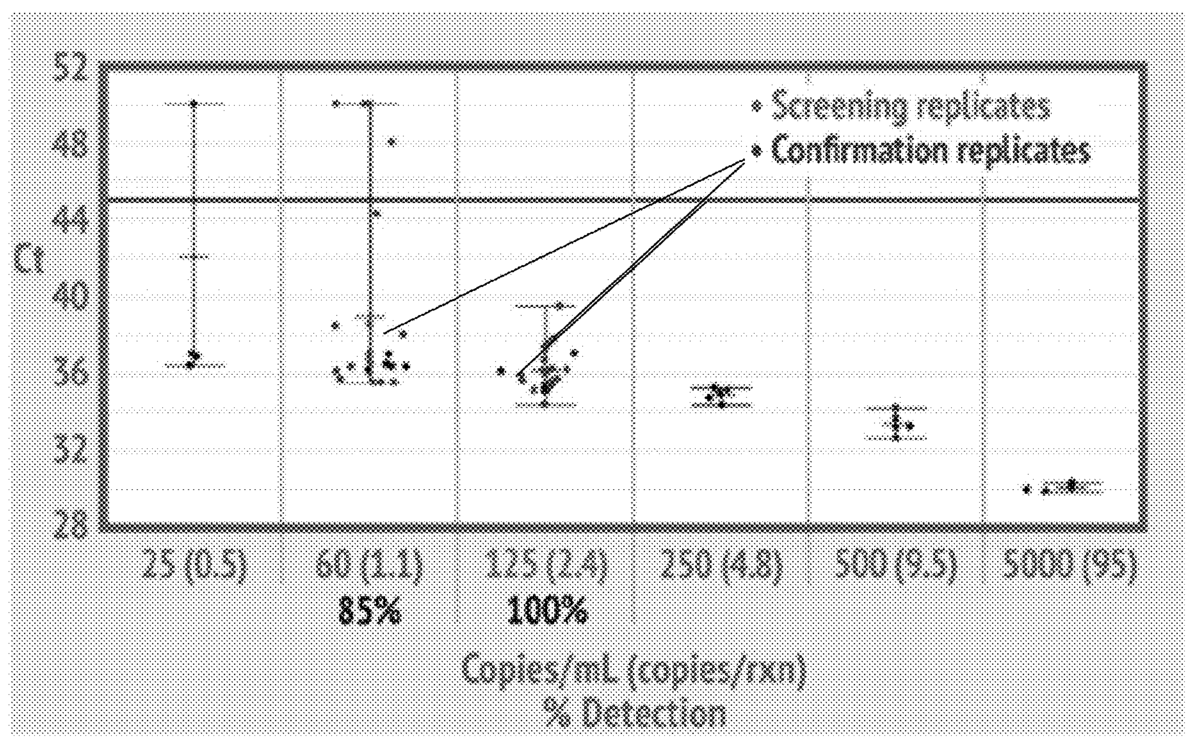
Figure 25:
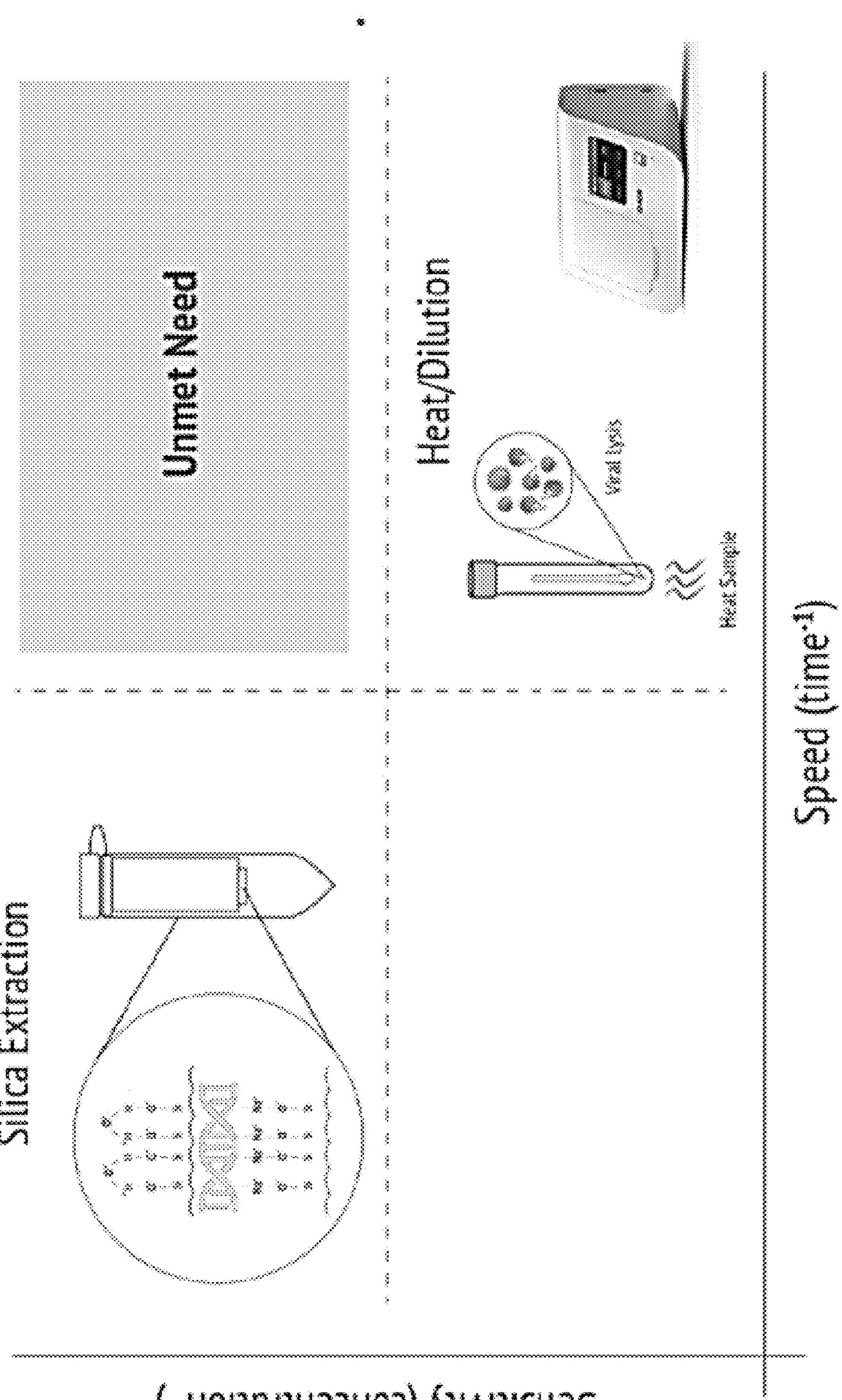
FIG. 25 shows a diagram of the tradeoffs between speed and sensitivity in contemporary nucleic acid sample preparation techniques.

The results for Flu B, shown in FIG. 24B show the cycle threshold values for Flu B samples at different concentrations and indicate a limit of detection of 125 copies/mL, which yielded 100% detection across screening replicates and confirmation replicates with an average cycle threshold value of about 36. Flu B samples with a concentration of 60 copies/mL yielded 85% detection across screening replicates and confirmation replicates.

The results indicate that nasal swab flu samples treated with hyperbaric heating and processed via fast PCR thermocycling conditions (about 7.5 min) maintains high sensitivity with average cycle threshold values of about 33-36.

Figure 26A:
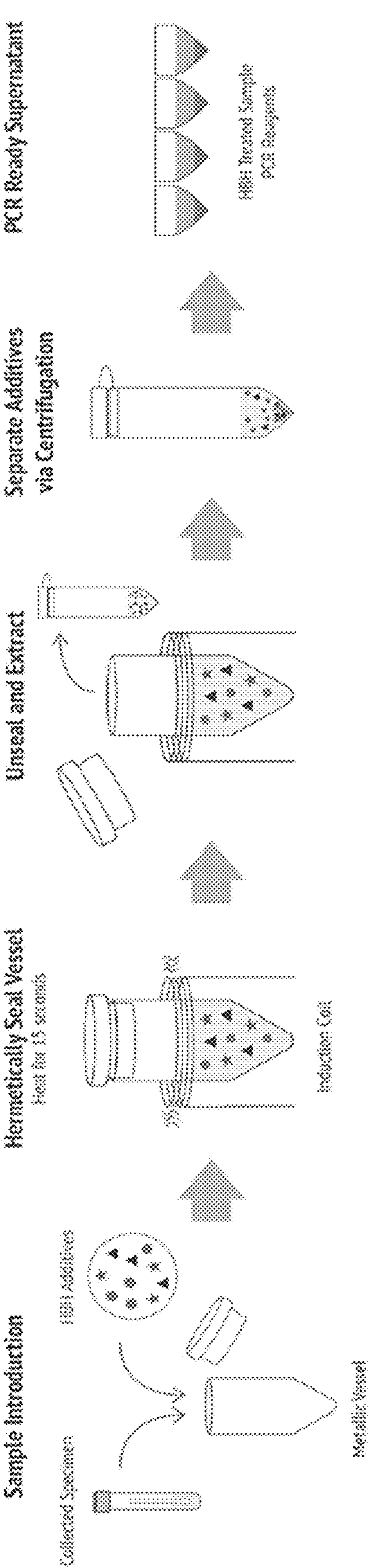
FIGS. 26A-26D show a diagram and data regarding a hyperbaric heating device provided herein.

Example 5: Hyperbaric Heating as a Simple and Effective Sample Preparation Method In this example, hyperbaric heating additive reagents were combined with the sample of interest in a metallic vessel. The added reagents, which disrupt inhibitor activity and preserve the target nucleic acids, were 500 nM of thermostable *Thermococcus kodakarensis* (KOD), 1 mM DTT, and 10% Chelex. Upon capping with an airtight seal, the vessel was heated rapidly via magnetic induction. Once the heating was complete, the sample was transferred to a microcentrifuge tube where the solids were pelleted via centrifugation, and the resulting supernatant was ready for direct PCR input (FIG. 26A).

Figure 26B:
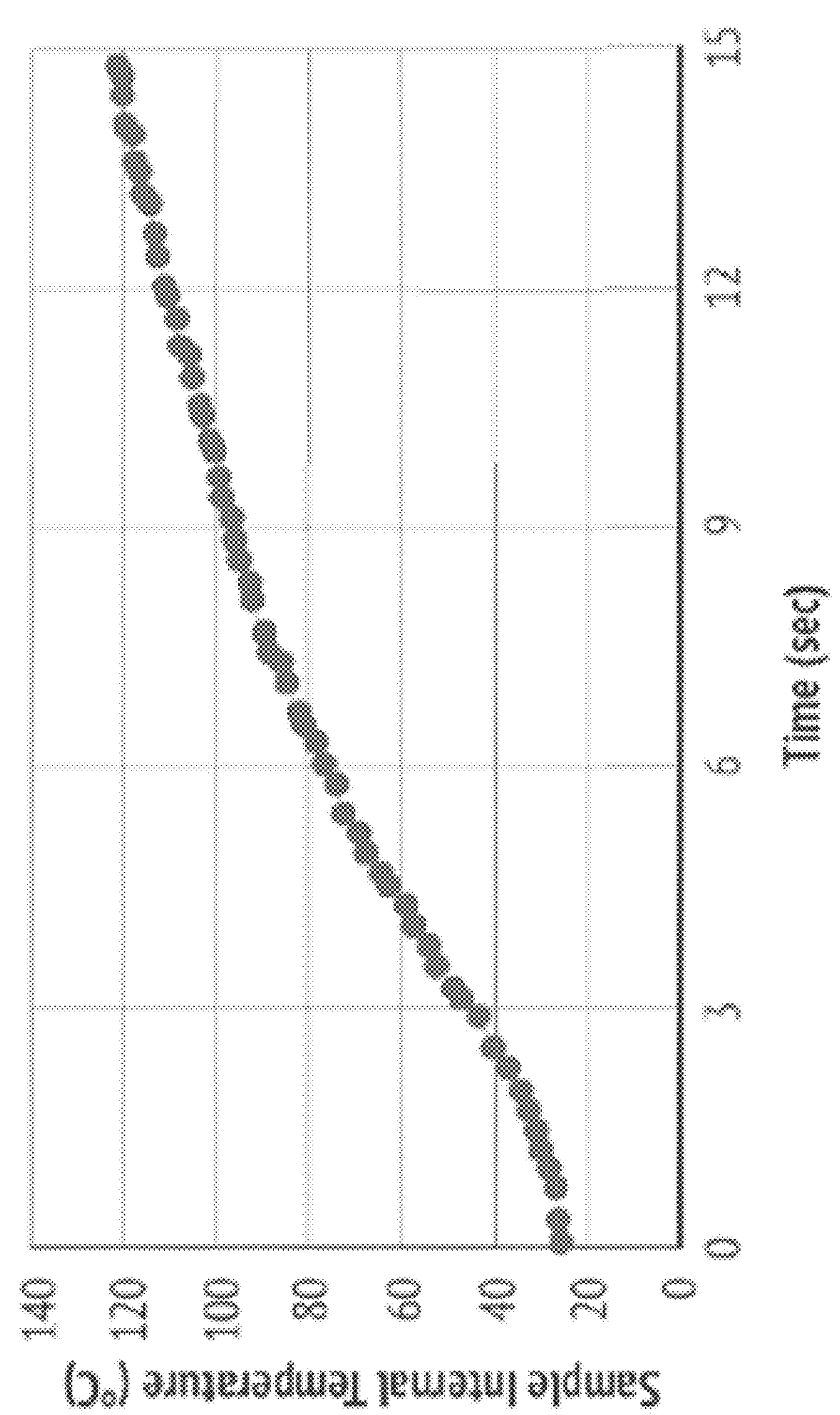

A time series of temperature of a sample within a hyperbaric heating sample vessel upon heating with magnetic induction is shown in FIG. 26B. In this experiment, temperatures reached the atmospheric boiling point of 100 degrees Celsius within 10 seconds; these temperatures can surpass 100 degrees Celsius to even higher temperatures because of pressurization within the sealed container.

Figure 26C:
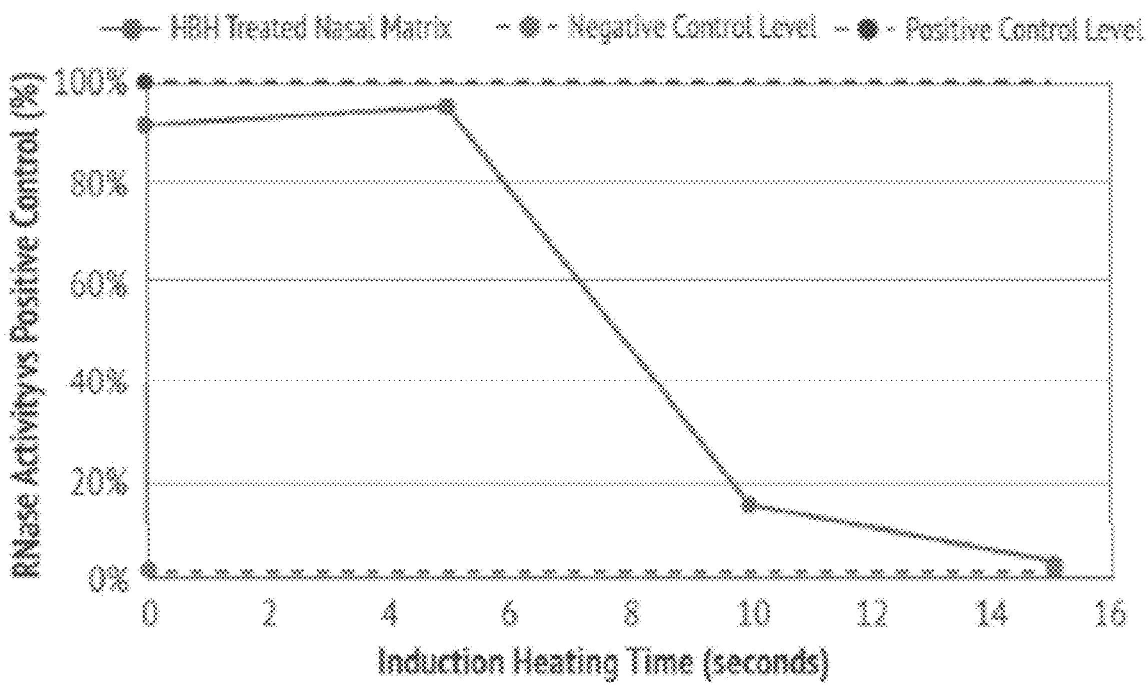

The results of an experiment measuring ribonuclease activity within a swab collected nasal matrix are shown in FIG. 26C. Ribonuclease activity within a swab collected nasal matrix was measured via fluorescence acquisition after a 10 min incubation with a fluorescent RNA probe. After 15 sec of hyperbaric heating treatment, the nasal matrix elicited equivalent fluorescence intensity as the RNase negative control, indicating nearly complete inactivation of RNases in the nasal specimen.

Figure 26D:
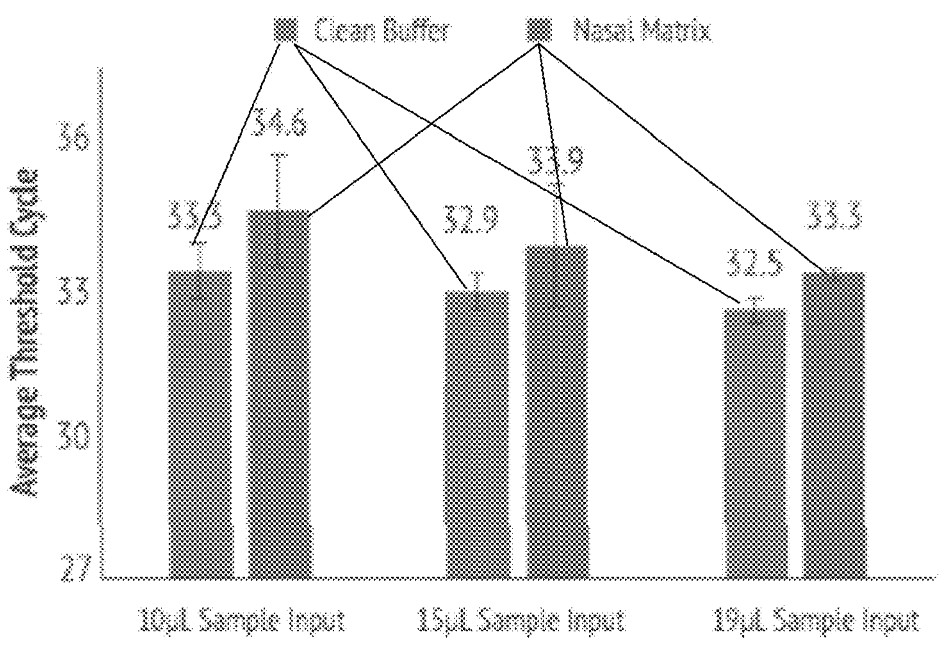

The results of a PCR cycle quantification for increasing amounts of hyperbaric heating-treated samples in 25 microliter PCR reactions are shown in FIG. 26D. The samples treated were contrived SARS-CoV-2 positive specimens both in clean collection media and in swab collected nasal matrix. PCR cycle threshold values solely improved as more sample volume was loaded into the PCR reactions, indicating effective neutralization of inhibitors present in nasal matrix by the hyperbaric heating treatment.

Figure 27A:
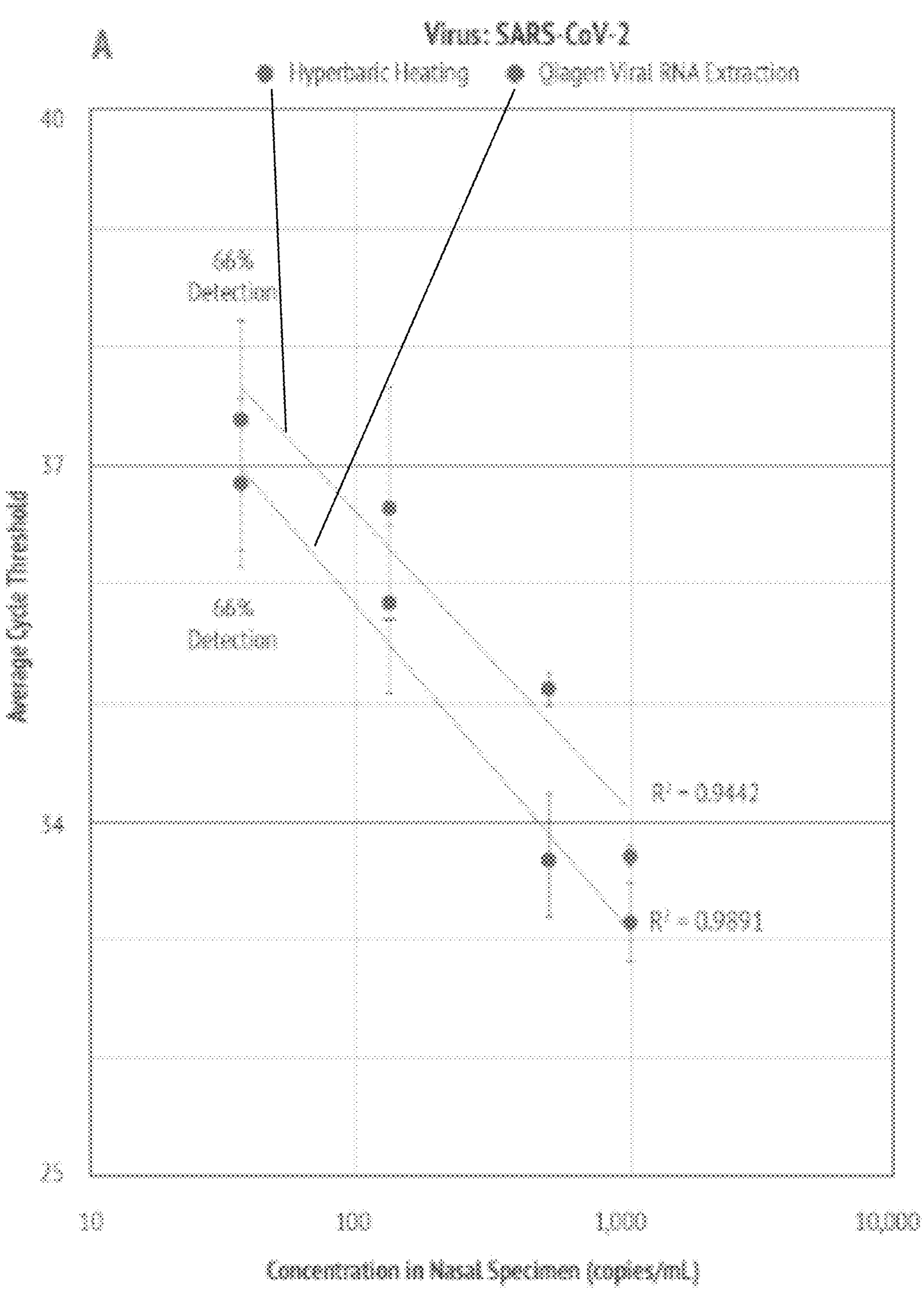
FIGS. 27A-27C show that hyperbaric heating enables highly sensitive PCR detection of multiple organisms across diverse organism types.

Example 6: Hyperbaric Heating Enables Highly Sensitive PCR Detection of Multiple Organisms Across Diverse Organism Types In this example, hyperbaric heating was quantified in different organism types and in comparison with RNA extraction. The results of a PCR cycle quantification at multiple levels of contrived SARS-CoV-2 samples in nasal specimen are shown in FIG. 27A. Hyperbaric heating-treated sample cycle threshold values, shown in green, performed equivalently to samples that were processed via Qiagen Viral RNA extraction, shown in brown. Detectable PCR amplification was achieved in samples with as little as 125 copies/milliliter of SARS-CoV-2 inactivated virus.

Figure 27B:
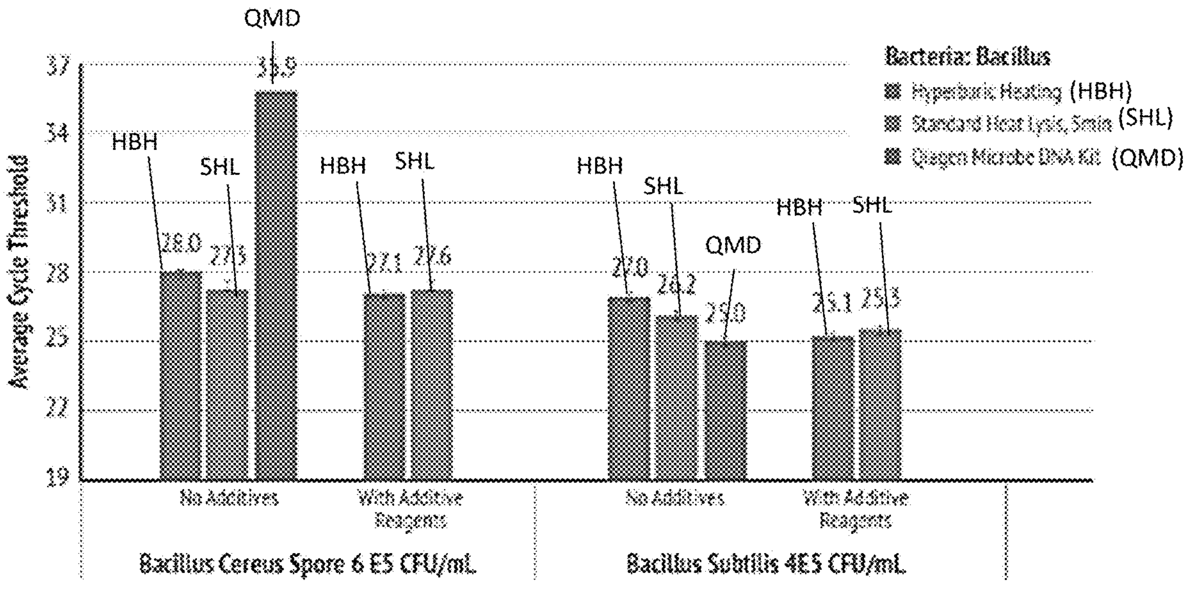
Figure 27C:
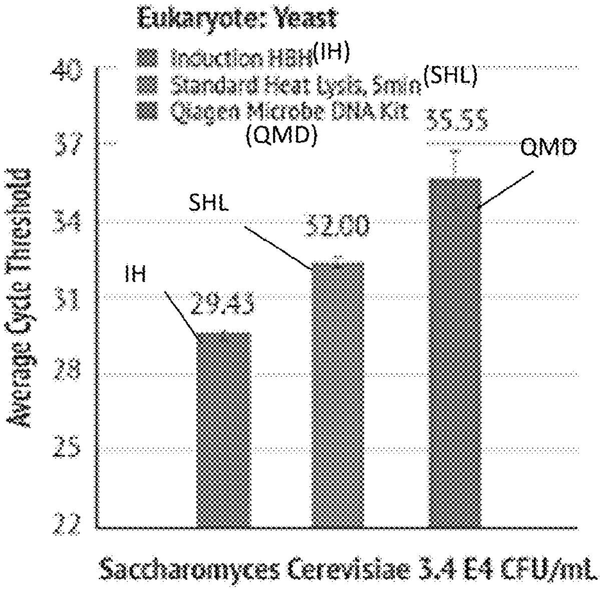
Figure 27D:
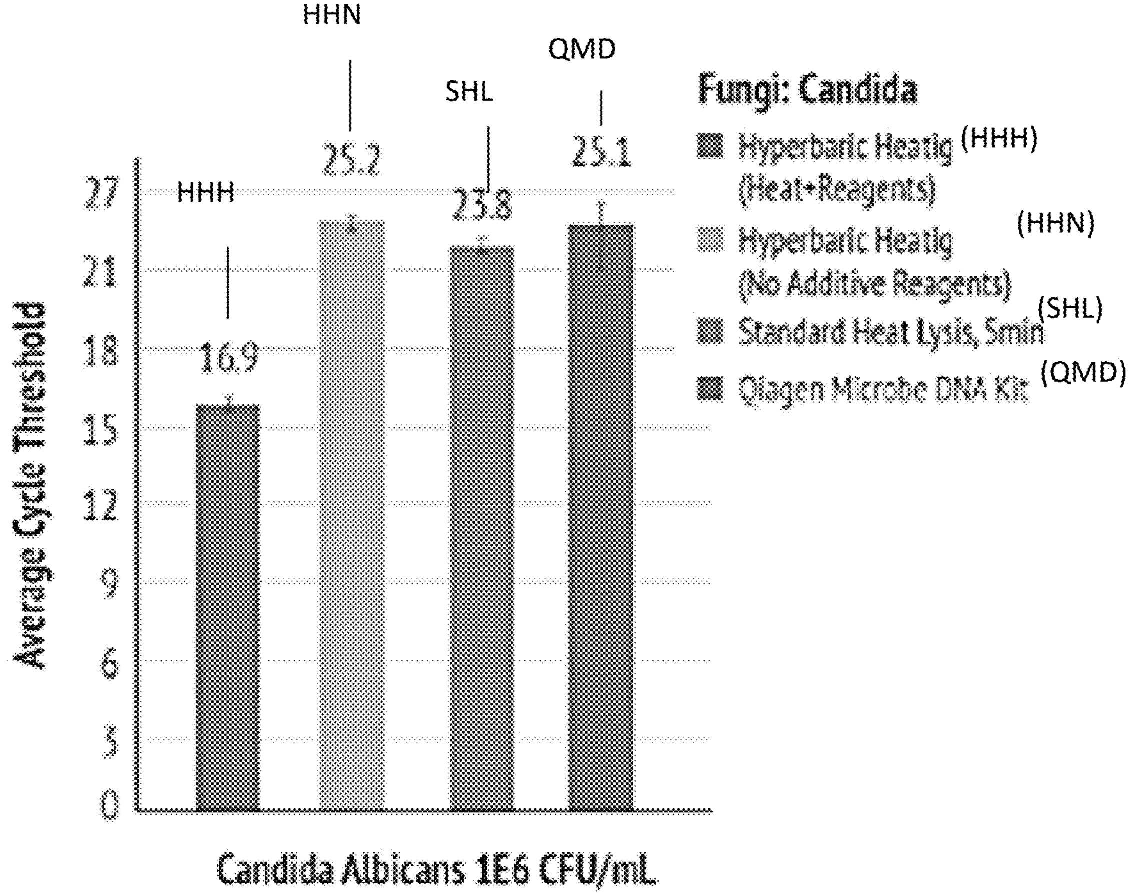
FIG. 27D shows PCR cycle quantification for *C. albicans*.

The results of PCR cycle quantification for organisms frequently targeted in molecular assays, prepared for PCR via hyperbaric heating, are shown in FIGS. 27B-27D. The organisms shown are samples of yeast (*S. cerevisiae*), fungus (*C. albicans*), and bacteria (*B. subtilis* and *B. cereus* spore). These samples were contrived in collection media and separated into aliquots. Each aliquot was prepared for PCR via three different methods: either hyperbaric heating, standard 100° C. heat treatment for 5 minutes, or nucleic acid extraction. In all cases, hyperbaric heating-treated samples elicited a PCR cycle threshold that was equivalent or faster than the other two preparation methods. PCR cycle threshold was delayed in samples in which the hyperbaric heating additive reagents (500 nM thermostable *Thermococcus kodakarensis* (KOD), 1 mM DTT, and 10% Chelex) were withheld, demonstrating the importance of the additive reagents when conducting hyperbaric heating in conjunction with the intense heating. These additive reagents ensure optimal PCR results. Results for bacteria are shown in FIG. 27B. Results for yeast are shown in FIG. 27C. Results for fungi are shown in FIG. 27D. In all cases examined, detectable amplification was achieved up to 9 cycles earlier than that of the most relevant extraction method, some of which took over 70 minutes.

Example 7: a Fully Integrated Hyperbaric Heating and PCR Prototype Instrument Produces Sensitive PCR Results In this example, an instrument where the hyperbaric heating and PCR are fully integrated was developed and tested. Frozen viral stock was thawed and diluted in a pooled nasal swab matrix in sample collection buffer. The collection buffer composition was 10 mM Tris, 1 mM EDTA, 1 mM NaCl, and 2 mg/mL BSA with 0.02% sodium azide and a pH of 8.0. Nasal swab acquisition was with a Puritan Hydraflock Swab (Part No. 25-3406-H). To acquire the nasal swab, each anterior nostril was rubbed for 15 seconds, then submerged in collection buffer for 30 seconds.

The Fast PCR Prototype Instrument was initiated and the Sample-to-Answer Protocol was loaded. The disk was then set up by opening the disk packaging and placing the core with an insert on a stable benchtop. 400 μL of the nasal swab solution was then pipetted and added to the inlet port on the Fast PCR disk. To run the Fast PCR device, a loaded disk was placed on the spindle cup within the Fast PCR instrument. The Start button was then pressed on the Fast PCR Instrument Controller Software.

The following steps took place on the Fast PCR Instrument Controller Software. First, lyophilized sample preparation reagents were resuspended with the sample by spinning for 4 sec at 2000 RPM and then oscillating for 12 sec at 9.1 Hz. Second, a copper wire coil was used to induction heat the sample for 15 sec. The prototype coils were powered at a frequency of approximately 150 kHz with a variable voltage damper in order to tune the temperature ramp rate to approximately 5.5° C. per second. Third, a hyperbaric heating valve was opened, with the laser powered at 1.0 A for 8 seconds. Fourth, the sample was spun out into the metering chamber at 3900 RPM for 20 seconds. Fifth, the metering valve was opened with the laser powered at 0.45 A for 8 seconds. Sixth, the sample was spun into the PCR Master Mix resuspension chamber at 3000 RPM for 20 seconds. Seventh, the Master Mix reagents were resuspended with the sample by oscillating for 12 seconds at 9.1 Hz. Eighth, the resuspension valve was opened with the laser powered at 0.45 A for 8 seconds. Ninth, the sample was spun into PCR reaction cuvettes at 2750 RPM with an acceleration of 250 RPM/s. Tenth, each cuvette was sealed using a channel sealing heating element at 240° C. for 2 seconds. Finally, an RT-PCR thermocycling protocol was run (Table 2). After running the Fast PCR Instrument, the disk was removed from the spindle and disposed in a Biohazard Waste container.

TABLE 2

RT-PCR Thermocycling Protocol

| Step | Temperature | Amount of Time | Number of Cycles |
|---|---|---|---|
| Reverse Transcription | 55° C. | 60 seconds | |
| Polymerase Activation | 98° C. | 30 seconds | |
| Denaturation | 98° C. | 2 seconds | 50 cycles |
| Annealing/Extension | 65° C. | 7 seconds | 50 cycles |

Figure 28:
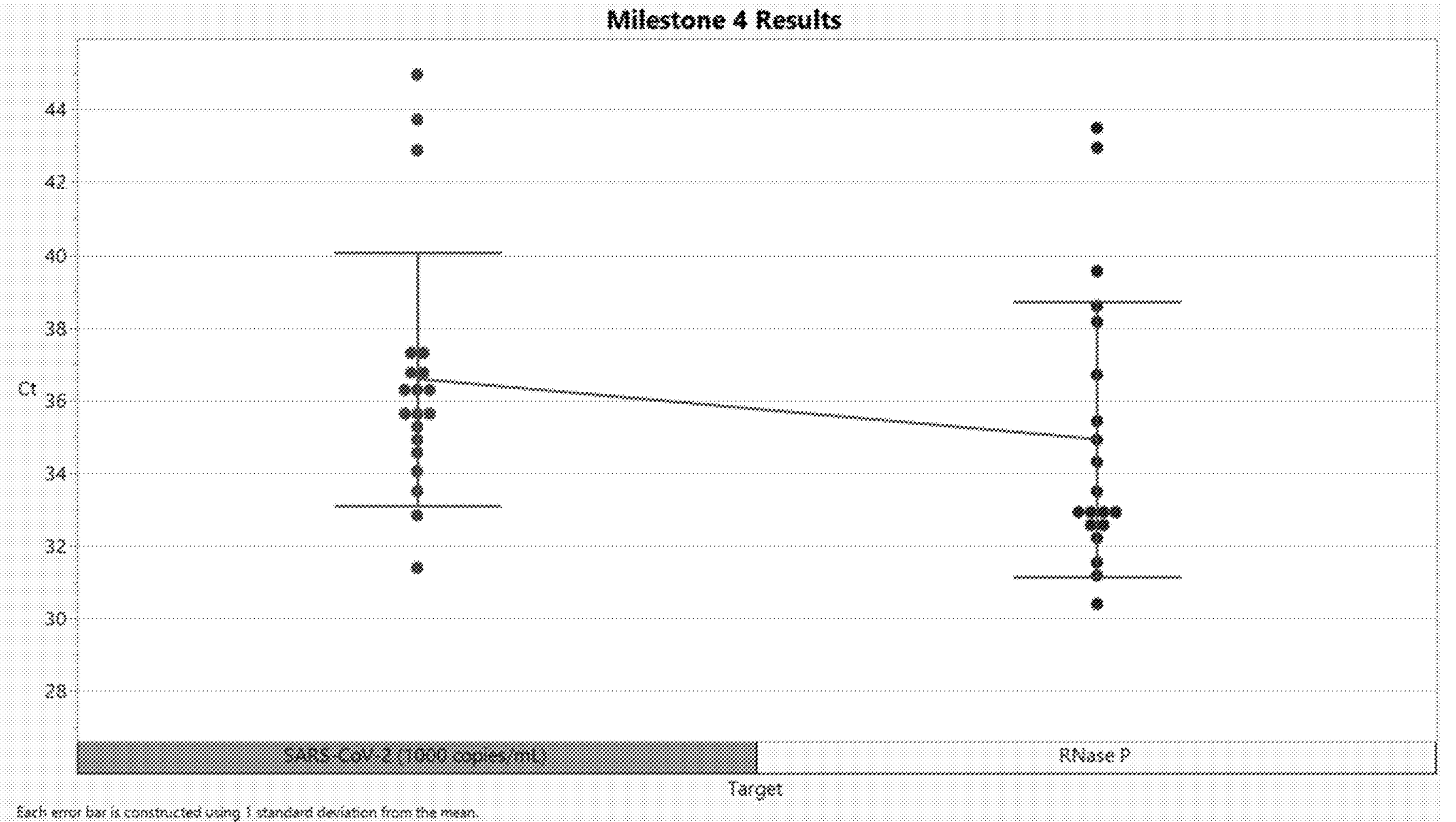
FIG. 28 shows cycle threshold results for SARS-CoV-2 and an RNase P control for a fully integrated hyperbaric heating and PCR system as provided.

The results of the experiment are shown in FIG. 28. The data demonstrate that the cycle threshold values for SARS-CoV-2 samples were not statistically significantly different from RNase P control samples. Each error bar was constructed using one standard deviation from the mean.

Example 8: Hyperbaric Nucleic Acid Sample Preparation of Microbial Organisms in Urine Samples In this example, sample was acquired either by creating a contrived sample in a desired sample matrix or by using an appropriate positive clinical sample. A contrived sample was created by diluting organism sample stock to an appropriate concentration using appropriate sample media. For example, *C. albicans* was diluted in culture fluid from 6.3E6 to 1E5 CFU/mL in urine. For a positive clinical sample, a sample ID and diagnosis from the clinical sample source was noted.

1.8 mL of sample was then loaded into a 2 mL microcentrifuge tube and spun in a centrifuge for 1 minute at 10,000×g. The supernatant was removed without disturbing the pellet. The pellet was resuspended in 1.8 mL of sample buffer (10 mM Tris, 1 mM EDTA, 1 mM NaCl, 2 mg/mL BSA). The sample was then spun again for 1 minute at 10,000×g in the centrifuge. The supernatant was then removed without disturbing the pellet. The pellet was then resuspended in 400 μL of sample buffer (10 mM Tris, 1 mM EDTA, 1 mM NaCl, 2 mg/mL BSA).

Next, the metallic reaction vessel was prepared with reagent components that are required for hyperbaric heating. A sample processing bead was prepared with 1 mM dithiothreitol (DTT), 1 mM tris carboxyethyl phosphine (TCEP), 0.5 μM single-stranded DNA binding protein, and final 12% weight/volume Chelex-100 chelating resin.

The prepared sample was then added to the reaction vessel. The reaction vessel was sealed with an airtight camp. The reaction vessel was placed within an induction coil and heated for 15 seconds. Power requirements of the induction coil can vary depending on the composition and dimensions of the coil. The vessel was then allowed to cool at ambient temperatures until it was safe to handle. The reaction vessel was then placed in a centrifuge and spun to collect material at the bottom of the vessel. This ensured that any evaporated fluid was condensed in order to maximize the collected amount.

The reaction vessel was then opened and the entirety of the sample was aspirated into a microcentrifuge tube. The microcentrifuge tube was then spun to pellet Chelex and other solids. Finally, the supernatant was retrieved from the microcentrifuge tube. This supernatant was then ready to use as a PCR sample.

TABLE 3

Hyperbaric heating sample prep for PCR targeting microbes in urine.

| | Commercial Methods (Nucleic Acid Extraction, Heat Lysis) | | Hyperbaric Heating (15 seconds) | |
|---|---|---|---|---|
| Target Organism (Concentration) | Commercial Method (Time in min.) | Commercial Method Threshold Cycle | Hyperbaric Heating Threshold Cycle | Ct Differential |
| *C. albicans* Fungi (1E5 CFU/mL) in urine | Qiagen DNeasy UltraClean Microbe DNA Kit (75) | 20.9 ± 0.1 | 21.8 ± 0.1 | +0.9 |
| | 100° C. Heat Lysis (10) | 43.4 ± 2.1 | | −21.6 |

Threshold cycle values for a variety of organisms prepared either with hyperbaric heating, standard heat lysis, or nucleic acid extraction. *Candida albicans* was spiked into pooled urine matrix. After buffer exchange into sample buffer, 400 μL was prepared for PCR via hyperbaric heating. 400 μL of buffer-exchanged sample was heated for 100° C. for 10 minutes as a standard heat lysis control. The extraction control sample was prepared for PCR using the Qiagen Microbe DNA kit, which required 1.8 mL of sample and was performed in 75 minutes. The 15-second hyperbaric heating yielded equivalent Ct values as that of the extraction method and far earlier Ct values than the standard heat lysis method. PCR amplification was performed on the Applied Biosystems Quantstudio 5 PCR instrument.

What is claimed:

1. A method of detecting the presence or absence of a target nucleic acid in a sample, the method comprising:

(a) providing a rotatable PCR disc comprising a closed loading chamber, a plurality of reaction chambers, a channel connecting the closed loading chamber to the plurality of reaction chambers, and an exit valve connecting the closed loading chamber to the channel, wherein the closed loading chamber contains the sample;

(b) heating the sample in the closed loading chamber in a hyperbaric condition to a temperature above 100° C. to produce a heat-treated sample;

(c) opening the exit valve, thereby opening the closed loading chamber, and rotating the rotatable PCR disc such that the heat-treated sample flows to the plurality of reaction chambers via the channel; and (d) amplifying the target nucleic acid, if present, in the heat-treated sample in the plurality of reaction chambers.

2. The method of claim 1, wherein, in (d), each of the plurality of reaction chambers comprises a PCR reaction mixture comprising a primer, a polymerase, and a plurality of nucleotides, and wherein (d) further comprises rotating the rotatable PCR disc to bring the plurality of reaction chambers adjacent to a first heating element, wherein the first heating element heats the plurality of reaction chambers to a denaturing temperature of 90° C. to 99° C.

3. The method of claim 2, wherein (d) further comprises rotating the rotatable PCR disc to bring the plurality of reaction chambers adjacent to a second heating element, wherein the second heating element heats the plurality of reaction chambers to an annealing temperature of 50° C. to 74° C.

4. The method of claim 3, wherein the heat-treated sample comprises the target nucleic acid, and wherein the method further comprises (e) detecting the target nucleic acid or an amplification product thereof.

5. The method of claim 4, wherein the target nucleic acid or the amplification product thereof is detectable after amplifying the target nucleic acid from 10 to 50 molecular amplification cycles.

6. The method of claim 4, wherein the target nucleic acid or the amplification product thereof is detectable after amplifying the target nucleic acid from 28 to 35 molecular amplification cycles.

7. The method of claim 4, further comprising sequencing the target nucleic acid or the amplification product thereof.

8. The method of claim 4, further comprising, prior to flowing the heat-treated sample into the plurality of reaction chambers, mixing the heat-treated sample with a PCR reagent selected from: a polymerase, a plurality of nucleotides, buffer, reverse transcriptase, primers, and fluorescent probes.

9. The method of claim 4, wherein the method further comprises hybridizing a fluorescent probe to the target nucleic acid or the amplification product thereof, exposing the plurality of reaction chambers to an excitation light, and detecting an emission wavelength corresponding to a presence of the target nucleic acid or the amplification product thereof.

10. The method of claim 1, further comprising, after (c) and prior to (d), heating and compressing the channel, thereby sealing the channel and preventing fluid communication between the plurality of reaction chambers.

11. The method of claim 1, wherein the sample is a bodily sample comprising the target nucleic acid, wherein:

(i) the bodily sample is selected from a blood sample, a lacrimal fluid sample, a saliva sample, a mucus sample, a sputum sample, a feces sample, a cerebrospinal fluid sample, and a urine sample; and (ii) the target nucleic acid is not extracted, isolated, or otherwise purified from the bodily sample prior to the heating in (b).

12. The method of claim 1, wherein, in (a), the sample comprises a plurality of molecular amplification inhibitors.

13. The method of claim 12, wherein the plurality of molecular amplification inhibitors comprises: (i) a plurality of agents that are capable of binding to the target nucleic acid if present, (ii) a plurality of DNases, (iii) a plurality of RNases, or (iv) a plurality of proteases.

14. The method of claim 13, wherein the heating of the sample inactivates at least 60% of the plurality of molecular amplification inhibitors.

15. The method of claim 1, wherein the sample comprises one or more reagents selected from: a chelating agent, a single stranded nucleic acid binding protein, a reducing agent, and a stabilizer.

16. The method of claim 15, wherein the sample comprises a chelating agent, a single stranded nucleic acid binding protein, and a reducing agent.

17. The method of claim 16, wherein the sample further comprises a stabilizer.

18. The method of claim 17, wherein the stabilizer is selected from bovine serum albumin and gelatin.

19. The method of claim 15, wherein the sample further comprises a protease or a nuclease inhibitor.

20. The method of claim 1, wherein the heating of the sample in the hyperbaric condition occurs over a ramp time from a first temperature to a second temperature, wherein the second temperature is the temperature above 100° C., wherein the ramp time is from about 3 seconds to about 50 seconds.

21. The method of claim 20, further comprising maintaining the sample at the second temperature for a maintenance time from about 5 seconds to about 120 seconds to produce the heat-treated sample, and subsequently cooling the heat-treated sample.

22. The method of claim 1, wherein the heating of the sample in the hyperbaric condition occurs at a temperature ramp rate of about 5° C. per second to about 50° C. per second.

23. The method of claim 1, wherein the heating of the sample in the hyperbaric condition comprises heating the sample to a temperature of about 105° C. to about 160° C.

24. The method of claim 1, wherein the heating in (b) comprises induction heating.

25. The method of claim 1, wherein (c) comprises performing the rotation of the rotatable PCR disc at a speed from about 500 RPM to about 15,000 RPM.

26. The method of claim 1, wherein each of the plurality of reaction chambers has a volume of 5 μL to 100 μL.

27. The method of claim 1, wherein the rotatable PCR disc is composed at least in part of a thermoplastic material.

28. The method of claim 27, wherein the channel is composed at least in part of a thermoplastic material.

29. The method of claim 1, wherein the closed loading chamber is composed at least in part of a metal.

30. The method of claim 1, wherein the heat-treated sample comprises the target nucleic acid, wherein the target nucleic acid comprises RNA.

* * * * *